US011691939B2

(12) United States Patent
Ortlund et al.

(10) Patent No.: US 11,691,939 B2
(45) Date of Patent: Jul. 4, 2023

(54) MODULATORS OF LIVER RECEPTOR HOMOLOGUE 1 (LRH-1) AND USES

(71) Applicant: Emory University, Atlanta, GA (US)

(72) Inventors: Eric Ortlund, Decatur, GA (US);
Suzanne Mays, Marietta, GA (US);
Nathan Jui, Decatur, GA (US);
Autumn Flynn, Decatur, GA (US);
Michael Dugan, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 17/071,382

(22) Filed: Oct. 15, 2020

(65) Prior Publication Data
US 2021/0047258 A1    Feb. 18, 2021

Related U.S. Application Data

(62) Division of application No. 16/495,092, filed as application No. PCT/US2018/022923 on Mar. 16, 2018, now Pat. No. 10,843,996.

(60) Provisional application No. 62/473,036, filed on Mar. 17, 2017.

(51) Int. Cl.
| | | |
|---|---|---|
| C07C 59/54 | (2006.01) | |
| C07C 35/50 | (2006.01) | |
| C07C 39/23 | (2006.01) | |
| C07C 43/23 | (2006.01) | |
| C07C 49/683 | (2006.01) | |
| C07C 49/83 | (2006.01) | |
| C07C 215/70 | (2006.01) | |
| C07C 255/47 | (2006.01) | |
| C07C 271/34 | (2006.01) | |
| C07C 307/02 | (2006.01) | |
| C07C 309/66 | (2006.01) | |
| C07D 249/04 | (2006.01) | |
| C07F 9/09 | (2006.01) | |
| C07F 9/572 | (2006.01) | |

(52) U.S. Cl.
CPC ............. *C07C 59/54* (2013.01); *C07C 35/50* (2013.01); *C07C 39/23* (2013.01); *C07C 43/23* (2013.01); *C07C 49/683* (2013.01); *C07C 49/83* (2013.01); *C07C 215/70* (2013.01); *C07C 255/47* (2013.01); *C07C 271/34* (2013.01); *C07C 307/02* (2013.01); *C07C 309/66* (2013.01); *C07D 249/04* (2013.01); *C07F 9/091* (2013.01); *C07F 9/572* (2013.01); *C07C 2602/22* (2017.05)

(58) Field of Classification Search
CPC .................................................... C07C 59/54
See application file for complete search history.

(56) References Cited

U.S. PATENT DOCUMENTS

| | | | |
|---|---|---|---|
| 7,939,544 B2 | 5/2011 | George | |
| 8,598,199 B2 | 12/2013 | George | |
| 10,843,996 B2 | 11/2020 | Ortlund | |
| 2004/0038862 A1 | 2/2004 | Goodwin | |
| 2008/0227864 A1 | 9/2008 | Goodwin | |
| 2013/0210143 A1 | 8/2013 | St-Onge | |

FOREIGN PATENT DOCUMENTS

WO    2005082344    9/2005

OTHER PUBLICATIONS

Benod et al. Structure-based Discovery of Antagonists of Nuclear Receptor LRH-1, The Journal of Biological Chemistry vol. 288, No. 27, pp. 19830-19844, Jul. 5, 2013.
Busby et al. Discovery of Inverse Agonists for the Liver receptor homologue-1 (LRH1; NR5A2), 2011.
Extended European Search Report, EP Application 18766936.1, dated Nov. 24, 2020.
Lalit et al. A combined pharmacophore modeling, 3D-QSAR and molecular docking study of substituted bicyclo-[3.3.0]oct-2-enes as liver receptor homolog-1 (LRH-1) agonists, Journal of Molecular Structure, 1049 (2013) 315-325.
Lee et al. A nuclear-receptor-dependent phosphatidylcholine pathway with antidiabetic effects, Nature 474, 506-510 (2011).
Mays et al. Crystal Structures of the Nuclear Receptor, Liver Receptor Homolog 1, Bound to Synthetic Agonists, The Journal of Biological Chemistry, 2016, vol. 291, No. 49, pp. 25281-25291.
Nodolny et al. Liver receptor homolog-1 (LRH-1): a potential therapeutic target for cancer, Cancer Biology & Therapy 16:7, 997-1004, 2015.
Pubchem CID 1864273 (3As,6aR)-2-hydroxy-3,3a,6,6a-tetrahydro-2H-pentalen-1-one.
Pubchem 24825430 (3aS,6aR)-5-methyl-N,4-diphenyl-1,2,3,3a,6,6a-hexahydropentalen-3a-amine.
Wender et al. Three-Component Cycloadditions: The First Transition Metal-Catalyzed [5+2+1] Cycloaddition Reactions, J Am Chem Soc. 2002, 124(12):2876-7.
Whitby et al. Identification of Small Molecule Agonists of the Orphan Nuclear Receptors Liver Receptor Homolog-1 and Steroidogenic Factor-1, J. Med. Chem. 2006, 49, 6652-6655.
Whitby et al. Small Molecule Agonists of the Orphan Nuclear Receptors Steroidogenic Factor-1 (SF-1, NR5A1) and Liver Receptor Homologue-1 (LRH-1, NR5A2), J. Med. Chem. 2011, 54, 2266-2281.
Cato et al. Differential Modulation of Nuclear Receptor LRH-1 through Targeting Buried and Surface Regions of the Binding Pocket, J. Med. Chem. 2022, 65, 6888-6902.

*Primary Examiner* — Golam M Shameem
(74) *Attorney, Agent, or Firm* — Emory Patent Group

(57) ABSTRACT

This disclosure relates to modulators of liver receptor homologue 1 (LRH-1) and methods of managing disease and conditions related thereto. In certain embodiments, modulators are derivatives of hexahydropentalene. In certain embodiments, this disclosure relates to methods of treating or preventing cancer, diabetes, or cardiovascular disease by administering an effective amount of a hexahydropentalene derivative disclosed herein.

14 Claims, 12 Drawing Sheets

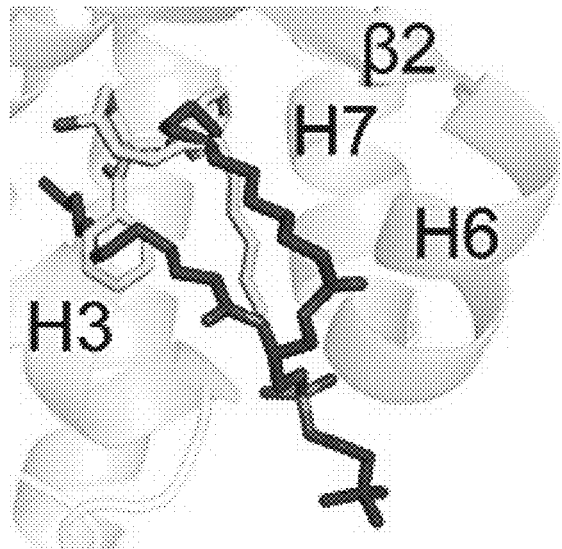
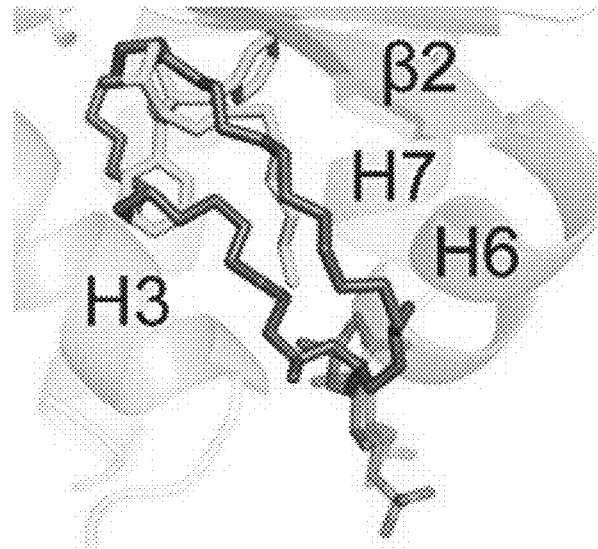
FIG. 3C  FIG. 3D
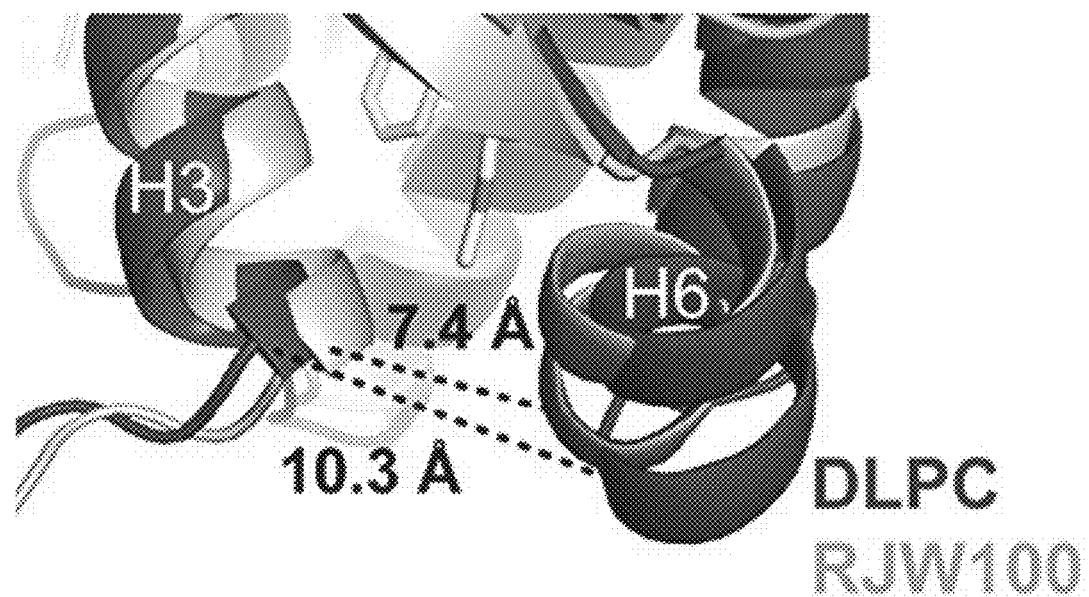
FIG. 3E

MODULATORS OF LIVER RECEPTOR HOMOLOGUE 1 (LRH-1) AND USES

CROSS-REFERENCE TO RELATED APPLICATIONS

This application is a division of U.S. application Ser. No. 16/495,092 filed Sep. 17, 2019 that granted as U.S. Pat. No. 10,843,996 on Nov. 24, 2020, which is the National Stage of International Application No. PCT/US2018/022923 filed Mar. 16, 2018, which claims the benefit of U.S. Provisional Application No. 62/473,036 filed Mar. 17, 2017. The entirety of each of these applications is hereby incorporated by reference for all purposes.

STATEMENT REGARDING FEDERALLY FUNDED RESEARCH

This invention was made with government support under DK095750 and DK111171 awarded by the National Institutes of Health. The government has certain rights in the invention.

BACKGROUND

Liver receptor homologue 1 (LRH-1) is a nuclear hormone receptor (NR) and acts as a transcription factor to control gene expression. Traditionally, LRH-1 was identified to be involved with cholesterol homeostasis and early fetal development. The use of an LRH-1 agonist for treating diabetes is reported in Lee et al. Nature, 2011, 474, 506-510. The medium-chain dietary phospholipid, dilauroyl-phosphatidylcholine (DLPC) was identified as a LRH-1 agonist. Diabetic mice fed DLPC had improved glucose tolerance and reduced hepatic fat accumulation, as well as reduced quantities of circulating insulin, triglycerides and free fatty acids. The anti-diabetic effects were associated with changes in expression of a select subset of LRH-1 target genes involved with lipid metabolism. Importantly, the differences in health and on gene expression by DLPC were absent in LRH-1 liver-specific conditional knockout mice, directly implicating LRH-1 in these effects. In addition to DLPC, LRH-1 binds phosphatidyl-inositol 3,4,5-trisphosphate (PIP3), which is an important signaling lipid in diabetes.

LRH-1 is also aberrantly overexpressed in certain cancers. It is believed to promote tumor growth through estrogen receptor and β-catenin signaling. See Christina et al. Liver receptor homolog-1 (LRH-1): a potential therapeutic target for cancer. Cancer Biol Ther, 2015, 16(7): 997-1004. Whitby et al. report small molecule agonists of LRH-1. J Med Chem 2006, 49(23):6652-5. See also Whitby et al., J Med Chem, 2011, 54, 2266-2281; Busby et al. Probe Reports from the NIH Molecular Libraries Program, 2010, 1:1-55; Benod et al. Antagonists of nuclear receptor LRH-1. J Biol Chem, 2013, 288:19830-44, US2013/0210143, US2008/0227864, and US 2004/0038862.

Mays et al. report the crystal structures of LRH-1 bound to synthetic agonists. J Biol Chem, 2016, 291(49):25281-25291.

References cited herein are not an admission of prior art.

SUMMARY

This disclosure relates to modulators of liver receptor homologue 1 (LRH-1) and methods of managing diseases and conditions related thereto. In certain embodiments, modulators are derivatives of hexahydropentalene. In certain embodiments, this disclosure relates to methods of treating or preventing diabetes, cancer, or cardiovascular disease by administering an effective amount of a hexahydropentalene derivative disclosed herein to a subject in need thereof. In certain embodiments, derivatives of hexahydropentalene have the following formula:

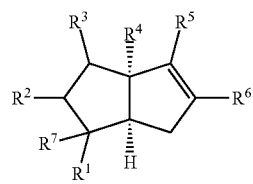

or salts thereof wherein the substituents are reported herein.

In certain embodiments, the disclosure contemplates pharmaceutical compositions comprising compounds disclosed herein or pharmaceutically acceptable salts thereof and pharmaceutically acceptable excipients. In certain embodiments, the pharmaceutical products may be in the form of a tablets, pills, capsules, gels, granules, or aqueous buffer solutions.

BRIEF DESCRIPTION OF THE DRAWINGS

FIG. 3C shows superposition of RR-RJW100 with the ligand coordinates from DLPC (purple, PDB 4DOS) indicating different binding mode of RR-RJW100 compared with the PL ligands.

FIG. 3D, superposition of RR-RJW100 with the ligand coordinates from PIP3 (PDB 4RWV) indicating different binding mode of RR-RJW100 compared with the PL ligands.

FIG. 3E shows DLPC expands the width at the mouth of the pocket by ~3 Å compared with RR-RJW100. The width was measured from Thr-341 to Asn-419 (α-carbons).

FIG. 5A shows a close-up of the views of the binding pockets from the structures of LRH-1 bound to RR-RJW100 depicting side chains of amino acid residues that interact with each ligand. Residues that also interact with GSK8470 are shown, whereas unique interactions made by RR-RJW100 are shown in gray. Portions of the electron density maps are shown to highlight the interactions with Thr-352 through water (FO-FC, contoured to 1a).

Figure 5A:
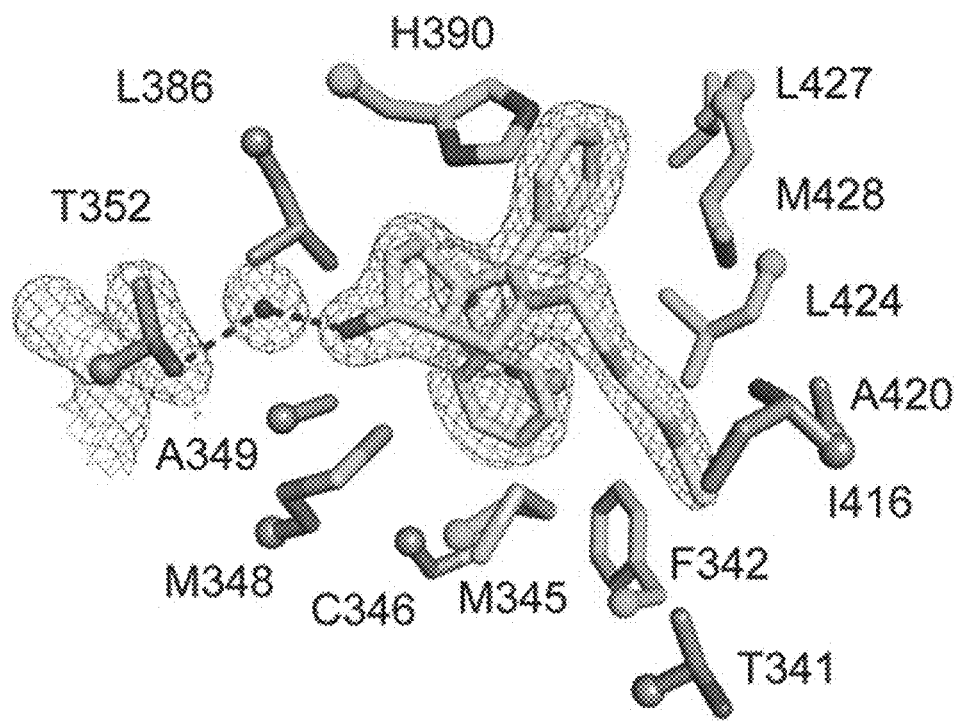
Figure 5B:
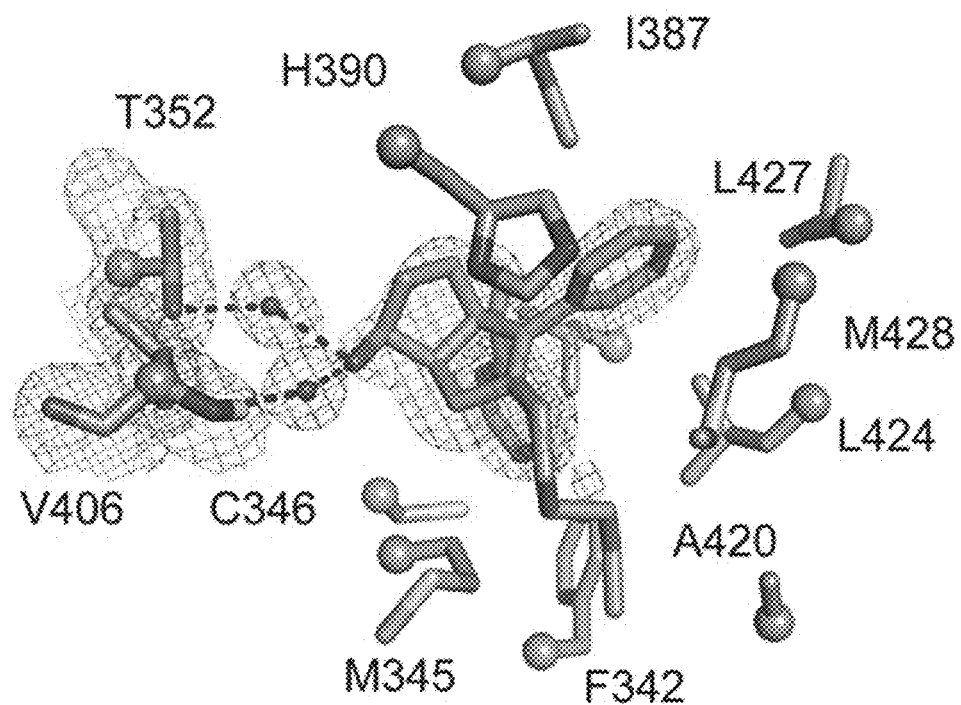

FIG. 5B shows a close-up views of the binding pockets from the structures of LRH-1 bound to SR-RJW100.

Figure 6A:
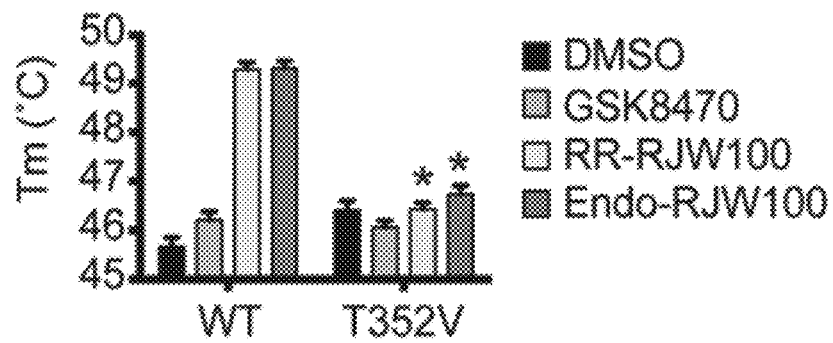

FIG. 6A shows data indicating the introduction of the T352V mutation to LRH-1 ablates the stabilizing effects of RR-RJW00 and endo-RJW100. Purified LRH-1 LBD, initially bound to DLPC for homogeneity, was incubated with either DMSO (control) or synthetic agonist dissolved in DMSO.

Figure 6B:
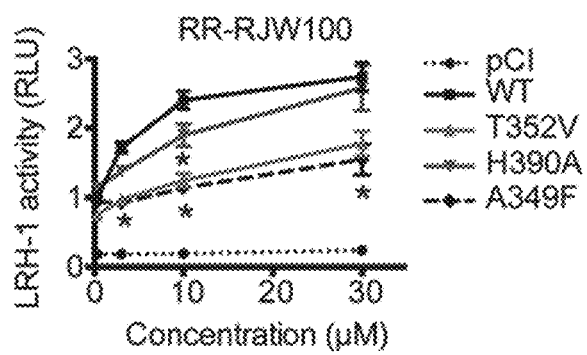

FIG. 6B shows data in luciferase reporter assays measuring LRH-1 activity, using the SHP-luc reporter. Values have been normalized to constitutive *Renilla* luciferase signal and are presented as fold change versus wild-type LRH-1+ DMSO. The A349F mutation introduces a bulky aromatic side chain, which blocks the binding pocket and prevents binding of synthetic ligands.

Figure 6C:
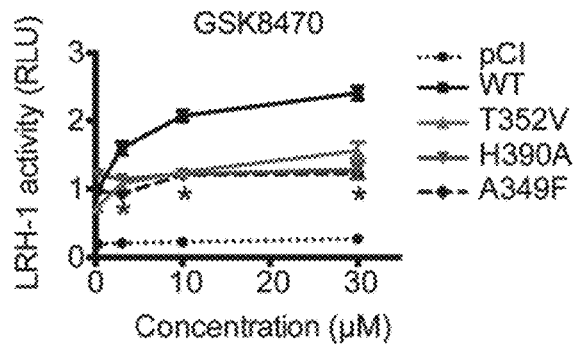

FIG. 6C shows data in luciferase reporter assays measuring LRH-1 activity, using the SHP-luc reporter.

Figure 6D:
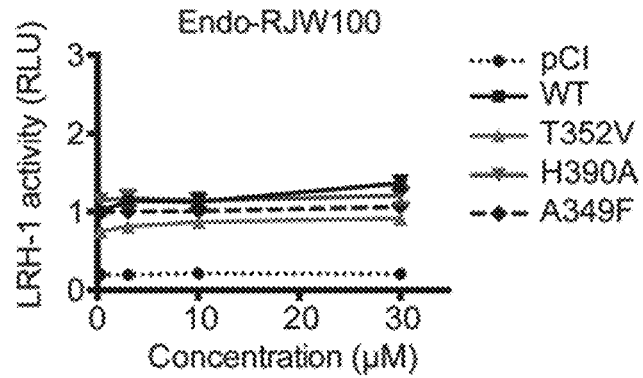

FIG. 6D shows data in luciferase reporter assays measuring LRH-1 activity, using the SHP-luc reporter.

Figure 7:
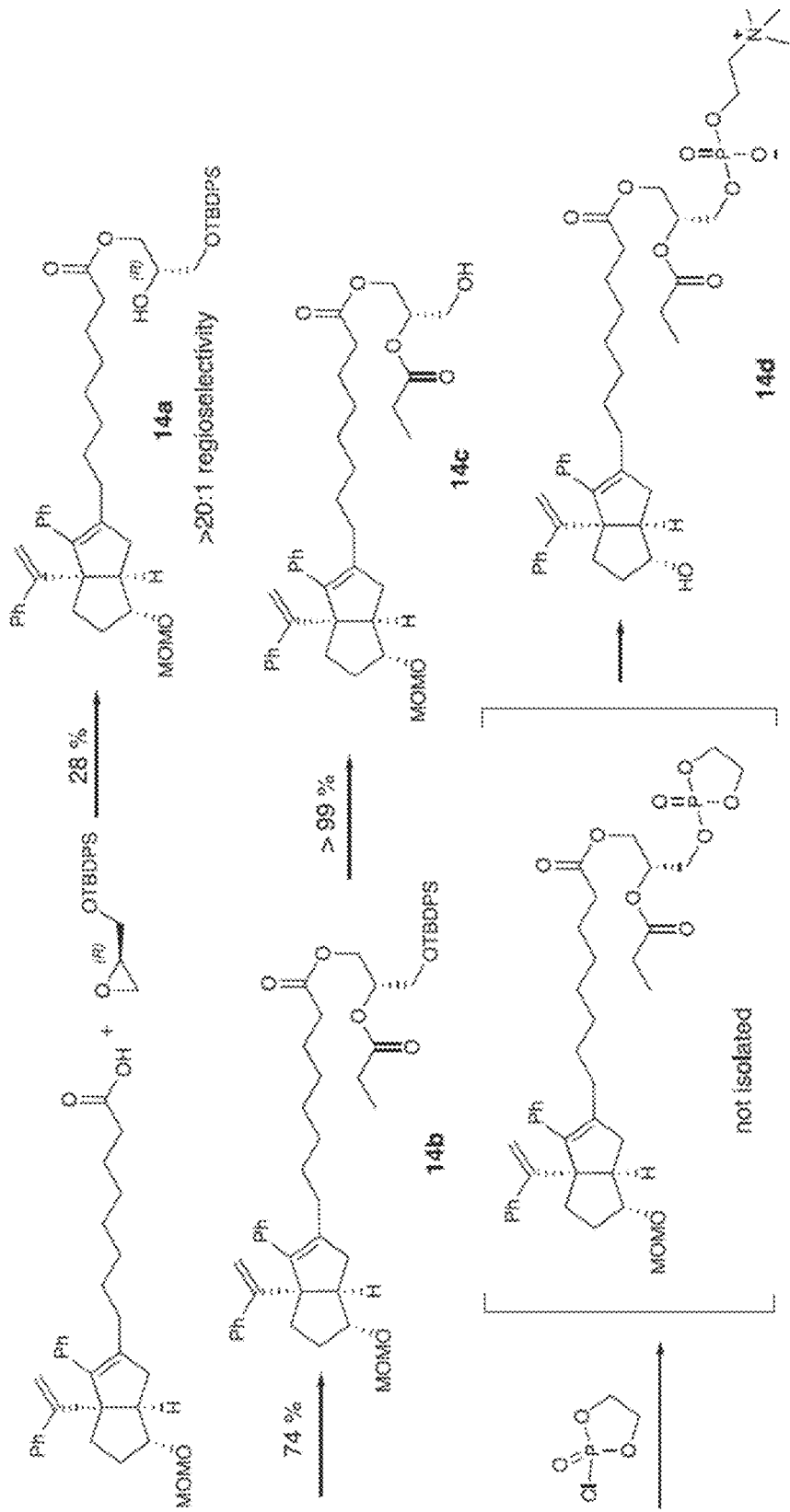

FIG. 7 shows a scheme for the production of compounds disclosed herein.

Figure 8:
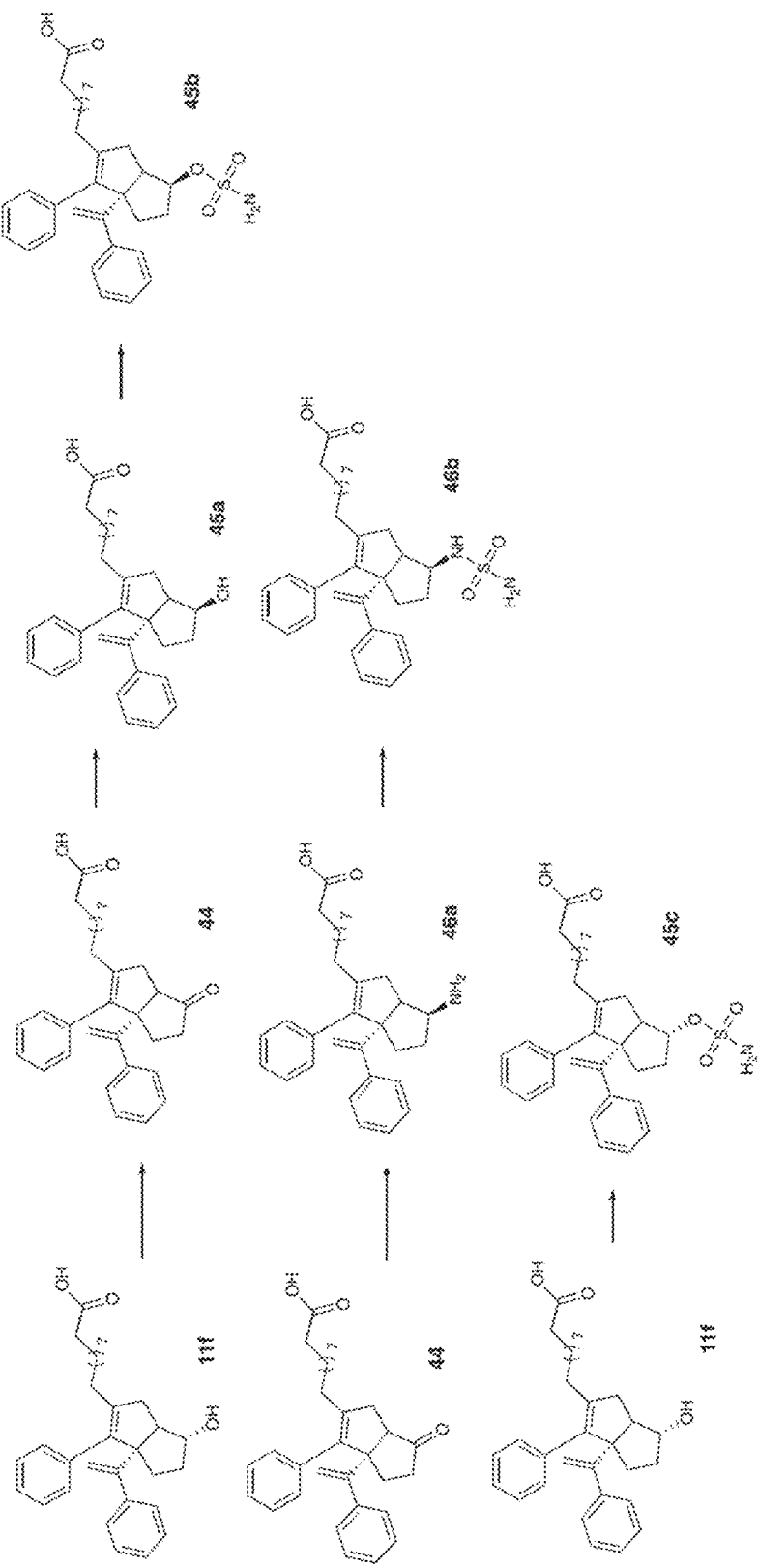

FIG. 8 shows schemes for the production of compounds disclosed herein.

DETAILED DISCUSSION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Certain of the compounds described herein may contain one or more asymmetric centers and may give rise to enantiomers, diastereomers, and other stereoisomeric forms that can be defined, in terms of absolute stereochemistry at each asymmetric atom, as (R)— or (S)—. The present chemical entities, pharmaceutical compositions and methods are meant to include all such possible isomers, including racemic mixtures, tautomer forms, hydrated forms, optically substantially pure forms and intermediate mixtures.

Unless otherwise stated, structures depicted herein are also meant to include compounds which differ only in the presence of one or more isotopically enriched atoms. For example, compounds having the present structures except for the replacement or enrichment of a hydrogen by deuterium or tritium at one or more atoms in the molecule, or the replacement or enrichment of a carbon by $^{13}C$ or $^{14}C$ at one or more atoms in the molecule, are within the scope of this disclosure. In one embodiment, provided herein are isotopically labeled compounds having one or more hydrogen atoms replaced by or enriched by deuterium. In one embodiment, provided herein are isotopically labeled compounds having one or more hydrogen atoms replaced by or enriched by tritium. In one embodiment, provided herein are isotopically labeled compounds having one or more carbon atoms replaced or enriched by $^{13}C$. In one embodiment, provided herein are isotopically labeled compounds having one or more carbon atoms replaced or enriched by $^{14}C$.

The disclosure also embraces isotopically labeled compounds that are identical to those recited herein, except that one or more atoms are replaced by an atom having an atomic mass or mass number different from the atomic mass or mass number usually found in nature. Examples of isotopes that can be incorporated into disclosed compounds include isotopes of hydrogen, carbon, nitrogen, oxygen, phosphorus, sulfur, fluorine, and chlorine, such as, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Certain isotopically labeled compounds (e.g., those labeled with $^{3}H$ and/or $^{14}C$) are useful in compound and/or substrate tissue distribution assays. Tritiated (i.e., $^{3}H$) and carbon-14 (i.e., $^{14}C$) isotopes can allow for ease of preparation and detectability. Further, substitution with heavier isotopes such as deuterium (i.e., $^{2}H$) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. In some embodiments, provided herein are compounds that can also contain unnatural proportions of atomic isotopes at one or more of atoms that constitute such compounds. All isotopic variations of the compounds as disclosed herein, whether radioactive or not, are encompassed within the scope of the present disclosure.

A "linking group" refers to any variety of molecular arrangements that can be used to bridge to molecular moieties together. An example formula may be —$R_m$— wherein R is selected individually and independently at each occurrence as: —$CR_mR_m$—, —$CHR_m$—, —CH—, —C—, —$CH_2$—, —$C(OH)R_m$, —C(OH)(OH)—, —C(OH)H, —$C(Hal)R_m$—, —C(Hal)(Hal)-, —C(Hal)H—, —$C(N_3)R_m$—, —$C(CN)R_m$—, —C(CN)(CN)—, —C(CN)H—, —$C(N_3)(N_3)$—, —$C(N_3)H$—, —O—, —S—, —N—, —NH—, —$NR_m$—, —(C=O)—, —(C=NH)—, —(C=S)—, —(C=$CH_2$)—, which may contain single, double, or triple bonds individually and independently between the R groups. If an R is branched with an $R_m$ it may be terminated with a group such as —$CH_3$, —H, —CH=$CH_2$, —CCH, —OH, —SH, —$NH_2$, —$N_3$, —CN, or -Hal, or two branched Rs may form a cyclic structure. It is contemplated that in certain instances, the total Rs or "m" may be less than 100, 50, 25, 10, 5, 4, or 3. Examples of linking groups in include bridging alkyl groups, alkoxyalkyl groups, and polyethylene glycol. The term "Hal" refers to a halogen.

As used herein, a "lipid" group refers to a hydrophobic group that is naturally or non-naturally occurring that is highly insoluble in water. As used herein a lipid group is considered highly insoluble in water when the point of connection on the lipid is replaced with a hydrogen and the resulting compound has a solubility of less than $3 \times 10^{-3}$ w/w (at 25° C.) in water, e.g., $9.5 \times 10^{-4}$% w/w (at 25° C.) which is the percent solubility of hexane in water by weight. See Solvent Recovery Handbook, $2^{nd}$ Ed, Smallwood, 2002 by Blackwell Science, page 193. Examples of naturally occurring lipids include saturated or unsaturated hydrocarbon chains found in fatty acids, glycerolipids, cholesterol, steroids, polyketides, and derivatives. Non-naturally occurring lipids include derivatives of naturally occurring lipids, acrylic polymers, and alkylated compounds and derivatives thereof.

As used herein, "alkyl" means a noncyclic straight chain or branched, unsaturated or saturated hydrocarbon such as those containing from 1 to 22 carbon atoms, while the term "lower alkyl" or "$C_{1-4}$alkyl" has the same meaning as alkyl but contains from 1 to 4 carbon atoms. The term "higher alkyl" has the same meaning as alkyl but contains from 8 to 22 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic. "Arylalkyl" means an alkyl substituted with an aryl, e.g., benzyl, methyl substituted with phenyl.

As used herein, "heteroaryl" refers to an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl sub stituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—$CH_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, propoxy, n-butoxy, s-butoxy, and t-butoxy.

"Alkylamino" refers to an alkyl group as defined above attached through an amino bridge. An example of an alkylamino is methylamino, (i.e., —NH—$CH_3$).

"Alkanoyl" refers to an alkyl as defined above attached through a carbonyl bride (i.e., —(C=O)alkyl).

"Alkylsulfonyl" refers to an alkyl as defined above attached through a sulfonyl bridge (i.e., —S(=O)$_2$alkyl) such as mesyl and the like, "arylsulfonyl" refers to an aryl attached through a sulfonyl bridge (i.e., —S(=O)$_2$aryl), and "aminosulfonyl" refers to an amino attached through a sulfonyl bridge (i.e., —S(=O)$_2$NH$_2$).

"Alkylsulfinyl" refers to an alkyl as defined above attached through a sulfinyl bridge (i.e. —S(=O)alkyl).

"Aminoalkyl" refers to an amino group attached through an alkyl bridge. An example of an aminoalkyl is aminomethyl, (i.e., NH$_2$—$CH_2$—).

"Hydroxyalkyl" refers to a hydroxy group attached through an alkyl bridge. An example of a hydroxyalkyl is hydroxyethyl, (i.e., HO—CH$_2$CH$_2$—).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO$_2$Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)$_2$ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral salts such as sodium, potassium, or zinc carboxylic acid salts, or organic acid salts of basic residues such as amines, alkylamines, or dialkylamines; alkali or organic salts of acidic residues such as carboxylic acids; and the like. In typical embodiments, the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers to any animal, preferably a human patient, livestock, rodent, monkey or domestic pet.

As used herein, the term "derivative" refers to a structurally similar compound that retains sufficient functional attributes of the identified analogue. The derivative may be structurally similar because it is lacking one or more atoms, substituted with one or more substituents, a salt, in different hydration/oxidation states, e.g., substituting a single or double bond, substituting a hydroxy group for a ketone, or because one or more atoms within the molecule are switched, such as, but not limited to, replacing an oxygen atom with a sulfur or nitrogen atom or replacing an amino group with a hydroxyl group or vice versa. Replacing a carbon with nitrogen in an aromatic ring is a contemplated derivative. The derivative may be a prodrug. Derivatives may be prepared by any variety of synthetic methods or appropriate adaptations presented in the chemical literature or as in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Typical prodrugs are pharmaceutically acceptable esters or enol ethers. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

For example, if a disclosed compound or a pharmaceutically acceptable form of the compound contains a carboxylic acid functional group, a prodrug can comprise a pharmaceutically acceptable ester formed by the replacement of the hydrogen atom of the acid group with a group such as ($C_1$-$C_8$)alkyl, ($C_2$-$C_{12}$)alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as beta-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

If a disclosed compound or a pharmaceutically acceptable form of the compound contains an alcohol functional group, a prodrug can be formed by the replacement of the hydrogen atom of the alcohol group with a group such as ($C_1$-$C_6$) alkanoyloxymethyl, 1-(($C_1$-$C_6$)alkanoyloxy) ethyl, 1-methyl-1(($C_1$-$C_6$)alkanoyloxy)ethyl ($C_1$-$C_6$)alkoxycarbonyloxymethyl, —N—($C_1$-$C_6$)alkoxycarbonylaminomethyl, succinoyl, ($C_1$-$C_6$)alkanoyl, alpha-amino($C_1$-$C_4$)alkanoyl, arylacyl and alpha-aminoacyl, or alpha-aminoacyl-alpha-aminoacyl, where each alpha-aminoacyl group is independently selected from naturally occurring L-amino acids P(O)(OH)$_2$, —P(O)(O($C_1$-$C_6$)alkyl)$_2$, and glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, a natural alpha-aminoacyl, —C(OH)C(O)OY$_1$ wherein Y$^1$ is H, ($C_1$-$C_6$)alkyl or benzyl, —C(OY$_2$)Y$_3$ wherein Y$_2$ is ($C_1$-$C_4$) alkyl and Y$_3$ is ($C_1$-$C_6$)alkyl, carboxy ($C_1$-$C_6$)alkyl, amino($C_1$-$C_4$)alkyl or mono-Nor di-N,N—($C_1$-$C_6$)alkylaminoalkyl, —C(Y$_4$)Y$_5$ wherein Y$_4$ is H or methyl and Y$_5$ is mono-N— or di-N,N—($C_1$-$C_6$)alkylamino, morpholino, piperidin-1-yl or pyrrolidin-1-yl.

As used herein, "pharmaceutically acceptable esters" include, but are not limited to, alkyl, alkenyl, alkynyl, aryl, arylalkyl, and cycloalkyl esters of acidic groups, including, but not limited to, carboxylic acids, phosphoric acids, phosphinic acids, sulfonic acids, sulfinic acids, and boronic acids.

As used herein, "pharmaceutically acceptable enol ethers" include, but are not limited to, derivatives of formula —C=C(OR) where R can be selected from alkyl, alkenyl, alkynyl, aryl, aralkyl, and cycloalkyl. Pharmaceutically acceptable enol esters include, but are not limited to, derivatives of formula —C=C(OC(O)R) where R can be selected from hydrogen, alkyl, alkenyl, alkynyl, aryl, aralkyl, and cycloalkyl.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others.

A "chemotherapy agent," "chemotherapeutic," "anti-cancer agent" or the like, refer to molecules that are recognized to aid in the treatment of a cancer. Contemplated examples include the following molecules or derivatives such as temozolomide, carmustine, bevacizumab, procarbazine, lomustine, vincristine, gefitinib, erlotinib, cisplatin, carboplatin, oxaliplatin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, vinblastine, vindesine, vinorelbine, paclitaxel, taxol, docetaxel, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorozole, exemestane, finasteride, marimastat, trastuzumab, cetuximab, dasatinib, imatinib, combretastatin, thalidomide, azacitidine, azathioprine, capecitabine, chlorambucil, cyclophosphamide, cytarabine, daunorubicin, doxifluridine, epothilone, irinotecan, mechlorethamine, mercaptopurine, mitoxantrone, pemetrexed, tioguanine, valrubicin and/or lenalidomide or combinations thereof such as cyclophosphamide, methotrexate, 5-fluorouracil (CMF); doxorubicin, cyclophosphamide (AC); mustine, vincristine, procarbazine, prednisolone (MOPP); sdriamycin, bleomycin, vinblastine, dacarbazine (ABVD); cyclophosphamide, doxorubicin, vincristine, prednisolone (CHOP); bleomycin, etoposide, cisplatin (BEP); epirubicin, cisplatin, 5-fluorouracil (ECF); epirubicin, cisplatin, capecitabine (ECX); methotrexate, vincristine, doxorubicin, cisplatin (MVAC).

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

Figure 1A:
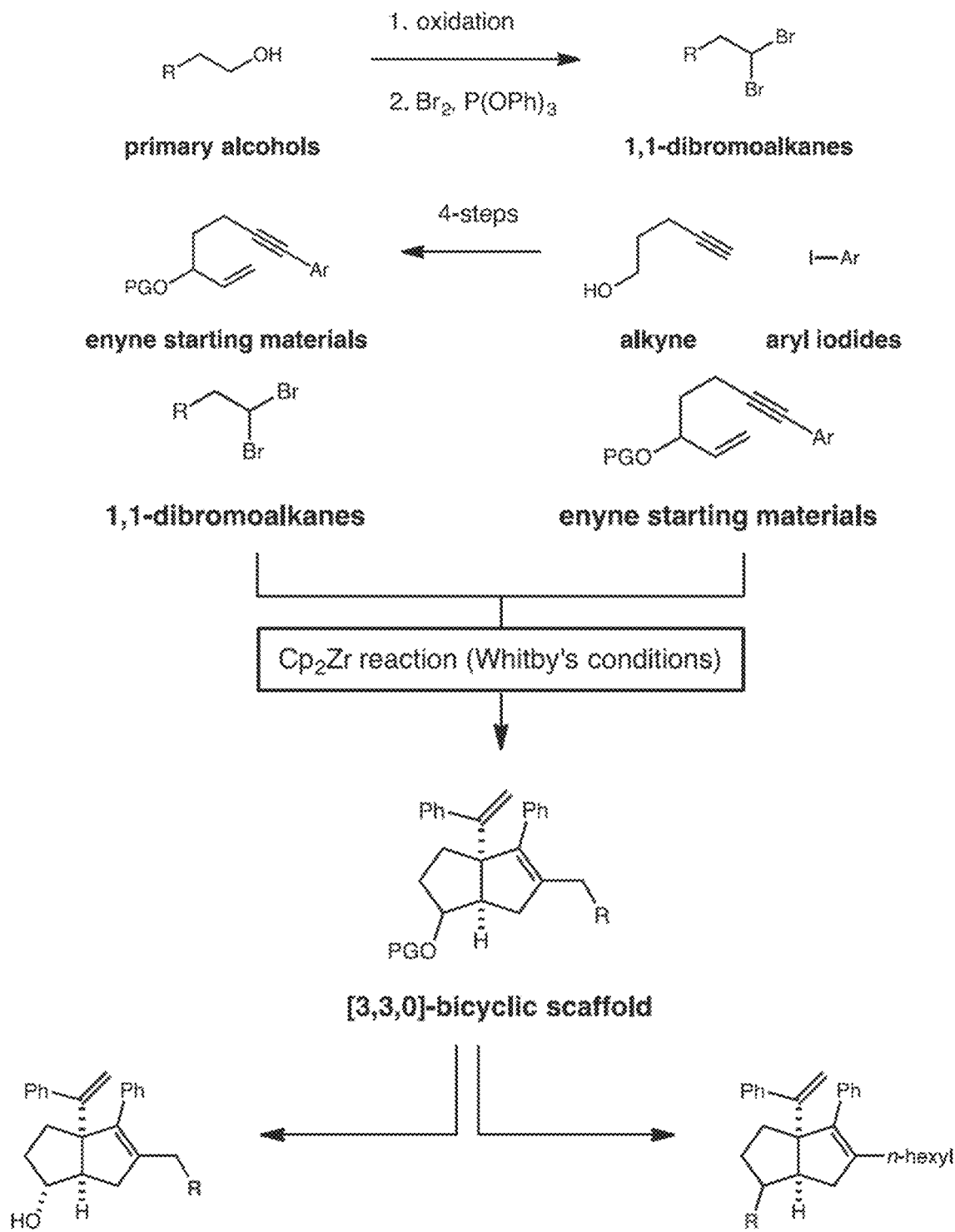
FIG. 1A shows a scheme for the production of compounds disclosed herein.
Figure 1B:
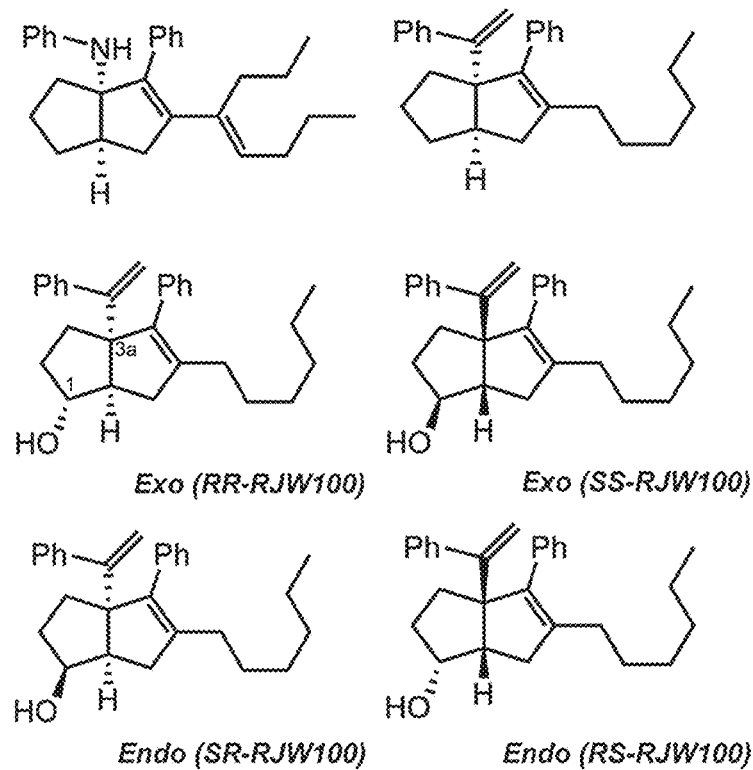
FIG. 1B illustrates additional embodiments of this disclosure. GSK8470 top left and top right, RJW100 analog lacking the hydroxyl group (named 18a).
Figure 1C:
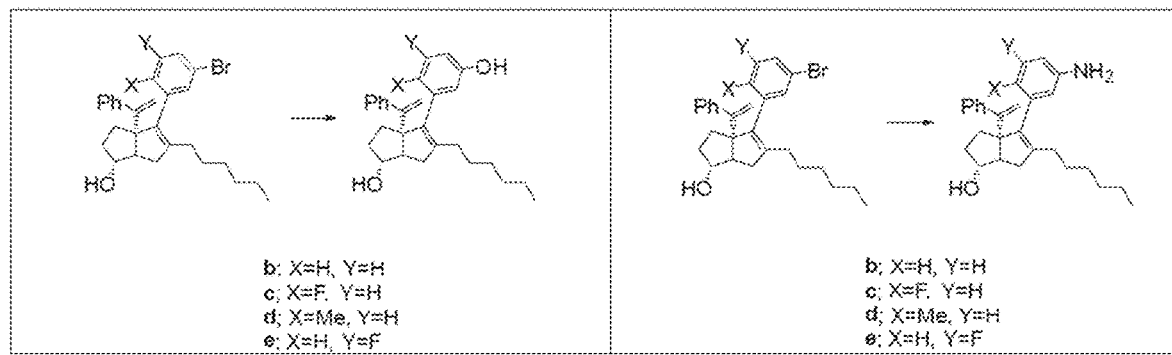
FIG. 1C shows a scheme for the production of compounds disclosed herein.

Crystal Structures of the Nuclear Receptor, Liver Receptor Homolog 1, Bound to Synthetic Agonists Reveal a Mechanism of Activation LRH-1 synthetic modulators are highly sought as pharmacological tools and as potential therapeutic agents. A detailed exploration of structural mechanisms governing regulation of LRH-1 by synthetic ligands was performed. See Mays et al., J Biol Chem, 2016, 291(49):25281-25291. Relative to the bacterial phospholipids (PL) LRH-1 agonist, dilauroylphosphatidyl choline (DLPC), the agonist (RR-RJW100) constricts the binding pocket and destabilizes portions of the activation function surface (AFS) (FIG. 1B). Stabilization of the AFS may facilitate co-activator binding, leading to greater potency or efficacy. Alternatively, analogs designed to enhance the AFS destabilization may be effective antagonists or inverse agonists. RJW100 was an effective derivative but modestly increased LRH-1 activation.

Crystal structure experiments reveals a different binding mode for RR-RJW100 compared with GSK8470 (FIG. 1B). Although this was surprising, it is not unreasonable, considering that LRH-1 has a very large hydrophobic binding pocket and that these agonists are also quite hydrophobic, filling only 37% of the available space (excluding waters). It is possible that many of the GSK8470 analogs investigated in the previous structure-activity relationship study adopt a variety of different conformations. This seems to be the case in our docking studies with these ligands; multiple very different binding modes with similar energies are predicted. Importantly, however, the repositioning of RR-RJW100 in our structure appears to be driven by particular interactions, because SR-RJW100 assumes a very similar pose (FIG. 1B). This occurs despite the fact that the SR derivative exhibits signs of motion in our crystal structure, with significant disorder in the tail of the ligand and higher relative B-factors than RR-RJW100.

A major factor driving repositioning of the RJW100 isomers was the hydrogen bonding interaction made by the hydroxyl group. Although the contact with residue Thr-352 is indirect, it is mediated by a water molecule. The existence of conserved water molecules, as well as their participation in ligand binding, has been described. Thus, this interaction could serve as an anchor point to secure the compound in a predictable orientation, enabling the targeting of desired parts of the binding pocket via strategic addition of substituents to the ligand's scaffold. Moreover, replacing the RJW100 hydroxyl group with a larger polar moiety may allow direct contact with Thr-352, leading to a stronger interaction.

The role of the Thr-352 interaction in LRH-1 activation by RR-RJW100 was demonstrated through the marked loss of activation by this compound when this residue was mutated. In addition, an RJW100 analog lacking a hydroxyl group was a poor activator. Unexpectedly, the T352V mutation also resulted in a loss of activity for GSK8470, although this compound does not interact with the Thr-352-coordinated water molecule. However, we show that the T352V mutation weakens GSK8470's interaction with His-390, perhaps via destabilization of the conserved water network. This could be responsible for the loss of activity of GSK8470 when Thr-352 is mutated.

Studies indicate that the interaction of small molecule agonists with LRH-1 is complex. Not only do these agonists affect receptor conformation differently from PL ligands, but they also exhibit an unexpected variability in binding modes.

Hexahydropentalene Derivatives

In certain embodiments, this disclosure relates to compounds that are hexahydropentalene derivatives. In certain embodiments, the hexahydropentalene derivatives are any of the compounds disclosed herein optionally substituted with one or more substituents. In certain embodiments, the compounds have the following formula:

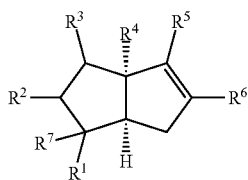

Formula I including prodrugs, or salts thereof wherein, $R^1$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, benozyl, benzyl, aryl, or heterocyclyl, wherein $R^1$ is optionally substituted with one or more, the same or different, $R^{10}$;

$R^2$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkylsulfonyl, aryl sulfonyl, carbocyclyl, benozyl, benzyl, aryl, or heterocyclyl, wherein $R^2$ is optionally substituted with one or more, the same or different, $R^{10}$;

$R^3$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, benozyl, benzyl, aryl, or heterocyclyl, wherein $R^3$ is optionally substituted with one or more, the same or different, $R^{10}$;

$R^4$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, benozyl, benzyl, aryl, or heterocyclyl, wherein $R^4$ is optionally substituted with one or more, the same or different, $R^{10}$;

$R^5$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, benozyl, benzyl, aryl, or heterocyclyl, wherein $R^5$ is optionally substituted with one or more, the same or different, $R^{10}$;

$R^6$ is a lipid or alkyl wherein $R^6$ is optionally terminally substituted with a hydroxy, carboxy, or phosphate, wherein the hydroxy, carboxy, or phosphate are optionally further substituted with $R^{10}$;

$R^7$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkyl sulfonyl, aryl sulfonyl, carbocyclyl, benozyl, benzyl, aryl, or heterocyclyl, wherein $R^7$ is optionally substituted with one or more, the same or different, $R^{10}$; or $R^1$ and $R^7$ together are an oxo or oxime, wherein the oxime is optionally substituted with one or more, the same or different, $R^{10}$;

$R^{11}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkyl sulfonyl, arylsulfonyl, aminosulfonyl, carbocyclyl, benozyl, benzyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydroxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methyl carbamoyl, N-ethyl carbamoyl, N,N-dimethylcarbamoyl, N,N-diethylcarbamoyl, N-methyl-N-ethylcarbamoyl, methylthio, ethylthio, methyl sulfinyl, ethylsulfinyl, mesyl, ethyl sulfonyl, methoxycarbonyl, ethoxycarbonyl, isopropoxycarbonyl, tert-butoxycarbonyl, N-methyl sulfamoyl, N-ethyl sulfamoyl, N,N-dimethylsulfamoyl, N,N-diethylsulfamoyl, N-methyl-N-ethylsulfamoyl, benozyl, benzyl, carbocyclyl, aryl, or heterocyclyl.

In certain embodiments, $R^2$ and $R^3$ are hydrogen, $R^4$ is 1-phenylvinyl or 1-phenylethyl, and $R^5$ is phenyl.

In certain embodiments, $R^6$ is alkyl terminally substituted with a hydroxy, carboxy, or phosphate, wherein the hydroxy, carboxy, or phosphate are optionally further substituted with $R^{10}$.

In certain embodiments, compounds have one of the following formula

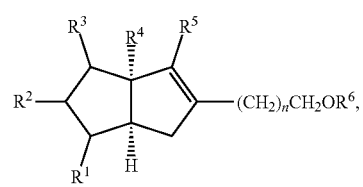

Formula IA

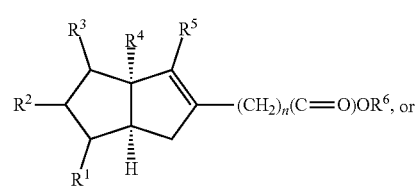

Formula IB

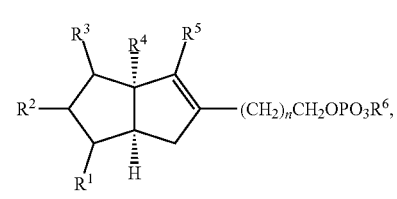

Formula IC wherein $R^6$ is hydrogen, alkyl, or alkanoyl optionally substituted with $R^{10}$.

In certain embodiments, $R^1$ is hydroxyl, alkyl, amino, aminoalkyl, carbamoyl, sulphate, sulfonate, aminosulfonyl, phosphate, phosphonate, or heterocyclyl, wherein $R^1$ is optionally substituted with $R^{10}$.

In certain embodiments, $R^1$ is thiazolidinedione or triazole.

In certain embodiments, compounds have one of the following formula:

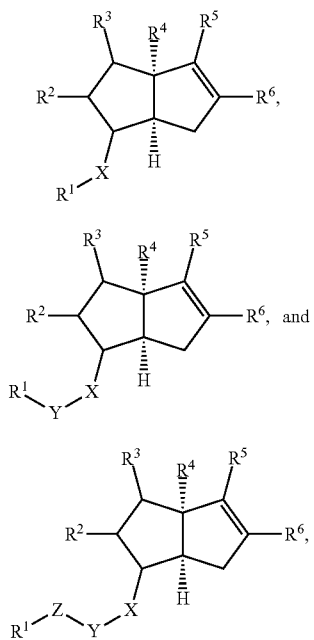

Formula ID

Formula IE

Formula IF wherein,

X is a linking group, —$CH_2$—, —C(OH)(OH)—, —C(OH)H, —C(Hal)(Hal)-, —C(Hal)H—, —O—, —S—, —(S=O)—, —$SO_2$—, —NH—, —(C=O)—, —(C=NH)—, or —(C=S)—;

Y is —$CH_2$—, —C(OH)(OH)—, —C(OH)H, —C(Hal)(Hal)-, —C(Hal)H—, —O—, —S—, —(S=O)—, —$SO_2$—, —NH—, —(C=O)—, —(C=NH)—, or —(C=S)—;

Z is —$CH_2$—, —C(OH)(OH)—, —C(OH)H, —C(Hal)(Hal)-, —C(Hal)H—, —O—, —S—, —(S=O)—, —$SO_2$—, —NH—, —(C=O)—, —(C=NH)—, or —(C=S)—; and $R^1$ is hydrogen, hydroxy, alkyl, alkanoyl, amino, aminoalkyl, carbamoyl, sulfate, sulfonate, aminosulfonyl, phosphate, phosphonate, or heterocyclyl.

In certain embodiments, X, Y, Z, and $R^1$ may be:
a) X is O, and $R^1$ is alkanoyl;
b) X is —NH—, and $R^1$ is alkanoyl;
c) X is O, and $R^1$ is aminosulfonyl;
d) X is —NH—, and $R^1$ is aminosulfonyl;
e) X is —(C=O)—, $R^1$ is amino;
f) X is O, Y is —(C=O)—, $R^1$ is amino;
g) X is O, Y is —(C=O)—, Z is —NH—, and $R^1$ is sulfonate; and
h) X is O, Y is —(C=O)—, Z is —NH—, and $R^1$ is aminosulfonyl.

In certain embodiments, $R^7$ is hydroxyl or alkoxy, wherein $R^7$ is optionally substituted with one or more, the same or different, $R^{10}$.

In certain embodiments, the compounds have the following formula:

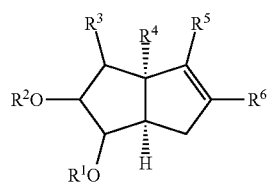

Formula II including prodrugs, or salts thereof wherein, $R^1$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, aryl sulfonyl, carbocyclyl, benozyl, benzyl, aryl, or heterocyclyl, wherein $R^1$ is optionally substituted with one or more, the same or different, $R^{10}$;

$R^2$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkylsulfonyl, aryl sulfonyl, carbocyclyl, benozyl, benzyl, aryl, or heterocyclyl, wherein $R^2$ is optionally substituted with one or more, the same or different, $R^{10}$;

$R^3$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkylsulfonyl, aryl sulfonyl, carbocyclyl, benozyl, benzyl, aryl, or heterocyclyl, wherein $R^3$ is optionally substituted with one or more, the same or different, $R^{10}$;

$R^4$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, benozyl, benzyl, aryl, or heterocyclyl, wherein $R^4$ is optionally substituted with one or more, the same or different, $R^{10}$;

$R^5$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, benozyl, benzyl, aryl, or heterocyclyl, wherein $R^5$ is optionally substituted with one or more, the same or different, $R^{10}$;

$R^6$ is a lipid or alkyl wherein $R^6$ is optionally terminally substituted with a hydroxy, carboxy, or phosphate, wherein the hydroxy, carboxy, or phosphate are optionally further substituted with $R^{10}$;

$R^7$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, aryl sulfonyl, carbocyclyl, benozyl, benzyl, aryl, or heterocyclyl, wherein $R^7$ is optionally substituted with one or more, the same or different, $R^{10}$; or $R^1$ and $R^7$ together are an oxo or oxime, wherein the oxime is optionally substituted with one or more, the same or different, $R^{10}$;

$R^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, arylsulfonyl, aminosulfonyl, carbocyclyl, benozyl, benzyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydroxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methyl carbamoyl, N-ethyl carbamoyl, N,N-dim ethyl carbamoyl, N,N-diethylcarbamoyl, N-methyl-N-ethylcarbamoyl, methylthio, ethylthio, methyl sulfinyl, ethyl sulfinyl, mesyl, ethyl sulfonyl, methoxycarbonyl, ethoxycarbonyl, isopropoxycarbonyl, tert-butoxycarbonyl, N-methyl sulfamoyl, N-ethyl sulfamoyl, N,N-dimethylsulfamoyl, N,N-diethyl sulfamoyl, N-methyl-N-ethylsulfamoyl, benozyl, benzyl, carbocyclyl, aryl, or heterocyclyl.

$R^4$ is 1-phenylvinyl or 1-phenylethyl, and $R^5$ is phenyl optionally substituted.

In certain embodiments, $R^6$ is alkyl terminally substituted with a hydroxy, carboxy, or phosphate, wherein the hydroxy, carboxy, or phosphate are optionally further substituted with $R^{10}$.

Methods of Use

In certain embodiments, this disclosure relates to methods of treating or preventing diseases or conditions associated with LRH-1 such as diabetes, cancer, or cardiovascular disease by administering an effective amount of a hexahydropentalene derivative disclosed herein to a subject in need thereof.

In certain embodiments, the disclosure relates to methods of treating or preventing diabetes comprising administering an effective amount of a pharmaceutical composition comprising compounds disclosed herein to a subject in need thereof. In certain embodiments, the subject is at risk of, exhibiting symptoms of, or diagnosed with diabetes, insulin-dependent diabetes mellitus, non insulin-dependent diabetes mellitus, or gestational diabetes.

In certain embodiments, this disclosure relates to compounds disclosed herein that are LRH-1 agonists for use in the prevention of progressive loss of pancreatic beta-cells. It also relates to an LRH-1 agonist for use in the preservation or restoration of pancreatic beta-cells. Further, it relates to an LRH-1 agonist for use in the prevention or treatment of type I diabetes or insulin-dependent diabetes mellitus, the increment of survival of pancreatic beta-cells, the increment of the performance of pancreatic beta-cells, the increment of the survival of a beta-cell graft, the in vitro preservation of pancreatic beta-cells, maintaining insulin secretion and/or in a method of transplanting pancreatic islet cells.

Diabetes mellitus (DM) is often simply referred to as diabetes. Diabetes is a condition in which a person has a high blood sugar (glucose) level as a result of the body either not producing enough insulin, or because body cells do not properly respond to the insulin that is produced.

In healthy persons, blood glucose levels are maintained within a narrow range, primarily by the actions of the hormone insulin. Insulin is released by pancreatic beta-cells at an appropriate rate in response to circulating glucose concentrations, the response being modulated by other factors including other circulating nutrients, islet innervation and incretin hormones. Insulin maintains glucose concentrations by constraining the rate of hepatic glucose release to match the rate of glucose clearance.

Insulin thus enables body cells to absorb glucose, to turn into energy. If the body cells do not absorb the glucose, the glucose accumulates in the blood (hyperglycemia), leading to various potential medical complications. Accordingly, diabetes is characterized by increased blood glucose resulting in secondary complications such as cardiovascular diseases, kidney failure, retinopathy and neuropathy if not properly controlled. Two major pathophysiologies are related to increase glycemia. The first is an autoimmune attack against the pancreatic insulin-producing beta-cells (Type 1 diabetes or insulin-dependent diabetes) whilst the second is associated to poor beta-cell function and increased peripheral insulin resistance (Type 2 diabetes or non-insulin dependent diabetes). Similar to Type 1, beta-cell death is also observed in Type 2 diabetes. Type 1 and often Type 2 diabetes requires the person to inject insulin.

Type 1 DM is typically characterized by loss of the insulin-producing beta-cells of the islets of Langerhans in the pancreas leading to insulin deficiency. This type of diabetes can be further classified as immune-mediated or idiopathic. The majority of Type 1 diabetes is of the immune-mediated nature, where beta-cell loss is a T-cell mediated autoimmune attack. Sensitivity and responsiveness to insulin are usually normal, especially in the early stages. Type 1 diabetes can affect children or adults but was traditionally termed "juvenile diabetes" because it represents a majority of the diabetes cases in children.

Type 2 DM is characterized by beta-cell dysfunction in combination with insulin resistance. The defective responsiveness of body tissues to insulin is believed to involve the insulin receptor. Similar to Type 1 diabetes an insufficient beta cell mass is also a pathogenic factor in many Type 2 diabetic patients. In the early stage of Type 2 diabetes, hyperglycemia can be reversed by a variety of measures and medications that improve insulin secretion and reduce glucose production by the liver. As the disease progresses, the impairment of insulin secretion occurs, and therapeutic replacement of insulin may sometimes become necessary in certain patients. In certain embodiments, the treatment of diabetes by administering compounds disclosed herein is in combination with the administration of insulin.

Diabetes without proper treatments can cause many complications. Acute complications include hyperglycaemia, diabetic ketoacidosis, or nonketotic hyperosmolar coma. Serious long-term complications include cardiovascular disease, chronic renal failure, retinal damage.

In certain embodiments, this disclosure relates to methods of treating or preventing cardiovascular disease comprising administering an effective amount of a pharmaceutical composition comprising a compound disclosed herein to a subject in need thereof.

In certain embodiments, the cardiovascular disease is coronary artery diseases (CAD), angina, myocardial infarction, stroke, hypertensive heart disease, rheumatic heart disease, cardiomyopathy, heart arrhythmia, congenital heart disease, valvular heart disease, carditis, aortic aneurysms, peripheral artery disease, and venous thrombosis.

In certain embodiments, this disclosure relates to methods of managing cancer. In certain embodiments, this disclosure relates to methods of treating cancer comprising administering an effective amount of an agent to a subject in need thereof. In certain embodiments, the cancer is pancreatic cancer, breast cancer, liver cancer, colon cancer, or gastrointestinal tumors.

Benod et al. report LRH-1 regulates pancreatic cancer cell growth and proliferation. Proc Natl Acad Sci USA, 2011, 108(41):16927-31. Pan et al. report LRH-1-dependent programming of mitochondrial glutamine processing drives liver cancer. Genes Dev, 2016, 30(11): 1255-1260. Holly et al. LRH-1 drives colon cancer cell growth by repressing the expression of the CDKN1A gene in a p53-dependent manner. Nucleic Acids Res, 2016, 44(2): 582-594.

In certain embodiments, the cancer is selected from bladder cancer, breast cancer, colon cancer, rectal cancer, endometrial cancer, kidney cancer, leukemia, lung cancer, melanoma, non-Hodgkin lymphoma, pancreatic cancer, prostate cancer, and thyroid cancer.

The compounds disclosed herein can be used alone in the treatment of each of the foregoing conditions or can be used to provide additive or potentially synergistic effects with certain existing chemotherapies, radiation, biological or immunotherapeutics (including monoclonal antibodies) and vaccines. The compounds disclosed herein may be useful for restoring effectiveness of certain existing chemotherapies and radiation and or increasing sensitivity to certain existing chemotherapies and/or radiation.

Coste et al. report LRH-1-mediated glucocorticoid synthesis in enterocytes protects against inflammatory bowel disease. PNAS, 2007. 104 (32) 13098-13103. See also Fernandez-Marcos et al. Emerging actions of the nuclear receptor LRH-1 in the gut, Biochim Biophys Acta. 2011 August; 1812(8): 947-955. Mueller et al. The nuclear receptor LRH-1 critically regulates extra-adrenal glucocorticoid synthesis in the intestine, Journal of Experimental Medicine September 2006, 203 (9) 2057-2062.

Thus, in certain embodiments, this disclosure relates to methods to prevent or treat gut, intestinal, and colonic inflammation, comprising administrating a compound disclosed herein in an effective amount to a subject in need thereof. In certain embodiments, the subject is at risk of, exhibiting symptoms of, or diagnosed with intestinal and colonic inflammation.

In another aspect, the disclosure relates to methods to prevent or treat inflammatory bowel diseases (IBD), comprising administrating a compound disclosed herein in an effective amount to a subject in need thereof. In certain embodiments, the subject is at risk of, exhibiting symptoms of, or diagnosed with inflammatory bowel diseases (IBD).

In another aspect, the disclosure relates to methods to prevent or treat Crohn's disease, comprising administrating a compound disclosed herein in an effective amount to a subject in need thereof. In certain embodiments, the subject is at risk of, exhibiting symptoms of, or diagnosed with Crohn's disease.

In another aspect, the disclosure relates to methods to prevent or treat colitis or ulcerative colitis, comprising administrating a compound disclosed herein in an effective amount to a subject in need thereof. In certain embodiments, the subject is at risk of, exhibiting symptoms of, or diagnosed with colitis or ulcerative colitis.

Overweight and obesity are increasingly common conditions in the world. Doctors measure body mass index (BMI) to screen for obesity. Obesity is a serious medical condition that can cause complications such as metabolic syndrome, high blood pressure, atherosclerosis, heart disease, diabetes, high serum cholesterol, cancers and sleep disorders. Thus, there is a need to reduce obesity.

Fatty liver, or hepatic steatosis, is a term that describes the buildup of fat in the liver. Excessive alcohol use causes fat to accumulate, damages the liver, and cirrhosis may develop. Nonalcoholic fatty liver disease (NAFLD) is a fatty liver disease associated with obesity-related disorders, such as type-2 diabetes and metabolic syndrome, occurring in people who drink little or no alcohol. Nonalcoholic steatohepatitis (NASH) is a more advanced and severe subtype of NAFLD where steatosis is complicated by liver-cell injury and inflammation, with or without fibrosis. NASH can be severe and can lead to cirrhosis, in which the liver is permanently damaged and scarred and no longer able to work properly. Insulin resistance, altered lipid storage and metabolism, accumulation of cholesterol within the liver, oxidative stress resulting in increased hepatic injury, and bacterial translocation secondary to disruption of gut microbiota have all been implicated as important co-factors contributing to progression of NASH. Due to the growing epidemic of obesity and diabetes, NASH is projected to become the most common cause of advanced liver disease and the most common indication for liver transplantation.

Lee et al. report dilauroyl phosphatidylcholine (DLPC) is an LRH-1 agonist ligand in vitro. DLPC treatment induces bile acid biosynthetic enzymes in mouse liver, increases bile acid levels, and lowers hepatic triglycerides and serum glucose. DLPC treatment also decreases hepatic steatosis and improves glucose homeostasis in two mouse models of insulin resistance. Nature volume 474, pages 506-510 (2011). Sahini et al. report differentially expressed genes (DEGs) were identified which are mechanistically linked to lipid droplet (LD) formation in hepatocytes. LD-associated DEGs frequently regulated in patient samples were identified. Liver-receptor homolog-1 (NR5A2), was commonly repressed among patients examined. Translational Research, 177: 41-69 (2016).

In certain embodiments, this disclosure relates to methods to prevent or treat hepatic steatosis or metabolic syndrome, comprising administrating compounds disclosed herein in an effective amount to a subject in need thereof. In certain embodiments, the subject is at risk of, exhibiting symptoms of, or diagnosed with nonalcoholic fatty liver disease (NAFLD). In certain embodiments, the subject is at risk of, exhibiting symptoms of, or diagnosed with nonalcoholic steatohepatitis (NASH). In certain embodiments, the subject is at risk of, exhibiting symptoms of, or diagnosed with alcoholic liver disease (ALD). In certain embodiments, the subject is at risk of, exhibiting symptoms of, or diagnosed with alcoholic steatohepatitis (ASH).

In certain embodiments, a subject is at risk of NAFLD due to obesity, insulin resistance, an enlarged liver, signs of cirrhosis, or abnormal levels of liver enzymes, triglycerides and/or cholesterol. Signs of insulin resistance include darkened skin patches over your knuckles, elbows, and knees. Signs of cirrhosis include jaundice, a condition that causes your skin and whites of your eyes to turn yellow. A sign of NAFLD or NASH includes blood test showing increased levels of the liver enzymes alanine aminotransferase (ALT) and aspartate aminotransferase (AST). An enlarged liver or an abnormal amount of fat in a liver may be identified by ultrasound, computerized tomography (CT) scans, magnetic resonance imaging or combinations thereof. A liver biopsy may be used to detect liver inflammation and damage to diagnose NASH.

Metabolic syndrome is typically diagnosed in the presence of three or more of the following medical issues: large waste size, e.g., 40 inches or more, high triglycerides e.g., triglyceride level of 150 mg/dL or higher, low levels of HDL cholesterol less than 50 mg/dL, high blood pressure, e.g., 130/85 mmHg or higher, and high blood glucose (or blood sugar) levels, a fasting blood sugar level of 100 mg/dL or higher.

In another aspect, the disclosure relates to methods to control or reduce the serum cholesterol level, comprising administrating compounds disclosed herein in an effective amount to a subject in need thereof. In certain embodiments, the subject has a borderline high serum cholesterol level, 200-239 mg/dL. In certain embodiments, the subject has a high serum cholesterol level, >240 mg/dL. In certain embodiments, the subject is at risk of, exhibiting symptoms, or diagnosed with hypercholesterolemia.

In another aspect, the disclosure relates to methods to prevent or treat hepatic steatosis, comprising administrating a compound disclosed herein in an effective amount to a subject in need thereof. In certain embodiments, the subject is at risk of, exhibiting symptoms of, or diagnosed with alcoholic liver disease (ALD). In certain embodiments, the subject is at risk of, exhibiting symptoms of, or diagnosed with alcoholic steatohepatitis (ASH). In certain embodiments, the subject is at risk of, exhibiting symptoms of, or diagnosed with nonalcoholic fatty liver disease (NAFLD). In certain embodiments, the subject is at risk of, exhibiting symptoms of, or diagnosed with nonalcoholic steatohepatitis (NASH). In certain embodiments, a subject is at risk of NAFLD due to obesity, insulin resistance, an enlarged liver, signs of cirrhosis, or abnormal levels of liver enzymes, triglycerides and/or cholesterol. Signs of insulin resistance include darkened skin patches over your knuckles, elbows, and knees. Signs of cirrhosis include jaundice, a condition that causes your skin and whites of your eyes to turn yellow. A sign of NAFLD or NASH includes blood test showing increased levels of the liver enzymes alanine aminotransferase (ALT) and aspartate aminotransferase (AST). An enlarged liver or an abnormal amount of fat in a liver may be identified by ultrasound, computerized tomography (CT) scans, magnetic resonance imaging or combinations thereof. A liver biopsy may be used to detect liver inflammation and damage to diagnose NASH.

The precise therapeutically effective amount of the compounds of this disclosure will depend on a number of factors. There are variables inherent to the compounds including, but not limited to, the following: molecular weight, absorption, bioavailability, distribution in the body, tissue penetration, half-life, metabolism, protein binding, and excretion. These variables determine what dose of compound needs to be administered in a sufficient percentage and for a sufficient amount of time to have the desired effect on the condition being treated (e.g., neoplasm). The duration of drug exposure will be limited only by the compound half-life, and side effects from treatment requiring cessation of dosing. The amount of compound administered will also depend on factors related to patients and disease including, but not limited to, the following: the age, weight, concomitant medications and medical condition of the subject being treated, the precise condition requiring treatment and its severity, the nature of the formulation, and the route of administration. Ultimately the dose will be at the discretion of the attendant physician or veterinarian. Typically, the compound disclosed herein will be given for treatment in the range of 0.01 to 30 mg/kg body weight of recipient (mammal) per day or per dose or per cycle of treatment and more usually in the range of 0.1 to 10 mg/kg body weight per day or per dose or per cycle of treatment. Thus, for an adult human being treated for a condition, the actual amount per day or per dose or per cycle of treatment would usually be from 1 to 2000 mg and this amount may be given in a single or multiple doses per day or per dose or per cycle of treatment. Dosing regimens may vary significantly and will be determined and altered based on clinical experience with the compound. The full spectrum of dosing regimens may be employed ranging from continuous dosing (with daily doses) to intermittent dosing. A therapeutically effective amount of a pharmaceutically acceptable salt of a compound disclosed herein may be determined as a proportion of the therapeutically effective amount of the compound as the free base.

Pharmaceutical Compositions

While it is possible that, for use in therapy, a therapeutically effective amount of a compound disclosed herein may be administered as the raw chemical, it is typically presented as the active ingredient of a pharmaceutical composition or formulation. Accordingly, the disclosure further provides a pharmaceutical composition comprising a compound disclosed herein. The pharmaceutical composition may further comprise one or more pharmaceutically acceptable carriers, diluents, and/or excipients. The carrier(s), diluent(s) and/or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound disclosed herein with one or more pharmaceutically acceptable carriers, diluents and/ or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound disclosed herein (as a free-base, solvate (including hydrate) or salt, in any form), depending on the condition being treated, the route of administration, and the age, weight and condition of the patient. Preferred unit dosage formulations are those containing a daily dose, weekly dose, monthly dose, a sub-dose or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including capsules, tablets, liquid-filled capsules, disintegrating tablets, immediate, delayed and controlled release tablets, oral strips, solutions, syrups, buccal and sublingual), rectal, nasal, inhalation, topical (including transdermal), vaginal or parenteral (including subcutaneous, intramuscular, intravenous or intradermal) route. Such formulations may be prepared by any method known in the art of pharmacy, for example by bringing into association the active ingredient with the carrier(s), excipient(s) or diluent. Generally, the carrier, excipient or diluent employed in the pharmaceutical formulation is "non-toxic," meaning that it/they is/are deemed safe for consumption in the amount delivered in the pharmaceutical composition, and "inert" meaning that it/they does/do not appreciably react with or result in an undesired effect on the therapeutic activity of the active ingredient.

Pharmaceutical formulations adapted for oral administration may be presented as discrete units such as liquid-filled or solid capsules; immediate, delayed or controlled release tablets; powders or granules; solutions or suspensions in aqueous or non-aqueous liquids; edible foams or whips; oil-in-water liquid emulsions, water-in-oil liquid emulsions or oral strips, such as impregnated gel strips.

For instance, for oral administration in the form of a tablet or capsule, the active drug component can be combined with an oral pharmaceutically acceptable carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Solid capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds disclosed herein can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Solutions and syrups can be prepared by dissolving the compound in a suitably flavored aqueous solution, while elixirs are prepared through the use of a pharmaceutically acceptable alcoholic vehicle. Suspensions can be formulated by dispersing the compound in a pharmaceutically acceptable vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, unit dosage formulations for oral administration can be microencapsulated. The formulation can also be prepared to prolong or sustain the release as for example by coating or embedding particulate material in polymers, wax or the like.

The compounds of the disclosure can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered dose pressurized aerosols, metered dose inhalers, dry powder inhalers, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation of pharmaceutically acceptable tonicity with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example, those suitable for oral administration may include flavoring agents.

Examples

Crystal Structure of RJW100 Bound to LRH-1

Figure 3A:
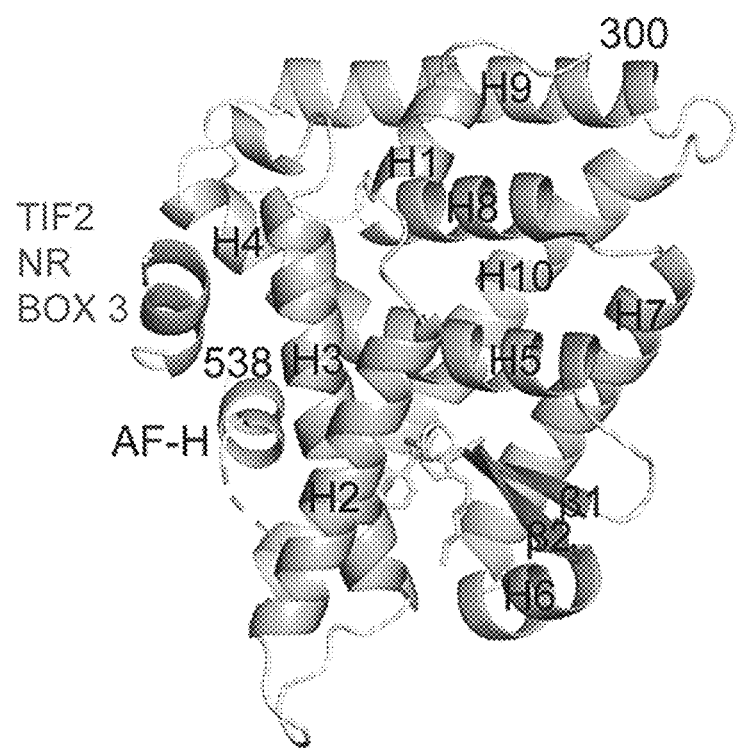
FIG. 3A illustrated overall structure, with α-helices shown in light and β-sheets in slate. The Tif2 peptide is bound at the AFS. The ligand is bound at a single site in the binding pocket. Dashed line, region of disorder in the protein backbone that could not be modeled.
Figure 3B:
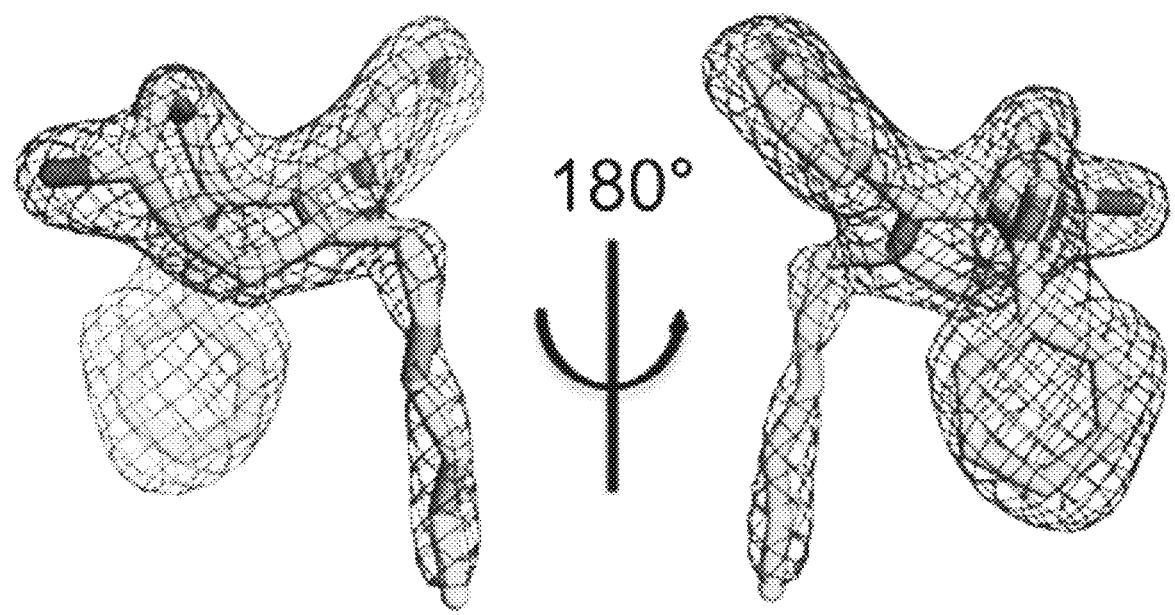
FIG. 3B shows an omit map (FO-FC, contoured at 2.5 σ) showing that a single enantiomer of RJW100 is bound in the structure.

To understand how RJW100 interacts with LRH-1 and affects receptor conformation, the x-ray crystal structure of LRH-1 LBD bound to the agonist and to a fragment of the co-activator, Tif2, to a resolution of 1.85 Å was determined (FIG. 3A). Although the RJW100 used for crystallization was a racemic mixture of two exo stereoisomers (FIG. 1B), the electron density in the structure unambiguously indicates that a single enantiomer is bound (FIG. 3B). The bound isomer has R stereochemistry at both the 1-position (hydroxyl-substituted) and 3a-position (styrene-substituted) (hereafter RR-RJW100, FIG. 1B). The ligand is bound at a single site deep in the binding pocket and is fully engulfed within it. This binding mode is markedly different from that of the PL ligands, DLPC and PIP3, which extend lower in the pocket with the headgroups protruding into the solvent (seen by superposition with PDBs 4DOS and 4RWV, respectively, FIGS. 3C and D). PL ligands also increase the pocket volume and width compared with RJW100. For example, the mouth of the pocket is ~3 Å wider and nearly 40% larger in volume when DLPC is bound versus RJW100 (FIG. 3E). This effect appears to be mainly due to a shift of H6, which swings away from the mouth of the pocket in the DLPC structure by ~3 Å (FIG. 3E). The direction and magnitude of the H6 movement are similar in other LRH-1-PL structures; comparison of four published human LRH-1-PL structures shows an average H6 shift of 3.0±0.2 Å relative to LRH-1 in the apo-state or when synthetic ligands are bound. Although these structures exhibit diverse types of crystal packing, the movement of H6 appears to be related to whether the ligand is a PL or small molecule and not to crystal form or packing contacts. It likely occurs to avoid stearic clashes with the PL headgroup. Notably, the H6/β-sheet region has been recently identified as a site through which PL ligands allosterically communicate with the AFS to modulate LRH-1 activity. The fact that the synthetic agonists do not displace H6 relative to the apo-receptor suggests that they utilize a different mechanism for receptor activation.

Repositioning of RJW100 Compared with a Closely Related Synthetic Agonist

Figure 4A:
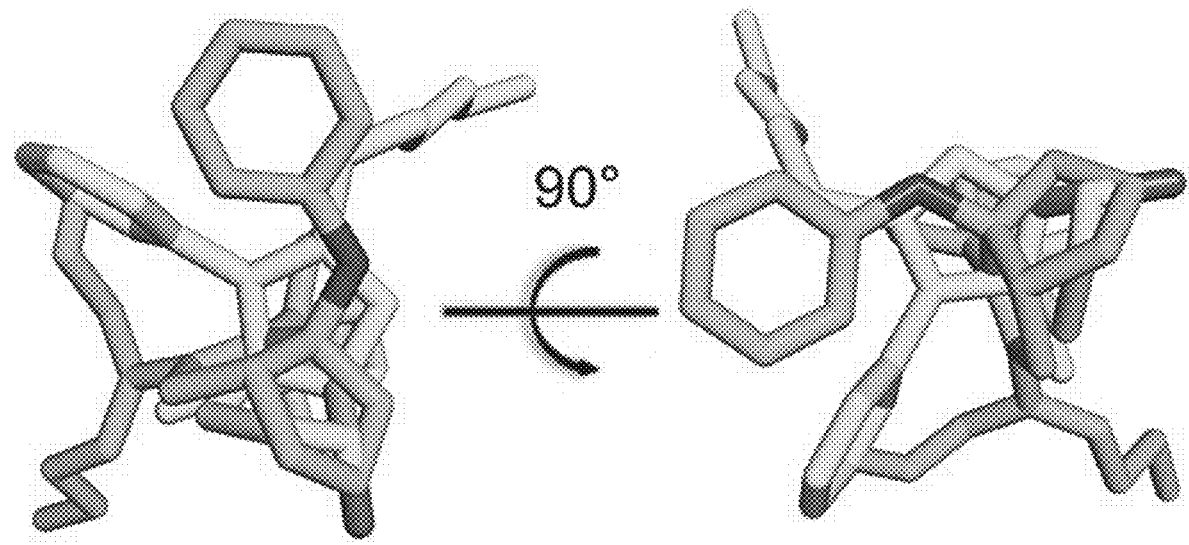
FIG. 4A shows superposition of coordinates for GSK8470 (from PBD 3PLZ) and RR-RJW100.
Figure 4B:
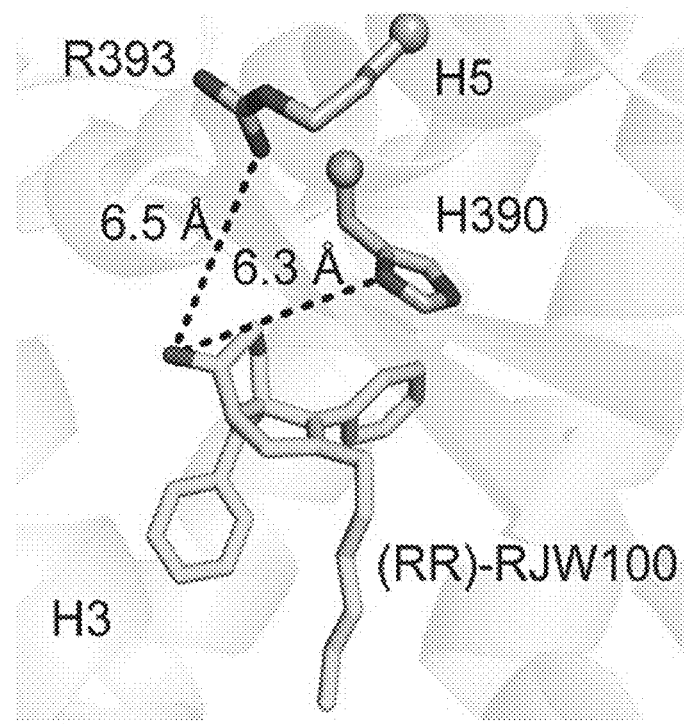
FIG. 4B shows RR-RJW100 hydroxyl group was predicted to interact with residues His-390 and Arg-393, but it is over 6 Å away from these residues in the structure.

Perhaps the most striking observation from structure comes from comparison of RJW100 with GSK8470-bound LRH-1 (PBD 3PLZ). Overall, protein conformation is highly similar; the largest movement occurs in the bottom of H3, which moves in the direction of H6 (by 2 Å in the RR-RJW100 structure and by 4 Å in the GSK8470 structure relative to apo-LRH-1). However, there is a substantial difference in the positioning of these agonists within the binding pocket. Although GSK8470 and RR-RJW100 bind in the same vicinity, they are rotated nearly 180° from one another. The bicyclic rings at the cores of each molecule are perpendicular to each other, causing the tails to be pointed in opposite directions (FIG. 4A). Notably, the rationale for adding a hydroxyl group in the 1-position on this scaffold was to promote an interaction with a "polar patch," consisting of residues Arg-393 and is-390 in an otherwise hydrophobic pocket. This interaction was predicted based on the position of the ligand in the LRH-1-GSK8470 structure; however, the actual position of RR-RJW100 in the pocket places the hydroxyl group over 6 Å away from these residues (FIG. 4B). Such a radically different binding mode for closely related molecules was unexpected, and a propensity to rotate within the pocket may contribute to difficulties improving agonist activity by modification of the GSK8470 scaffold.

Discovery of a LRH-1 Interaction Mediated by the RJW100 Hydroxyl Group

Protein-ligand interactions made by GSK8470 and the RJW100 stereoisomers were examined to gain insight into factors influencing the ligand-binding mode. A close view of the LRH-1-binding pocket reveals that RR-RJW100 makes several hydrophobic contacts, many of which are also made by GSK8470 (shown in, FIG. 5A). Additionally, RR-RJW100 makes several unique contacts (shown in FIG. 5A). Many of these unique contacts are also hydrophobic; however, the RR-RJW100 hydroxyl group forms an indirect polar contact with residue Thr-352 via a water molecule. A portion of the electron density map is shown in FIG. 5A to emphasize the strong evidence for this interaction. SR-RJW100 also interacts with Thr-352 through the same water molecule, despite the differing conformations of the hydroxyl group (FIG. 5B). The position of the SR-RJW100 hydroxyl group also permits a second water-mediated hydrogen-bonding interaction with the backbone nitrogen of residue Val-406 (FIG. 5B).

Although the interaction with Thr-352 is indirect, the water molecule involved is part of a network of waters found in every LRH-1 crystal structure in the same location. Additional support for modeling water at these sites in the pocket comes from B-factors of ligating atoms. Thus, this water network appears to be a conserved feature of the binding pocket and may play a role in receptor function or stability. To test the hypothesis that the OH-water-Thr-352 interaction was influencing ligand positioning, the stability of this bond was analyzed using molecular dynamics simulations (MDS). Throughout each simulation (200 ns), the four conserved networked water molecules remained in the same positions (if a particular water molecule occasionally left, it was immediately replaced with another in the same location). Residue Thr-352 maintained a hydrogen bond with the water molecule for 100% of each simulation, regardless of which ligand was bound. Additionally, both RR-RJW100 and SR-RJW100 maintained hydrogen bonding with the water molecule for the majority of the simulations (53.7% of the time for RR-RJW100 and 64.4% of the time for SR-RJW100). When residue Thr-352 was mutated to valine in MDS, the time spent interacting with the Thr-352-coordinated water molecule was drastically reduced (22.9 and 0.5% when RR-RJW100 and SR-RJW100 were bound, respectively), demonstrating that this mutation likely disrupts this water-mediated interaction made by these ligands.

Differences in π-π Stacking with Residue His-390 among LRH-1 Agonists

The π-π-stacking of GSK8470 with residue His-390 has been described as important for activation of LRH-1 by synthetic compounds. The RJW100 diastereomers also engage in π-π-stacking with His-390, but with some key differences. The π-π-stacking is face-to-face for GSK8470 and edge-to-face for the RJW100 isomers. Additionally, by virtue of the very different orientations in the binding pocket, the agonists do not use analogous phenyl rings for π-π-stacking; GSK8470 uses the aniline group, whereas the RJW100 isomers use the adjacent phenyl substituent. Moreover, MDS demonstrate ligand-dependent differences in the stability of this interaction.

Role of Thr-352 and His-390 in LRH-1 Activation by Synthetic Agonists

The importance of the Thr-352 and His-390 interactions for binding and activation of LRH-1 by the agonists was investigated using mutagenesis. Binding and stabilization of LRH-1 were detected using DSF. Although the T352V mutation (designed to remove the water-mediated hydrogen bond with bound ligands) had little effect on the overall thermostability of DLPC-bound LRH-1, it completely abrogated the stabilizing effect of RR-RJW100 and SR-RJW100. Likewise, disrupting this interaction by using an RJW100 analog lacking the hydroxyl group prevented the positive Tm shift in wild-type (WT) LRH-1 (FIG. 6A). GSK8470 did not affect the melting profile of LRH-1 in WT or T352V protein, supporting the notion that the hydroxyl group is important for stabilizing the protein-ligand complex.

The Thr-352 interaction was also found to be important for LRH-1 activation by small molecule agonists. The Compound lacking the hydroxyl group and unable to make this interaction, was an extremely poor LRH-1 activator in luciferase reporter assays. The endo-RJW100 was also a weak agonist, although statistically significant activation was achieved at the highest dose with WT LRH-1 (~1.4-fold over DMSO, FIG. 6D). RR-RJW100 and GSK8470 were equally effective toward WT LRH-1, and both increased activity by ~2.5-fold compared with DMSO at the highest dose, and both had EC$_{50}$ values of around 4 μm (FIGS. 6B and 6C). Notably, the T352V mutation greatly reduced the ability of RR-RJW100 to activate LRH-1 compared with WT protein, while not significantly affecting baseline activity. Unexpectedly, this mutation similarly attenuated activation by GSK8470, perhaps suggesting a broader role for this residue (or perhaps for the water network it coordinates) in ligand-mediated activation. Indeed, introduction of a T352V mutation to GSK8470-bound LRH-1 in MDS disrupts the water network, causing complete displacement of the water molecule typically coordinated by Thr-352. The T352V mutation also significantly reduces the amount of time GSK8470 spends π-π-stacking with His-390 (25.7% versus 89.5% of the simulation). Both the destabilization of the water network and the disruption of stable His-390 π-π-stacking by the T352V mutation could contribute to the observed loss of activity for GSK8470 in the context of this mutation.

Although the T352V mutation resulted in a loss of activity for both RR-RJW100 and GSK8470, mutating His-390 to alanine had a different effect on LRH-1 activation depending on the agonist involved. GSK8470 was completely unable to activate H390A-LRH-1, but this mutation had little to no effect on RR-RJW100-mediated activation. This differential reliance on His-390 for activation is consistent with the observation that GSK8470 interacts with His-390 more stably than RR-RJW100 in MDS. This also provides evidence that RR-RJW100 utilizes a different mechanism of action than GSK8470 for LRH-1 activation.

Synthesis of Hexahydropentalene Derivatives

The general strategy for preparing hexahydropentalene derivatives is illustrated in FIG. 1 using procedures set out in, or as appropriately modified from, Whitby et al. (2011). Small molecule agonists of the orphan nuclear receptors steroidogenic factor-1 (SF-1, NR5A1) and liver receptor homologue-1 (LRH-1, NR5A2). Journal of Medicinal Chemistry, 54, 2266-2281.

Synthetic Scheme for Enyne (4)

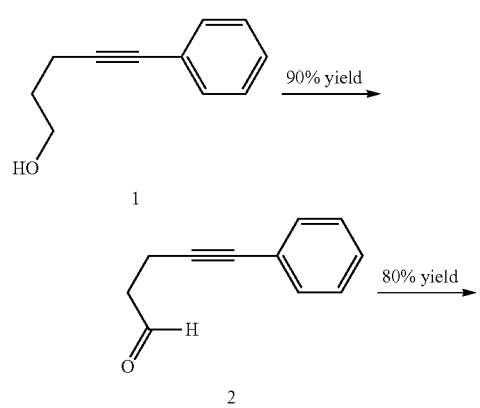

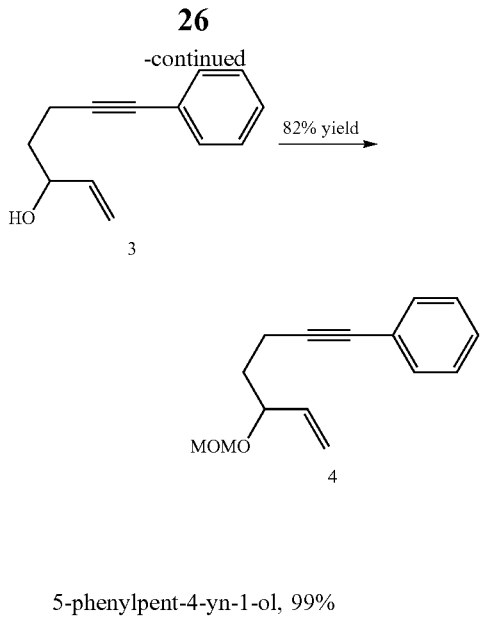

5-phenylpent-4-yn-1-ol, 99%

To an oven-dried round bottom flask was added bis (triphenylphosphine)palladium dichloride (0.03 equiv.) and copper iodide (0.06 equiv.). Triethylamine was added to make a 1.0 M solution before the addition of iodobenzene (1.0 equiv.) The resulting yellow mixture was sparged by bubbling the solution with nitrogen for a period of 30 minutes, at which point 4-pentyl-1-ol (1.2 equiv.) was added portionwise and the sparging needle was replaced with a nitrogen inlet. The solution rapidly darkened and formed a slurry, and was heated at 60 C for 2 hours, at which point the reaction was complete by TLC. The resulting black solution was cooled and ether was added to precipitate a black solid. The resulting slurry was filtered over a plug of celite and eluted with ether. The filtrate was concentrated in vacuo to afford a reddish-brown oil, which was then purified on silica in 30% EtOAc/hex to afford a red oil.

5-phenylpent-4-ynal, 83%

To an oven-dried 3-neck flask under nitrogen, oxalyl chloride (1.1 equiv.) in DCM (0.1M) was cooled to −78 C in a dry ice/acetone bath. Dimethylsulfoxide (DMSO) (1.3 equiv.) was added dropwise as a solution in DCM. The solution was allowed to stir approximately 10 minutes until bubbling ceased. The required alcohol was then added dropwise as a solution in DCM. The reaction mixture was stirred and maintained at −78 C for 1 hour. Triethylamine (2.5 equiv.) was then added at −78 C and allowed to warm to room temperature. The reaction was quenched with saturated aqueous ammonium chloride and extracted with ethyl acetate. The combined organics were washed with brine, dried with MgSO$_4$ and concentrated in vacuo. The resulting residue was purified on silica in 10-20% EtOAc/Hexanes to afford a clear, yellow oil.

7-phenylhept-1-en-6-yn-3-ol, 81%

To an oven-dried 3-neck flask under nitrogen was added aldehyde, (1.0 equiv.) as a solution in dry THE. The solution as cooled to −78 C and vinylmagnesium bromide (1.0 M, 1.5 equiv.) was added. The reaction mixture was stirred and allowed to warm to room temperature over 5 h. The reaction was quenched with ammonium chloride, poured onto water, and extracted with ethyl acetate. The combined organic layers were washed with brine, dried with MgSO₄ and concentrated in vacuo. The resulting oil was purified on silica in 5-10% EtOAc/Hexanes to afford a clear, colorless oil.

(5-(methoxymethoxy)hept-6-en-1-ynl) benzene (4), 68%

Allylic alcohol (1.0 equiv.) was dissolved in DCM and cooled to 0 C. Diisopropylethyl amine (1.25 equiv.) was added, followed by chloro(methoxy)methane (1.5 equiv.). The reaction mixture was stirred over 18 hours, and then poured over water and extracted with DCM. The combined organic layers were washed with 1M HCl, then brine, then dried over MgSO₄ and concentrated in vacuo. The resulting oil was purified in 5% EtOAc/Hexanes to afford a clear, colorless oil.

Synthesis of Dibromo Compounds

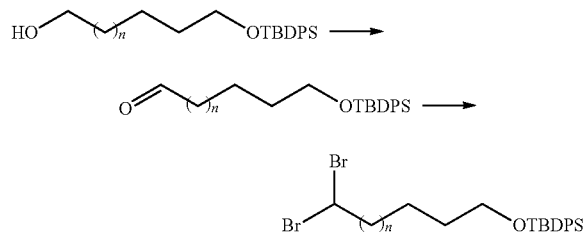

General Procedure for the Formation of TBDPS-Protected Diols

To a round bottom flask open to air the required diol (2.0 equiv.) was dissolved in THF to make a 0.1M solution. Imidazole (1.0 equiv.) was added, followed by tert-butyl diphenyl silyl chloride (TBDPSCl) (1.0 equiv.). The resulting solution was allowed to stir for 18 h, upon which a solid white precipitate formed. The solution was filtered and the filtrate concentrated in vacuo. The resulting material was subjected to silica gel chromatography in 5-15% EtOAc/Hexanes to afford a clear, colorless oil.

| n | IUPAC Name | Yield (%) |
|---|---|---|
| 1 | 5-((tert-butyldiphenylsilyl)oxy)pentan-1-ol 5a | 88 |
| 2 | 6-((tert-butyldiphenylsilyl)oxy)hexan-1-ol 6a | 40 |
| 3 | 7-((tert-butyldiphenylsilyl)oxy)heptan-1-ol 7a | 38 |
| 4 | 8-((tert-butyldiphenylsilyl)oxy)octan-1-ol 8a | 74 |
| 5 | 9-((tert-butyldiphenylsilyl)oxy)nonan-1-ol 9a | 82 |
| 6 | 10-((tert-butyldiphenylsilyl)oxy)decan-1-ol 10a | 81 |
| 7 | 11-((tert-butyldiphenylsilyl)oxy)undecan-1-ol 11a | 82 |
| 8 | 12-((tert-butyldiphenylsilyl)oxy)dodecan-1-ol 12a | 35 |

General Procedure for the Formation of TBDPS Protected Aldehydes

To a round bottom flask open to air the required TBDPS-monoprotected diol (1a-8a) was dissolved in dichloromethane to form a 0.1M solution. Trichloroisocyanuric acid (1.0 equiv.) was added to the reaction mixture, followed by (2,2,6,6-Tetramethyl-piperidin-1-yl)oxyl (TEMPO) (0.01 equiv.). The reaction was monitored by TLC until consumption of the starting diol was consumed (less than 10 minutes). The resulting solution was poured over water and quenched with saturated sodium bicarbonate. The aqueous layer was extracted with dichloromethane three times. The combined organic layers were then washed with 1 M HCl and brine, after which the organic layer was dried with MgSO₄ and concentrated in vacuo. The resulting oil was subjected to silica gel chromatography in 20% EtOAc/Hexanes to afford a clear, colorless oil.

| n | IUPAC Name | Yield (%) |
|---|---|---|
| 1 | 5-((tert-butyldiphenylsilyl)oxy)pentanal (5b) | 90 |
| 2 | 6-((tert-butyldiphenylsilyl)oxy)hexanal (6b) | 82 |
| 3 | 7-((tert-butyldiphenylsilyl)oxy)heptanal (7b) | 93 |
| 4 | 8-((tert-butyldiphenylsilyl)oxy)octanal (8b) | 57 |
| 5 | 9-((tert-butyldiphenyl silyl)oxy)nonanal (9b) | 63 |
| 6 | 10-((tert-butyldiphenyl silyl)oxy)decanal (10b) | 88 |
| 7 | 11-((tert-butyldiphenylsilyl)oxy)undecanal (11b) | 60 |
| 8 | 12-((tert-butyldiphenylsilyl)oxy)dodecanal (12b) | 95 |

General Procedure for the Formation of Terminal Gem-Dibromo Compounds 1c-8c

Triphenylphosphite (1.1 equiv) was added to an oven-dried three-neck flask under nitrogen, dissolved in dichloromethane (DCM), and cooled to −78 C in a dry ice/acetone bath. Bromine (1.1 equiv) was added portionwise. Triethylamine (1.1 equiv.) was added dropwise and the solution was allowed to stir for 5 minutes. The required aldehyde (1b-8b) was added as a solution in dichloromethane and the mixture was allowed to stir for 5 hours. Upon completion, the reaction mixture was filtered over a plug of silica (eluted with ethyl acetate) and the filtrate was concentrated in vacuo. The resulting oil was subjected to a short plug of silica and eluted with 100% hexanes to afford a clear, colorless oil.

| IUPAC Name | Yield (%) |
|---|---|
| tert-butyl((5,5-dibromopentyl)oxy)diphenylsilane (5c) | 73 |
| tert-butyl((6,6-dibromohexyl)oxy)diphenylsilane (6c) | 74 |
| tert-butyl((7,7-dibromoheptyl)oxy)diphenylsilane (7c) | 45 |
| tert-butyl((8,8-dibromooctyl)oxy)diphenylsilane (8c) | 81 |
| tert-butyl((9,9-dibromononyl)oxy)diphenylsilane (9c) | 89 |
| tert-butyl((10,10-dibromodecyl)oxy)diphenylsilane (10c) | 55 |
| tert-butyl((11,11-dibromoundecyl)oxy)diphenylsilane (11c) | 63 |
| tert-butyl((12,12-dibromododecyl)oxy)diphenylsilane (12c) | 65 |

Bis-Protected 5,5-Bicyclic Compounds

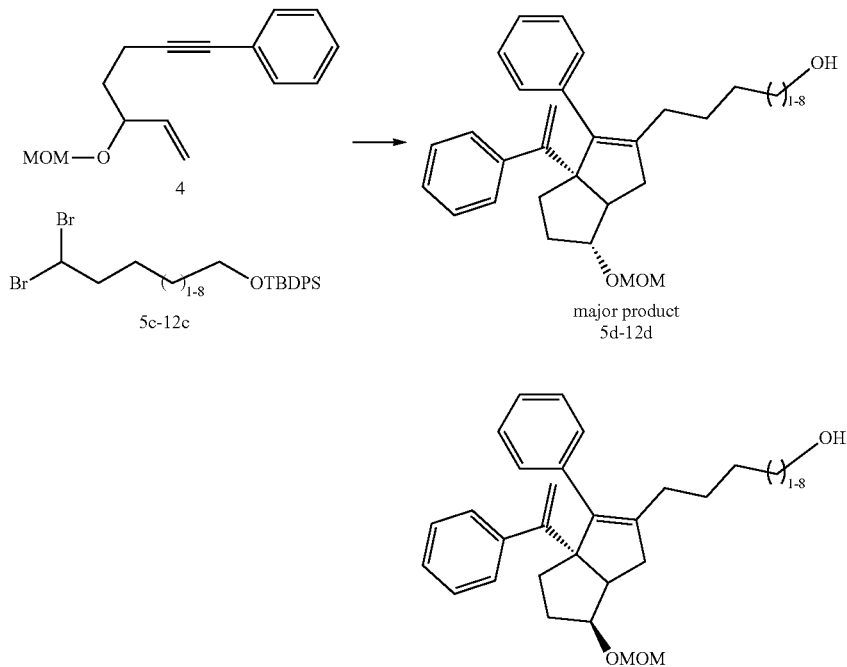

major product
5d-12d

General Procedure for MOM-Protected 2°, Deprotected 1° Alcohols (5d-12d)

Bis(cyclopentadienyl)zirconium(IV) dichloride (zirconecene dichloride) (1.2 equiv.) was dried by azeotroping away latent water with benzene four times before being placed under nitrogen, dissolved in dry, degassed tetrahydrofuran (THF) and cooled to −78° C. in a dry ice/acetone bath. The resulting solution of zirconecene dichloride was treated with nBuLi (1.6M in hex, 2.4 equiv.) to form a clear, light yellow solution and allowed to stir. After approximately 30 minutes, azeotroped (5-(methoxymethoxy)hept-6-en-1-yn-1-yl)benzene (4) (1.0 equiv.) in dry, degassed THF was added portionwise to afford a pink-orange solution, and the reaction mixture was held at −78° C. for 30 minutes before allowing to warm to room temperature and stirred over 2.5 hours. The reaction mixture was then re-cooled to −78° C. and the required azeotroped required 1,1-dibromoalkane protected alcohol (5c-12c) (1.1 equiv.) were added in dry, degassed THF. Freshly prepared lithium diisopropylamine (LDA, 1.0 M, 1.1 equiv.) was added at −78° C. and stirred for 15 minutes. Freshly prepared lithium phenylacetylide (3.6 equiv.) was added to the reaction mixture dropwise in dry, degassed THF. The resulting dark reddish brown solution was stirred at −78° C. for 1.5 hours. The reaction was then quenched with methanol and saturated aqueous sodium bicarbonate and allowed to warm to room temperature to form a light yellow slurry. The slurry was poured over water and extracted with ethyl acetate four times. The combined organic layers were washed with brine, dried with MgSO$_4$, and concentrated in vacuo. The resulting colored yellow oil was roughly purified on a plug of silica and eluted with 20% EtOAc/Hexanes to afford an oil which is a mixture of quenched phenylacetylide, desired bis-protected [3.3.0] bicyclic compounds (and in some cases protonolysis byproduct), which was carried on without further purification. The crude oil was then dissolved in a round bottom flask charged with a stir bar and open to air. TBAF (approx. 2.0 equiv. of enyne starting material) was added. The solution rapidly darkened and was allowed to stir at room temperature for 16 h. After reaction completion, the reaction mixture was concentrated and directly subjected to purification by silica gel chromatography to afford the desired cyclized, free primary alcohol products 5d-12d.

| Identifier | Compound Name of Major Product | % Yield (2 steps) |
|---|---|---|
| 5d | 4-(6-exo-(methoxymethoxy)-3-phenyl-3a-(1-phenylvinyl)-1,3a,4,5,6,6a-hexahydropentalen-2-yl)butan-1-ol | 40 |
| 6d | 5-(6-exo-(methoxymethoxy)-3-phenyl-3a-(1-phenylvinyl)-1,3a,4,5,6,6a-hexahydropentalen-2-yl)pentan-1-ol | 62 |
| 7d | 6-(6-exo-(methoxymethoxy)-3-phenyl-3a-(1-phenylvinyl)-1,3a,4,5,6,6a-hexahydropentalen-2-yl)hexan-1-ol | 80 |
| 8d | 7-(6-exo-(methoxymethoxy)-3-phenyl-3a-(1-phenylvinyl)-1,3a,4,5,6,6a-hexahydropentalen-2-yl)heptan-1-ol | 42 |
| 9d | 8-(6-exo-(methoxymethoxy)-3-phenyl-3a-(1-phenylvinyl)-1,3a,4,5,6,6a-hexahydropentalen-2-yl)octan-1-ol | 72 |
| 10d | 9-(6-exo-(methoxymethoxy)-3-phenyl-3a-(1-phenylvinyl)-1,3a,4,5,6,6a-hexahydropentalen-2-yl)nonan-1-ol | 53 |
| 11d | 10-(6-exo-(methoxymethoxy)-3-phenyl-3a-(1-phenylvinyl)-1,3a,4,5,6,6a-hexahydropentalen-2-yl)decan-1-ol | 60 |

| Identifier | Compound Name of Major Product | % Yield (2 steps) |
|---|---|---|
| 12d | 11-(6-exo-(methoxymethoxy)-3-phenyl-3a-(1-phenylvinyl)-1,3a,4,5,6,6a-hexahydropentalen-2-yl)undecan-1-ol | 70 |

General Procedure for Diols (5e-12e)

To a solution of required cyclized primary alcohols (5d-12d) in acetonitrile was added concentrated HCl in excess (5-20 equiv.). The solution was stirred for 18 h or until the reaction was completed by TLC. The resulting solution as concentrated in vacuo and subjected to preparatory HPLC to isolate the desired product as the major exo diastereomer.

| Identifier | Compound Name |
|---|---|
| 5e | Exo-5-(4-hydroxybutyl)-4-phenyl-3a-(1-phenylvinyl)-1,2,3,3a,6,6a-hexahydropentalen-1-ol |
| 6e | Exo-5-(5-hydroxypentyl)-4-phenyl-3a-(1-phenylvinyl)-1,2,3,3a,6,6a-hexahydropentalen-1-ol |
| 7e | Exo-5-(6-hydroxyhexyl)-4-phenyl-3a-(1-phenylvinyl)-1,2,3,3a,6,6a-hexahydropentalen-1-ol |
| 8e | Exo-5-(7-hydroxyheptyl)-4-phenyl-3a-(1-phenylvinyl)-1,2,3,3a,6,6a-hexahydropentalen-1-ol |
| 9e | Exo-5-(8-hydroxyoctyl)-4-phenyl-3a-(1-phenylvinyl)-1,2,3,3a,6,6a-hexahydropentalen-1-ol |
| 10e | Exo-5-(9-hydroxynonyl)-4-phenyl-3a-(1-phenylvinyl)-1,2,3,3a,6,6a-hexahydropentalen-1-ol |
| 11e | Exo-5-(10-hydroxydecyl)-4-phenyl-3a-(1-phenylvinyl)-1,2,3,3a,6,6a-hexahydropentalen-1-ol |
| 12e | Exo-5-(11-hydroxyundecyl)-4-phenyl-3a-(1-phenylvinyl)-1,2,3,3a,6,6a-hexahydropentalen-1-ol |

Characterization Data for Diols

5e:
$^1$H NMR (600 MHz, Chloroform-d) δ 7.33-7.24 (m, 6H), 7.23 (s, 2H), 7.20-7.16 (m, 2H), 5.05 (d, J=1.4 Hz, 1H), 4.97 (d, J=1.5 Hz, 1H), 3.93 (s, 1H), 3.55 (t, J=6.2 Hz, 2H), 2.36 (dd, J=16.9, 9.3 Hz, 1H), 2.29 (d, J=6.9 Hz, 1H), 2.10-2.02 (m, 4H), 1.74-1.61 (m, 3H), 1.50-1.37 (m, 4H). $^{13}$C NMR (500 MHz, Chloroform-d) δ 154.60, 144.10, 140.77, 139.42, 137.31, 129.62, 127.71, 127.67, 127.63, 126.61, 116.56, 114.84, 81.80, 69.29, 62.39, 55.65, 40.13, 33.94, 32.65, 32.01, 29.44, 24.03, 22.45, 10.57. HRMS calcd for C26H31O2 [M+H]+: 375.23186, found 375.23145 IR (cm-1): 3344(b), 3079 (w), 2937, 2191(w), 1737, 1669, 1597, 1490, 1440, 1378, 1349, 1229, 1217, 1070, 1028.

6e:
$^1$H NMR (500 MHz, Chloroform-d) δ 7.43-7.28 (m, 7H), 7.28-7.19 (m, 3H), 5.09 (d, J=1.4 Hz, 1H), 5.01 (d, J=1.4 Hz, 1H), 3.97 (s, 1H), 3.61 (t, J=6.6 Hz, 2H), 2.38 (dd, J=16.8, 9.4 Hz, 1H), 2.31 (d, J=9.3, 1.5 Hz, 1H), 2.16-2.03 (m, 4H), 1.77-1.65 (m, 3H), 1.56-1.48 (m, 3H), 1.43-1.25 (m, 3H). $^{13}$C NMR (500 MHz, Chloroform-d) δ 154.50, 144.12, 140.79, 139.31, 137.27, 131.51, 129.64, 128.19, 127.72, 127.64, 126.66, 126.64, 115.04, 82.03, 69.32, 62.85, 61.85, 55.76, 40.25, 33.98, 32.51, 32.05, 31.33, 29.65, 27.62, 25.75, 15.98. HRMS calcd for C-27H33O2 [M+H]+: 389.24751, found 398.24762 IR (cm-1): 3332 (b), 3079(w), 2933, 1490, 1441, 1342, 1191, 1071, 1035.

7e:
$^1$H NMR (600 MHz, Chloroform-d) δ 7.36-7.25 (m, 6H), 7.24-7.15 (m, 4H), 5.05 (s, 1H), 4.97 (s, 1H), 3.93 (s, 1H), 3.58 (t, J=6.6 Hz, 2H), 2.35 (dd, J=16.9, 9.4 Hz, 1H), 2.28 (d, J=9.4 Hz, 1H), 2.11-1.97 (m, 4H), 1.75-1.62 (m, 3H), 1.53-1.46 (m, 2H), 1.38-1.15 (m, 6H). $^{13}$C NMR (600 MHz, Chloroform-d) δ 154.52, 144.14, 140.94, 139.23, 137.33, 129.68, 127.70, 127.62, 126.66, 126.61, 115.04, 109.98, 82.03, 69.33, 62.96, 55.76, 40.25, 33.97, 32.63, 32.08, 29.57, 29.38, 27.73, 25.46, HRMS calcd for C28H35O2 [M+H]+: 403.26316, found 403.26338 IR (cm-1) 3330 (b), 3051 (w), 2929, 2855, 1490, 1440, 1340.74, 1262.75, 1191, 1071, 1028.

8e:
$^1$H NMR (600 MHz, Chloroform-d) δ 7.35-7.25 (m, 5H), 7.24-7.15 (m, 5H), 5.05 (d, J=1.4 Hz, 1H), 4.97 (d, J=1.4 Hz, 1H), 3.93 (s, 1H), 3.60 (t, J=6.7 Hz, 2H), 2.35 (dd, J=16.9, 9.3 Hz, 1H), 2.28 (d, J=9.4 Hz, 1H), 2.09-1.98 (m, 5H), 1.73-1.61 (m, 3H), 1.36-1.19 (m, 10H). $^{13}$C NMR (600 MHz, Chloroform-d) δ 154.53, 144.14, 141.03, 139.16, 137.33, 129.67, 127.70, 127.61, 126.64, 126.59, 115.02, 82.03, 69.31, 63.00, 58.47, 55.76, 50.89, 40.22, 33.96, 32.71, 32.07, 29.63, 29.58, 29.16, 27.71, 25.61, 18.42. HRMS calcd for C29H36O2Cl [M+Cl]−: 451.24093, found 451.24179 IR (cm-1): 3347 (b), 3079 (w), 3052 (w), 2929, 2855, 1491, 1441, 1342, 1261, 1192, 1028.

9e:
$^1$H NMR (600 MHz, Chloroform-d) δ 7.35-7.25 (m, 6H), 7.24-7.16 (m, 4H), 5.05 (d, J=1.4 Hz, 1H), 4.97 (d, J=1.4 Hz, 1H), 3.93 (s, 1H), 3.61 (t, J=6.7 Hz, 2H), 2.35 (dd, J=16.9, 9.3 Hz, 1H), 2.28 (d, J=9.2 Hz, 1H), 2.10-2.01 (m, 2H), 2.00-1.97 (m, 2H), 1.74-1.61 (m, 3H), 1.35-1.16 (m, 13H). HRMS calcd for C30H38O2Cl [M+Cl]−: 465.25658, found 465.25703 IR (cm-1): 3344 (b), 3079 (w), 3052 (w), 2927, 2854, 1491, 1440, 1343, 1261, 1192, 1071, 1029.

10e:
$^1$H NMR (600 MHz, Chloroform-d) δ 7.39-7.26 (m, 5H), 7.24-7.14 (m, 5H), 5.05 (d, J=1.4 Hz, 1H), 4.97 (d, J=1.4 Hz, 1H), 3.93 (s, 1H), 3.62 (t, J=9.4 Hz, 2H), 2.34 (dd, J=16.7, 9.4 Hz, 1H), 2.27 (d, J=9.3 Hz, 1H), 2.12-2.03 (m, 2H), 2.01-1.96 (m, 1H), 1.74-1.58 (m, 3H), 1.34-1.17 (m, 18H). $^{13}$C NMR (600 MHz, Chloroform-d) δ 154.56, 144.15, 141.13, 139.08, 137.35, 129.68, 127.71, 127.70, 127.59, 126.64, 126.57, 115.01, 82.05, 69.32, 63.06, 55.77, 40.23, 33.97, 32.76, 32.08, 29.66, 29.61, 29.46, 29.36, 29.31, 27.78, 25.67. HRMS calcd for C31H40O2Cl [M+Cl]−: 479.27223, 479.27260 IR (cm-1): 3343 (b), 3079 (w), 3052 (w), 2928, 2854, 1670.41, 1598, 1491, 1440, 1344, 1192, 1071, 1055, 1029.

11e:
$^1$H NMR (600 MHz, Chloroform-d) δ 7.35-7.25 (m, 5H), 7.24-7.16 (m, 5H), 5.05 (d, J=1.4 Hz, 1H), 4.97 (d, J=1.4 Hz, 1H), 3.93 (s, 1H), 3.61 (t, J=6.7 Hz, 2H), 2.34 (dd, J=16.9, 9.4 Hz, 1H), 2.27 (d, J=9.2 Hz, 1H), 2.11-2.00 (m, 3H), 1.73-1.62 (m, 3H), 1.54 (dq, J=8.2, 6.7 Hz, 2H), 1.34-1.17 (m, 17H). LRMS [APCI] calcd for C32H41O2 [M−H]−: 457.3, found 457.2.

12e:
$^1$H NMR (600 MHz, Chloroform-d) δ 7.34-7.25 (m, 4H), 7.24-7.16 (m, 5H), 5.05 (d, J=1.4 Hz, 1H), 4.96 (d, J=1.3 Hz, 1H), 3.93 (s, 1H), 3.61 (t, J=6.7 Hz, 2H), 2.33 (dd, J=17.2, 9.8 Hz, 1H), 2.26 (d, J=9.3 Hz, 1H), 2.09-1.99 (m, 1H), 2.02-1.99 (m, 5H), 1.72-1.61 (m, 3H), 1.57-1.51 (m, 2H), 1.40-1.11 (m, 10H). LRMS [APCI] calcd for C33H43O2 [M–H]–: 471.3, found 471.0.

Synthetic Scheme for [3.3.0] Bicyclic Carboxylic Acids

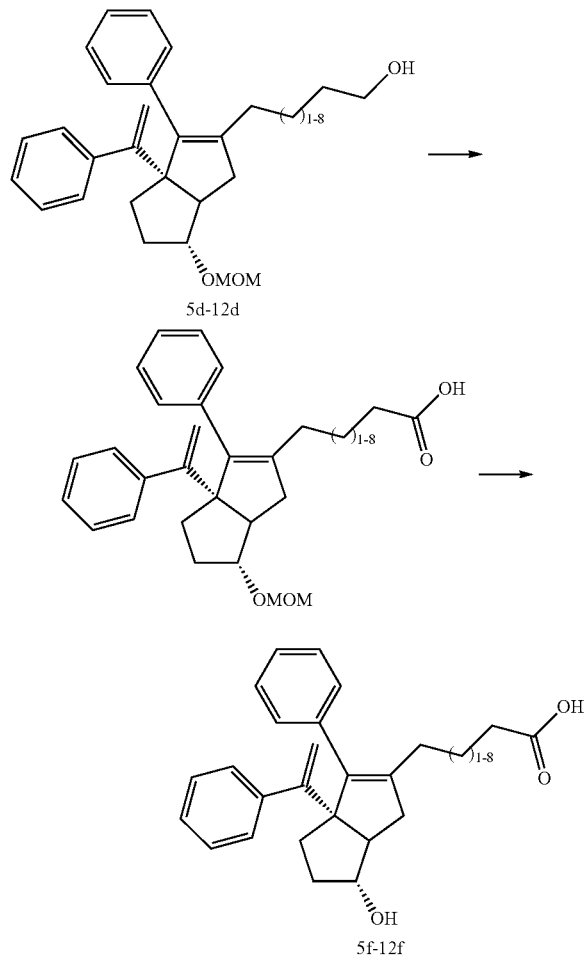

General Procedure for Carboxylic Acids (5f-12f)

A solution of tetrapropylammoniumperruthate (TPAP) (0.1 equiv.) and n-methylmorpholine oxide (NMO) (10.0 equiv.) in acetonitrile was made and added to the required cyclized primary alcohol (5d-12d) (1.0 equiv.) in a scintillation vial open to air. Reagent grade water (10.0 equiv.) was added and the solution was allowed to stir for 3 hours at room temperature, or until the reaction was complete by TLC. The resulting black solution was concentrated in vacuo and passed through a short plug of silica and eluted with 50% EtOAc/Hexanes with 0.1% Acetic Acid added to afford the protected carboxylic acid intermediates.

The resulting clear, colorless oil was subsequently taken up in acetonitrile, and concentrated HCl (5-10 equiv.) was added. The solution was allowed to stir for 30 minutes or until complete by TLC. The resulting solution was concentrated in vauco and subjected to preparatory HPLC to isolate the desired product as the major exo diastereomer.

| Identifier | Compound Name | Yield (2 steps) |
|---|---|---|
| 5f | 4-(6-exo-hydroxy-3-phenyl-3a-(1-phenylvinyl)-1,3a,4,5,6,6a-hexahydropentalen-2-yl)butanoic acid | 53 |
| 6f | 5-(6-exo-hydroxy-3-phenyl-3a-(1-phenylvinyl)-1,3a,4,5,6,6a-hexahydropentalen-2-yl)pentanoic acid | 78 |
| 7f | 6-(6-exo-hydroxy-3-phenyl-3a-(1-phenylvinyl)-1,3a,4,5,6,6a-hexahydropentalen-2-yl)hexanoic acid | 74 |
| 8f | 7-(6-exo-hydroxy-3-phenyl-3a-(1-phenylvinyl)-1,3a,4,5,6,6a-hexahydropentalen-2-yl)heptanoic acid | 98 |
| 9f | 8-(6-exo-hydroxy-3-phenyl-3a-(1-phenylvinyl)-1,3a,4,5,6,6a-hexahydropentalen-2-yl)octanoic acid | 95 |
| 10f | 9-(6-exo-hydroxy-3-phenyl-3a-(1-phenylvinyl)-1,3a,4,5,6,6a-hexahydropentalen-2-yl)nonanoic acid | 63 |
| 11f | 10-(6-exo-hydroxy-3-phenyl-3a-(1-phenylvinyl)-1,3a,4,5,6,6a-hexahydropentalen-2-yl)decanoic acid | 64 |
| 12f | 11-(6-exo-hydroxy-3-phenyl-3a-(1-phenylvinyl)-1,3a,4,5,6,6a-hexahydropentalen-2-yl)undecanoic acid | 66 |

Characterization Data for Carboxylic Acids

5f:
$^1$H NMR (500 MHz, CDCl3) δ 7.38-7.16 (m, 10H), 5.08 (d, J=1.4 Hz, 1H), 5.00 (d, J=1.4 Hz, 1H), 3.97 (s, 1H), 2.42-2.36 (m, 1H), 2.37-2.31 (m, 2H), 2.30-2.23 (m, 2H), 2.14-2.06 (m, 4H), 1.75-1.65 (m, 5H). LRMS (ESI, APCI) m/z: calc'd for C26H27O3 [M–H]– 387.2, found 387.1 HRMS calcd for C26H27O3 [M–H]–: 387.19657, found 387.19687.

6f:
$^1$H NMR (600 MHz, CDCl3) δ 7.56-6.96 (m, 10H), 5.05 (d, J=1.4 Hz, 1H), 4.97 (d, J=1.4 Hz, 1H), 3.93 (s, 1H), 2.38-2.23 (m, 4H), 2.13-1.97 (m, 5H), 1.74-1.62 (m, 3H), 1.53 (p, J=7.4 Hz, 2H), 1.44-1.32 (m, 2H).
$^{13}$C NMR (126 MHz, CDCl3) δ 177.81, 154.47, 144.11, 140.26, 139.83, 137.17, 129.65, 127.75, 127.73, 126.75, 126.71, 115.11, 82.02, 69.37, 55.77, 40.12, 34.00, 33.46, 32.09, 29.29, 27.19, 24.61. LRMS (ESI, APCI) m/z: calc'd for C27H30O3 [M–H]– 401.2, found 401.5. Calc'd for C27H29O2 [M–OH]+ 385.2, found 385.2 HRMS calcd for C27H31O3 [M+H]+: 403.22677, found 403.22661. IR (cm-1): 3386(b), 3079 (w), 3052 (2), 2940, 1707 (s), 1491, 1440, 1410, 1342, 1236, 1192, 1071, 1029.

7f:
$^1$H NMR (600 MHz, CDCl3) δ 7.49-7.05 (m, 10H), 5.05 (d, J=1.5 Hz, 1H), 4.97 (d, J=1.4 Hz, 1H), 3.93 (s, 1H), 2.36-2.21 (m, 4H), 2.10-1.97 (m, 5H), 1.73-1.61 (m, 3H), 1.59-1.51 (m, 2H), 1.34 (p, J=7.6 Hz, 2H), 1.28-1.20 (m, 2H). LRMS (ESI, APCI) m/z: calc'd for C28H31O3 [M–H]– 415.2, found 414.9. Calc'd for C28H31O2 [M–OH]+ 399.2, found 399.2 HRMS calcd for C28H32O3Na [M+Na]+: 439.22353, found 439.22370 IR (cm-1): 3386(b), 3079 (w), 2934, 2856, 1708(s), 1491, 1440, 1407, 1342, 1230, 1191, 1072, 1028.

8f:
$^1$H NMR (600 MHz, CDCl3) δ 7.37-7.14 (m, 9H), 5.05 (d, J=1.5 Hz, 1H), 4.97 (d, J=1.4 Hz, 1H), 3.93 (s, 1H), 2.38-2.25 (m, 4H), 2.11-1.97 (m, 4H), 1.76-1.47 (m, 4H), 1.33 (p, J=7.6 Hz, 2H), 1.29-1.14 (m, 6H). LRMS (ESI, APCI) m/z: calc'd for C29H33O3 [M–H]– 429.3, found 429.3. Calc'd for C29H33O2 [M–OH]+ 413.2, found 413.28 HRMS calcd for C29H33O3 [M–H]–: 429.24352, found 429.2378.

9f:
$^1$H NMR (600 MHz, CDCl3) δ 7.81-7.13 (m, 10H), 5.05 (s, 1H), 4.97 (s, 1H), 3.93 (s, 1H), 2.37-2.22 (m, 5H), 2.09-1.94 (m, 5H), 1.79-1.58 (m, 6H), 1.38-1.16 (m, 5H).

LRMS (ESI, APCI) m/z: calc'd for C30H35O3 [M−H]− 443.3, found 443.2. Calc'd for C30H35O2 [M−OH]+ 427.3, found 427.4 HRMS calcd for C30−H35O3 [M−H]−: 443.25917, found 443.25927

10f:
$^{1}$H NMR (500 MHz, CDCl3) δ 7.41-7.15 (m, 10H), 5.07 (d, J=1.4 Hz, 1H), 4.99 (d, J=1.4 Hz, 1H), 3.95 (s, 1H), 2.39-2.27 (m, 5H), 2.12-1.97 (m, 5H), 1.76-1.56 (m, 6H), 1.40-1.15 (m, 7H). 13C NMR (126 MHz, CDCl3) δ 179.49, 154.55, 144.14, 141.10, 139.16, 137.35, 129.69, 127.74, 127.71, 127.63, 126.67, 126.61, 115.00, 82.09, 69.33, 55.71, 40.23, 33.95, 32.08, 29.64, 29.53, 29.16, 29.10, 29.00, 24.65. LRMS (ESI, APCI) m/z: calc'd for C31H37O3 [M−H]− 457.3, found 457.3. Calc'd for C31H37O2 [M−OH]+ 441.3, found 440.8 HRMS (ESI) m/z: calc'd for for C31H37O3 [M−H]− 457.27482, found 457.27487 FT-IR (neat): 3361, 3079, 3052, 3019, 2928, 2854, 1708, 1598, 1491, 1441, 1410, 1340, 1278, 1241, 1192, 1073, 1029, 903, 766, 703 cm-1.

11f:
$^{1}$H NMR (500 MHz, CDCl3) δ 7.39-7.15 (m, 10H), 5.07 (d, J=1.6 Hz, 1H), 4.99 (d, J=1.6 Hz, 1H), 3.95 (s, 1H), 2.41-2.24 (m, 5H), 2.15-1.94 (m, 5H), 1.75-1.50 (m, 6H), 1.42-1.09 (m, 9H). $^{13}$C NMR (126 MHz, CDCl3) δ 179.44, 154.57, 144.15, 141.15, 139.11, 137.37, 129.69, 127.74, 127.71, 127.62, 126.66, 126.60, 115.00, 82.10, 69.33, 55.71, 40.25, 33.98, 33.94, 32.08, 29.65, 29.59, 29.30, 29.28, 29.19, 29.01, 27.78, 24.68. LRMS (ESI, APCI) m/z: calc'd for C32H39O3 [M−H]− 471.3, found 471.3. Calc'd for C32H39O2 [M−OH]+ 455.3, found 454.8 HRMS (ESI) m/z: calc'd for C32H39O3 [M−H]− 471.28819, found 471.29047. FT-IR (neat): 3360, 3079, 3052, 3019, 2926, 2854, 1708, 1598, 1491, 1441, 1410, 1340, 1279, 1231, 1097, 1073, 1029, 953, 902, 773, 702 cm-1.

12f:
$^{1}$H NMR (500 MHz, CDCl3) δ 7.41-7.12 (m, 10H), 5.07 (d, J=1.4 Hz, 1H), 4.99 (d, J=1.5 Hz, 1H), 3.99-3.92 (s, 1H), 2.38-2.26 (m, 5H), 2.11-1.98 (m, 5H), 1.75-1.58 (m, 6H), 1.36-1.17 (m, 11H). $^{13}$C NMR (126 MHz, CDCl3) δ 179.38, 154.57, 144.15, 141.17, 139.10, 137.37, 129.69, 127.74, 127.71, 127.62, 126.65, 126.59, 114.99, 82.11, 69.33, 55.69, 40.23, 33.99, 33.94, 32.08, 29.65, 29.57, 29.40, 29.33, 29.19, 29.03, 27.76, 24.68. LRMS (ESI, APCI) m/z: calc'd for C33H41O3 [M−H]− 485.3, found 485.3. Calc'd for C33H41O2 [M−OH]+ 469.3, found 468.9 HRMS (ESI) m/z: calc'd for C33H41O3 [M−H]− 485.30612, found 485.30646 FT-IR (neat): 1352, 3079, 3052, 3019, 2925, 2853, 1708, 1598, 1491, 1441, 1410, 1340, 1281, 1230, 1096, 1073, 1029, 954, 902, 773, 702 cm-1.

Synthetic Scheme for [3.3.0] Bicyclic Phosphorylcholines

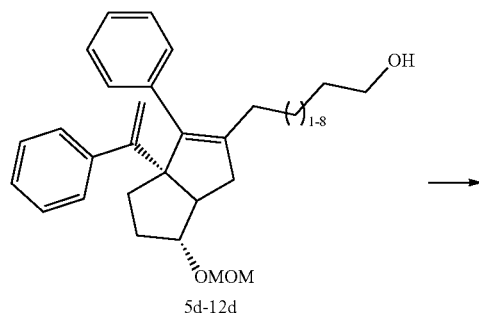

5d-12d

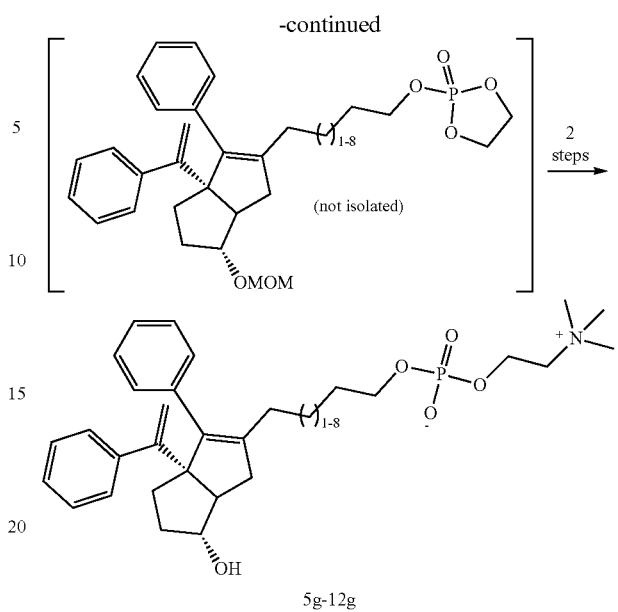

5g-12g

General Procedure for Phosphorylcholines

The required cyclized primary alcohols (5d-12d) (1.0 equiv.) were dissolved in toluene and cooled to 0° C. Triethylamine (2.0 equiv.) was added and the solution was briefly stirred. 2-chloro 1,3,2-dioxaphospholane 2-oxide (2.0 equiv.) was then added dropwise. The reaction mixture was stirred for 4 hours at which time completion was detected by LCMS. The reaction mixture was filtered through a cotton plug to remove the majority of the resulting triethylammonium salts, concentrated in vacuo, and reacted without further purification.

The required cyclized phospholane intermediates (1.0 equiv.) were dissolved in acetonitrile, placed in a pressure tube open to air, equipped a stir bar and frozen at −78° C. Trimethylamine (excess) was condensed into the cold pressure tube, which was then capped and allowed to warm to room temperature before heating to 90° C. for 16 h. After reacting for 16 h, the reaction mixture was cooled to −78° C., uncapped, and allowed to warm to room temperature. The mixture was concentrated in vacuo and carried on without further purification.

Crude material from the previous reaction was dissolved in acetonitrile. Concentrated HCl (5-10 equiv.) was added and the mixture was allowed to stir for 30 minutes at room temperature. When the reaction was complete, as determined by LCMS, the reaction mixture was concentrated in vacuo and subjected to preparatory HPLC to isolate the desired product as the major exo diasteromer.

| Identi-fier | Compound Name |
|---|---|
| 5g | 4-(6-exo-hydroxy-3-phenyl-3a-(1-phenylvinyl)-1,3a,4,5,6,6a-hexahydropentalen-2-yl)butyl (2-(trimethylammonio)ethyl) phosphate |
| 6g | 5-(6-exo-hydroxy-3-phenyl-3a-(1-phenylvinyl)-1,3a,4,5,6,6a-hexahydropentalen-2-yl)pentyl (2-(trimethylammonio)ethyl) phosphate |
| 7g | 6-(6-exo-hydroxy-3-phenyl-3a-(1-phenylvinyl)-1,3a,4,5,6,6a-hexahydropentalen-2-yl)hexyl(2-(trimethylammonio)ethyl) phosphate |

| Identi-fier | Compound Name |
|---|---|
| 8g | 7-(6-exo-hydroxy-3-phenyl-3a-(1-phenylvinyl)-1,3a,4,5,6,6a-hexahydropentalen-2-yl)heptyl (2-(trimethylammonio)ethyl) phosphate |
| 9g | 8-(6-exo-hydroxy-3-phenyl-3a-(1-phenylvinyl)-1,3a,4,5,6,6a-hexahydropentalen-2-yl)octyl (2-(trimethylammonio)ethyl) phosphate |
| 10g | 9-(6-exo-hydroxy-3-phenyl-3a-(1-phenylvinyl)-1,3a,4,5,6,6a-hexahydropentalen-2-yl)nonyl (2-(trimethylammonio)ethyl) phosphate |
| 11g | 10-(6-exo-hydroxy-3-phenyl-3 a-(1-phenylvinyl)-1,3a,4,5,6,6a-hexahydropentalen-2-yl)decyl (2-(trimethylammonio)ethyl) phosphate |
| 12g | 11-(6-exo-hydroxy-3-phenyl-3a-(1-phenylvinyl)-1,3a,4,5,6,6a-hexahydropentalen-2-yl)undecyl (2-(trimethylammonio)ethyl) phosphate |

Characterization Data for Phosphorylcholines (5g-12g)

5g:
$^1$H NMR (500 MHz, CDCl3) δ 7.28-7.13 (m, 10H), 5.02 (s, 1H), 4.99 (s, 1H), 4.19 (s, 2H), 3.81 (s, 1H), 3.76 (s, 2H), 3.64 (s, 2H), 3.21 (s, 9H), 2.26-2.05 (m, 3H), 2.01-1.87 (m, 1H), 1.68-1.36 (m, 9H). 31P NMR (121 MHz, CDCl3) δ −0.76. LRMS (ESI, APCI) m/z: calc'd for C31H43O5NP [M+H]+: 540.3, found 540.3

6g:
$^1$H NMR (600 MHz, CDCl3) δ 7.31-7.24 (m, 4H), 7.25-7.14 (m, 6H), 4.99 (s, 2H), 4.19 (s, 2H), 3.86 (s, 1H), 3.75 (s, 2H), 3.63 (s, 2H), 3.20 (s, 9H), 2.25-2.18 (m, 1H), 2.16-2.04 (m, 2H), 1.95-1.87 (m, 1H), 1.70-1.60 (m, 1H), 1.60-1.52 (m, 4H), 1.53-1.43 (m, 1H), 1.42-1.30 (m, 3H), 1.31-1.18 (m, 2H). $^{31}$P NMR (121 MHz, CDCl3) δ −0.82. LRMS (ESI, APCI) m/z: calc'd for C32H45O5NP [M+H]+: 554.3, found 554.2

7g:
$^1$H NMR (500 MHz, CDCl3) δ 7.41-7.26 (m, 4H), 7.28-7.12 (m, 6H), 5.03 (s, 1H), 5.01 (s, 1H), 4.24 (s, 2H), 3.88 (s, 1H), 3.80-3.67 (m, 4H), 3.28 (s, 9H), 2.28-2.05 (m, 3H), 2.01-1.80 (m, 1H), 1.72-1.49 (m, 3H), 1.40-0.82 (m, 10H). $^{31}$P NMR (121 MHz, Chloroform-d) δ −0.59. LRMS (ESI, APCI) m/z: calc'd for C33H47O5NP [M+H]+ 568.3, found 568.2

8g:
$^1$H NMR (500 MHz, CDCl3) δ 7.37-7.11 (m, 10H), 5.02 (s, 1H), 4.99 (s, 1H), 4.21 (s, 2H), 3.87 (s, 1H), 3.77 (s, 2H), 3.67 (s, 1H), 3.25 (s, 9H), 2.29-2.16 (m, 1H), 2.15-2.02 (m, 2H), 2.00-1.90 (m, 1H), 1.72-1.57 (m, 3H), 1.57-1.48 (m, 3H), 1.37-1.14 (m, 9H). $^{13}$C NMR (300 MHz, CDCl3) δ 154.59, 144.07, 140.89, 139.62, 137.37, 129.56, 127.83, 127.67, 126.64, 114.74, 81.46, 69.08, 66.14, 65.72, 59.20, 55.70, 54.25, 39.99, 34.18, 32.02, 30.77, 29.47, 29.31, 29.17, 27.57, 25.56. 31P NMR (300 MHz, CDCl3) δ −0.51. HRMS (ESI) m/z: calc'd for C34H49O5NP [M+H]+: 582.33429, found 582.33380 IR (cm-1): 3373 (b), 2930, 2854, 1709, 1668, 1598, 1490, 1440, 1343, 1227, 1090.

9g:
$^1$H NMR (600 MHz, CDCl3) δ 7.33-7.15 (m, 10H), 5.00 (s, 1H), 4.96 (s, 1H), 4.22 (s, 2H), 3.89 (s, 1H), 3.81-3.75 (m, 2H), 3.74-3.66 (m, 2H), 3.27 (s, 9H), 2.28-2.17 (m, 2H), 2.10-2.04 (m, 1H), 1.96-1.87 (m, 1H), 1.71-1.58 (m, 3H), 1.57-1.48 (m, 2H), 1.36-1.13 (m, 12H). $^{13}$C NMR (151 MHz, CDCl3) δ 154.59, 144.14, 141.04, 139.50, 137.40, 129.61, 127.78, 127.63, 126.61, 126.55, 114.80, 81.66, 69.23, 66.29, 59.11, 55.61, 54.37, 53.41, 40.05, 37.14, 34.27, 32.02, 30.82, 29.35, 29.17, 28.91, 28.84, 27.47, 25.57, 22.61. $^{31}$P NMR (300 MHz, CDCl3) δ −0.43. LRMS (ESI, APCI) m/z: calc'd for C35H51O5NP [M+H]+ 596.3, found 596.3. HRMS (ESI) m/z: calc'd for C35H51O5NP [M+H]+: 596.34994, found 596.3939 IR (cm-1): 3355 (b), 2927, 2854, 2187, 1669, 1491, 1440, 1227, 1090.

10g:
$^1$H NMR (600 MHz, CDCl3) δ 7.32-7.14 (m, 10H), 5.01 (d, J=7.6 Hz, 1H), 4.95 (d, J=7.9 Hz, 1H), 4.20 (s, 2H), 3.87 (s, 1H), 3.75 (s, 3H), 3.67 (s, 3H), 3.25 (s, 9H), 2.27-2.18 (m, 2H), 2.06-1.98 (m, 2H), 1.94 (p, J=7.0 Hz, 1H), 1.70-1.58 (m, 4H), 1.58-1.48 (m, 3H), 1.36-1.10 (m, 12H). $^{13}$C NMR (126 MHz, CDCl3) δ 154.65, 144.17, 141.06, 139.41, 137.41, 129.65, 127.76, 127.67, 127.62, 126.63, 126.57, 114.85, 81.72, 69.29, 66.24, 65.92, 59.30, 55.66, 54.36, 40.17, 34.15, 32.09, 30.89, 29.51, 29.28, 29.23, 27.66, 27.61, 25.76. 31P NMR (121 MHz, CDCl3) δ −0.73. LRMS (ESI, APCI) m/z: calc'd for C36H53O5NP [M+H]+ 610.4, found 609.8. HRMS (ESI) m/z: calc'd for C36¬H53O5NP [M+H]+: 610.36559, found 610.36552 IR (cm-1): 3372(b), 2926, 2853, 1653, 1491, 1440, 1228, 1090

11g:
$^1$H NMR (600 MHz, CDCl3) δ 7.34-7.14 (m, 10H), 5.03 (d, J=4.9 Hz, 1H), 4.95 (d, J=5.0 Hz, 1H), 4.24 (s, 2H), 3.90 (s, 1H), 3.79 (q, J=6.4 Hz, 2H), 3.74 (s, 2H), 3.28 (s, 9H), 2.34-2.23 (m, 2H), 2.10-1.92 (m, 3H), 1.64 (q, J=10.2, 6.5 Hz, 2H), 1.56 (t, J=7.3 Hz, 2H), 1.37-1.10 (m, 16H). $^{13}$C NMR (126 MHz, CDCl3) δ 154.71, 144.23, 141.07, 139.40, 137.43, 129.69, 127.73, 127.70, 127.60, 126.63, 126.56, 81.67, 69.33, 66.20, 65.87, 59.29, 55.64, 54.31, 40.23, 34.08, 32.18, 30.91, 30.86, 29.55, 29.32, 29.22, 29.17, 27.60, 25.82. $^{31}$P NMR (121 MHz, CDCl3) δ −0.75. LRMS (ESI, APCI) m/z: calc'd for C37H55O5NP [M+H]+: 624.4, found 624.3

12g:
$^1$H NMR (600 MHz, CDCl3) δ 7.35-7.15 (m, 12H), 5.03 (s, 1H), 4.96 (s, 1H), 4.26 (s, 2H), 3.91 (s, 1H), 3.85-3.77 (m, 2H), 3.75 (s, 2H), 3.29 (s, 9H), 2.32 (dd, J=16.7, 9.4 Hz, 1H), 2.26 (d, J=9.6 Hz, 1H), 2.10-1.94 (m, 4H), 1.71-1.61 (m, 3H), 1.61-1.53 (m, 2H), 1.38-1.14 (m, 16H). $^{31}$P NMR (121 MHz, CDCl3) δ −0.90. $^{13}$C NMR (126 MHz, CDCl3) δ 154.72, 144.22, 141.10, 139.32, 137.43, 129.69, 114.91, 81.70, 69.33, 66.20, 65.88, 59.31, 55.67, 54.37, 40.25, 34.02, 32.18, 31.58, 30.91, 30.86, 29.60, 29.51, 29.43, 29.40, 29.36, 29.34, 29.24, 27.65, 25.76, 22.65. LRMS (ESI, APCI) m/z: calc'd for C38H57O5NP [M+H]+ 638.4, found 637.8 HRMS (ESI) m/z: calc'd for C38¬H57O5NP [M+H]+: 638.39689, found 638.39741 FT-IR (neat): 3362 (b), 2924, 2853, 1667, 1490, 1440, 1227, 1090 cm-1.

Synthetic Scheme for Locked Synthetic Phospholipid Mimic (13b)

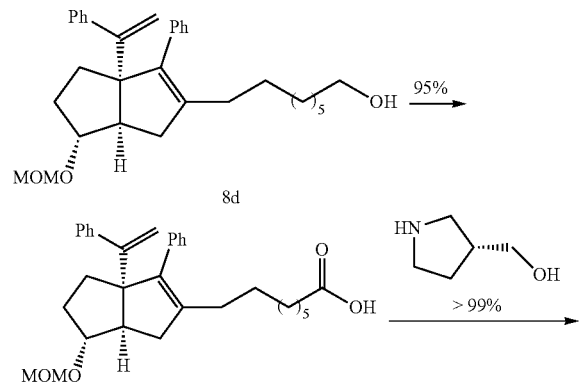

-continued

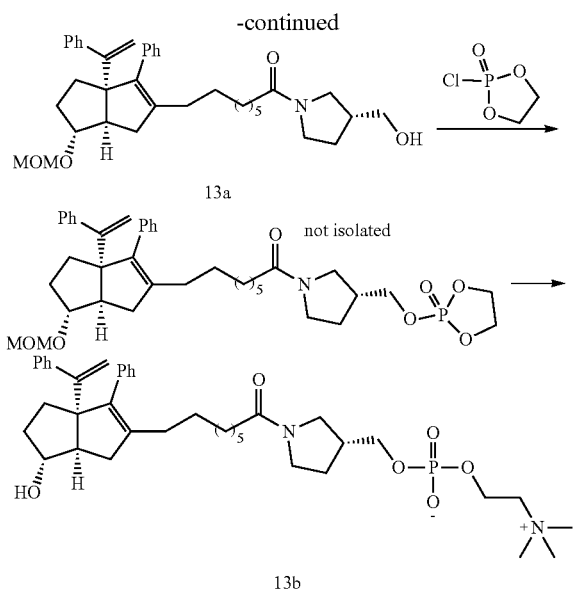

13a

13b

1-((R)-3-(hydroxymethyl)pyrrolidin-1-yl)-8-(6-(exo)-(methoxymethoxy)-3-phenyl-3a-(1-phenylvinyl)-1,3a,4,5,6,6a-hexahydropentalen-2-yl)octan-1-one (13a)

In a reaction tube equipped with a stir bar, 8d was dissolved in acetonitrile. Tetrapropylammonium perruthenate (TPAP, 0.1 equiv.), N-Methylmorpholine-N-Oxide (NMO, 10.0 equiv.), and water (10.0 equiv.) were added. The reaction mixture was allowed to stir until complete by TLC and LCMS, 1-16 h. Upon reaction completion, the reaction mixture was concentrated and subjected directly to silica for purification in 20-50% EtOAc/Hex (0.1% Acetic acid) to afford the desired compound as a clear, colorless oil (96%)

This resulting carboxylic acid was dissolved in DMF in a reaction tube equipped with a stir bar. (2-(1H-benzotriazol-1-yl)-1,1,3,3-tetramethyluronium hexafluorophosphate (HBTU, 1.2 equiv.) was added. (3R)-pyrrolidin-3-ylmethanol (1.2 equiv.) was added in DMF before diisopropylethylamine (2.0 equiv.) was added. The reaction mixture was heated and allowed to stir at 60° C. for 1 h, until complete by LCMS. The mixture was cooled to room temperature before being poured into water and extracted with EtOAc. The combined organic layers were dried with MgSO$_4$ and concentrated before being purified by silica gel chromatography in 100% EtOAc/Hex to afford the desired compound 13a as a clear, colorless oil (99%).

((3R)-1-(8-(6-(exo)-hydroxy-3-phenyl-3a-(1-phenylvinyl)-1,3a,4,5,6,6a-hexahydropentalen-2-yl)octanoyl)pyrrolidin-3-yl)methyl (2-(trimethylammonio)ethyl) phosphate (13b)

In a scintillation vial equipped with a stir bar, 13a was dissolved in toluene. 2-Chloro-1,3,2-dioxaphospholane 2-oxide (2.0 equiv.) was added, followed by triethylamine (2.0 equiv.) The resulting reaction mixture was stirred for 1-4 h, until reaction was complete by TLC. The resulting mixture containing the cyclic phospholane intermediate was filtered over a cotton plug to remove excess ammonium salts and concentrated. The crude reaction mixture was taken up in acetonitrile and transferred into a pressure tube and cooled to −78° C. Trimethylamine (neat, 2-5 mL) was condensed into the pressure tube at −78° C. The tube was capped, allowed to warm to room temperature, and then heated to 90° C. for 16 h. After the reaction was complete, the pressure tube was allowed to cool to R.T. before being further cooled to −78° C. and uncapped. The solution was allowed to re-warm to room temperature before being concentrated inside a fume hood and carried on without further purification. The crude reaction mixture was dissolved in acetonitrile, and 2-5 drops of concentrated HCl was added. The mixture was allowed to stir until the reaction was complete (5-30 min, monitored by LCMS), and then concentrated. The crude reaction mixture was purified on alumina in 65/35/5 CH$_2$Cl2/MeOH/NH$_4$OH to afford the desired compound 13b.

$^1$H NMR (600 MHz, CD3OD) δ 7.37-7.14 (m, 10H), 4.97 (d, J=1.6 Hz, 1H), 4.94 (d, J=1.7 Hz, 1H), 4.27 (s, 2H), 3.94-3.88 (m, 1H), 3.87 (s, 1H), 3.85-3.80 (m, 1H), 3.69-3.64 (m, 2H), 3.63-3.47 (m, 2H), 3.34 (s, 2H), 3.24 (s, 9H), 2.63 (p, J=7.1 Hz, 1H), 2.54 (p, J=7.1 Hz, 1H), 2.35-2.24 (m, 5H), 2.14-2.02 (m, 2H), 2.01 (t, J=8.7, 6.7 Hz, 2H), 1.90-1.80 (m, 1H), 1.79-1.64 (m, 1H), 1.68-1.59 (m, 2H), 1.59-1.45 (m, 2H), 1.40-1.17 (m, 7H). $^{13}$C NMR (151 MHz, CD3OD) δ 172.47, 155.17, 144.09, 140.82, 139.49, 137.35, 129.41, 127.54, 127.26, 126.34, 113.56, 81.37, 69.28, 66.46, 66.18, 66.02, 59.02, 55.08, 53.28, 45.99, 44.89, 39.84, 34.02, 33.82, 33.12, 31.72, 29.13, 29.10, 28.95, 28.91, 28.79, 28.75, 27.80, 27.30, 27.28, 26.19, 24.60, 24.59. LRMS (ESI, APCI) m/z: calc'd for C40H58N$_2$O6P [M+H]+: 693.4, found 693.6 HRMS (ESI) m/z: calc'd for C40H58N$_2$O6P [M+H]+ 693.40300, found 693.40270.

Synthetic Procedure for Phospholipid Mimic 14d

The synthetic procedure for preparing compound 14d is provided for in FIG. 7.

(R)-3-((tert-butyldiphenylsilyl)oxy)-2-hydroxypropyl 8-(6-(exo)-(methoxymethoxy)-3-phenyl-3a-(1-phenylvinyl)-1,3a,4,5,6,6a-hexahydropentalen-2-yl) octanoate (14a)

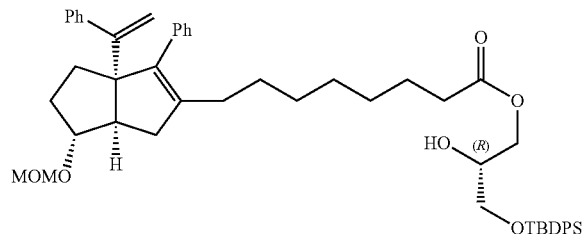

14a

In a scintillation vial equipped with stir bar, 8d was dissolved in acetonitrile. Tetrapropylammonium perruthenate (TPAP, 0.1 equiv.), N-Methylmorpholine-N-Oxide (NMO, 10.0 equiv.), and water (10.0 equiv.) were added. The reaction mixture was allowed to stir until complete by TLC and LCMS, 1-16 h. Upon reaction completion, the reaction mixture was concentrated and subjected directly to silica for purification in 20-50% EtOAc/Hex (0.1% Acetic acid) to afford the desired compound as a clear, colorless oil (96%). In a reaction tube equipped with a stir bar, (R)-tertbutyl(oxiran-2-ylmethoxy)diphenylsilane was dissolved in diethyl ether. Co[Salen] (S,S)-(+)-N,N'bix(3,5-di-tert-butyl salicylidene)-1,2-cyclohexanediamono cobalt (II) (0.01 equiv.) was added and the reaction was allowed to stir for 1 h open to air to activate. After 1 h, the diethylether was evaporated. The previously prepared carboxylic acid (1.0 equiv.) and diisopropylethylamine (1.0 equiv.) was added to the reaction tube and the reaction was allowed to stir, neat, at room temperature for 3-16 h, until complete by TLC and LCMS. When reaction was determined to be complete, the crude reaction mixture was directly purified by silica gel chromatography in 5-10% EtOAc/Hex to afford the desired compound 14a (28%).

(R)-3-((tert-butyldiphenylsilyl)oxy)-2-(propiony-loxy)propyl 8-(6-(exo)-(methoxymethoxy)-3-phe-nyl-3a-(1-phenylvinyl)-1,3a,4,5,6,6a-hexahydropen-talen-2-yl)octanoate (14b)

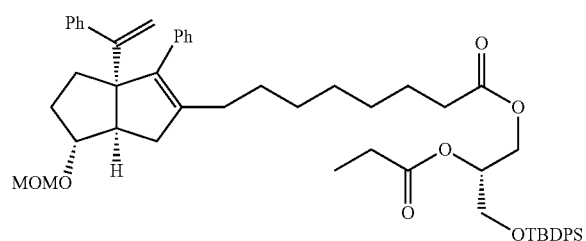

14b

In a scintillation vial equipped with a stir bar, 14a was dissolved in DCM. Propionyl chloride (4.0 equiv.) was added at room temperature, followed by triethylamine (4.0 equiv.). The reaction was allowed to stir until complete by TLC (4 h). The resulting reaction mixture was concentrated and purified by silica gel chromatography in 5-10% EtOAc/Hex to afford the desired compound 14b (74%).

(S)-3-hydroxy-2-(propionyloxy)propyl 8-(6-(exo)-(methoxymethoxy)-3-phenyl-3a-(1-phenylvinyl)-1,3a,4,5,6,6a-hexahydropentalen-2-yl)octanoate (14c)

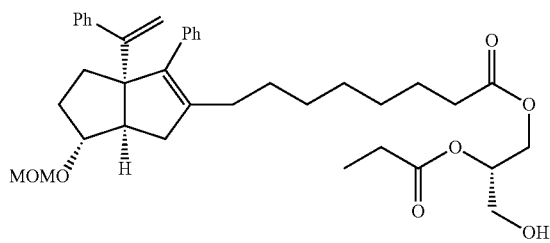

14c

In a scintillation vial equipped with a stir bar, 14b was dissolved in THF. Tetrabutylammoniumfluoride (1.1 equiv.) was added, and the reaction mixture was allowed to stir for 16 h. The resulting mixture was concentrated and purified by silica gel chromatography in 20-50% EtOAc/Hex to afford the desired compound 14c (>99%).

(2R)-3-((8-(6-(exo)-hydroxy-3-phenyl-3a-(1-phenyl-vinyl)-1,3a,4,5,6,6a-hexahydropentalen-2-yl)oc-tanoyl)oxy)-2-(propionyloxy)propyl (2-(trimethyl-ammonio)ethyl) phosphate (14d)

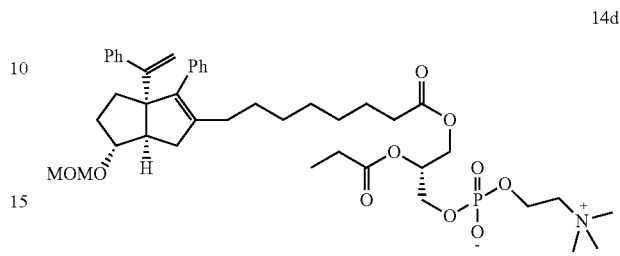

14d

In a scintillation vial equipped with a stir bar, 14c was dissolved in toluene. 2-Chloro-1,3,2-dioxaphospholane 2-oxide (2.0 equiv.) was added, followed by triethylamine (2.0 equiv.) The resulting reaction mixture was stirred for 1-4 h, until reaction was complete by TLC. The resulting mixture containing the cyclic phospholane intermediate was filtered over a cotton plug to remove excess ammonium salts and concentrated. The crude reaction mixture was taken up in acetonitrile and transferred into a pressure tube and cooled to −78° C. Trimethylamine (neat, 2-5 mL) was condensed into the pressure tube at −78° C. The tube was capped, allowed to warm to room temperature, and then heated to 90° C. for 16 h. After the reaction was complete, the pressure tube was allowed to cool to R.T. before being further cooled to −78° C. and uncapped. The solution was allowed to re-warm to room temperature before being concentrated inside a fume hood and carried on without further purification. The crude reaction mixture was dissolved in acetonitrile, and 2-5 drops of concentrated HCl was added. The mixture was allowed to stir until the reaction was complete (5-30 min, monitored by LCMS), and then concentrated. The crude reaction mixture was purified via preparatory HPLC to afford the desired compound 14d.

$^1$H NMR (600 MHz, CDCl3) δ 7.37-7.15 (m, 10H), 5.04 (s, 1H), 4.98 (s, 1H), 4.51 (s, OH), 4.44-4.28 (m, 4H), 4.28-4.17 (m, 2H), 4.18-4.06 (m, 1H), 3.92 (s, 1H), 3.80-3.69 (m, 2H), 3.30 (s, 9H), 2.38-2.22 (m, 6H), 2.12-1.93 (m, 4H), 1.60-1.48 (m, 4H), 1.38-1.13 (m, 9H), 1.10 (t, J=7.5 Hz, 3H). LRMS (ESI, APCI) m/z: calc'd for C41 [M]+ 739.4, found 739.6 HRMS (ESI) m/z: calc'd for C41H59O9NP [M+H]+ 740.39393, found 740.39220. Calc'd for C41H48O9NPNa [M+Na]+ 762.37569, found 762.37414. FT-IR (neat): 3357, 3079, 3020, 2925, 2854, 1736, 1715, 1686, 1618, 1598, 1555, 1490, 1463, 1440, 1363, 1250, 1201, 1175, 1085, 1025, 967, 912, 800, 760, 702 cm-1.

Synthetic Scheme for Internal Styrene Modifications (15f-18f, 15g-18g)

Figure 1D:
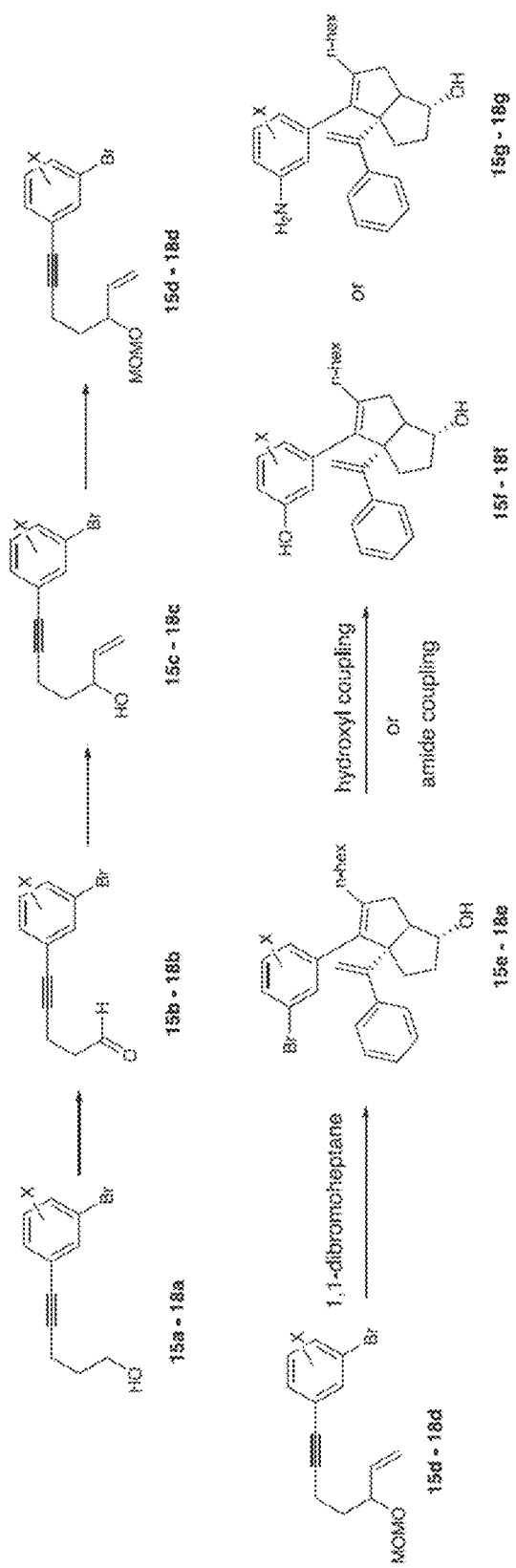
FIG. 1D shows a scheme for the production of compounds disclosed herein.
Figure 2A:
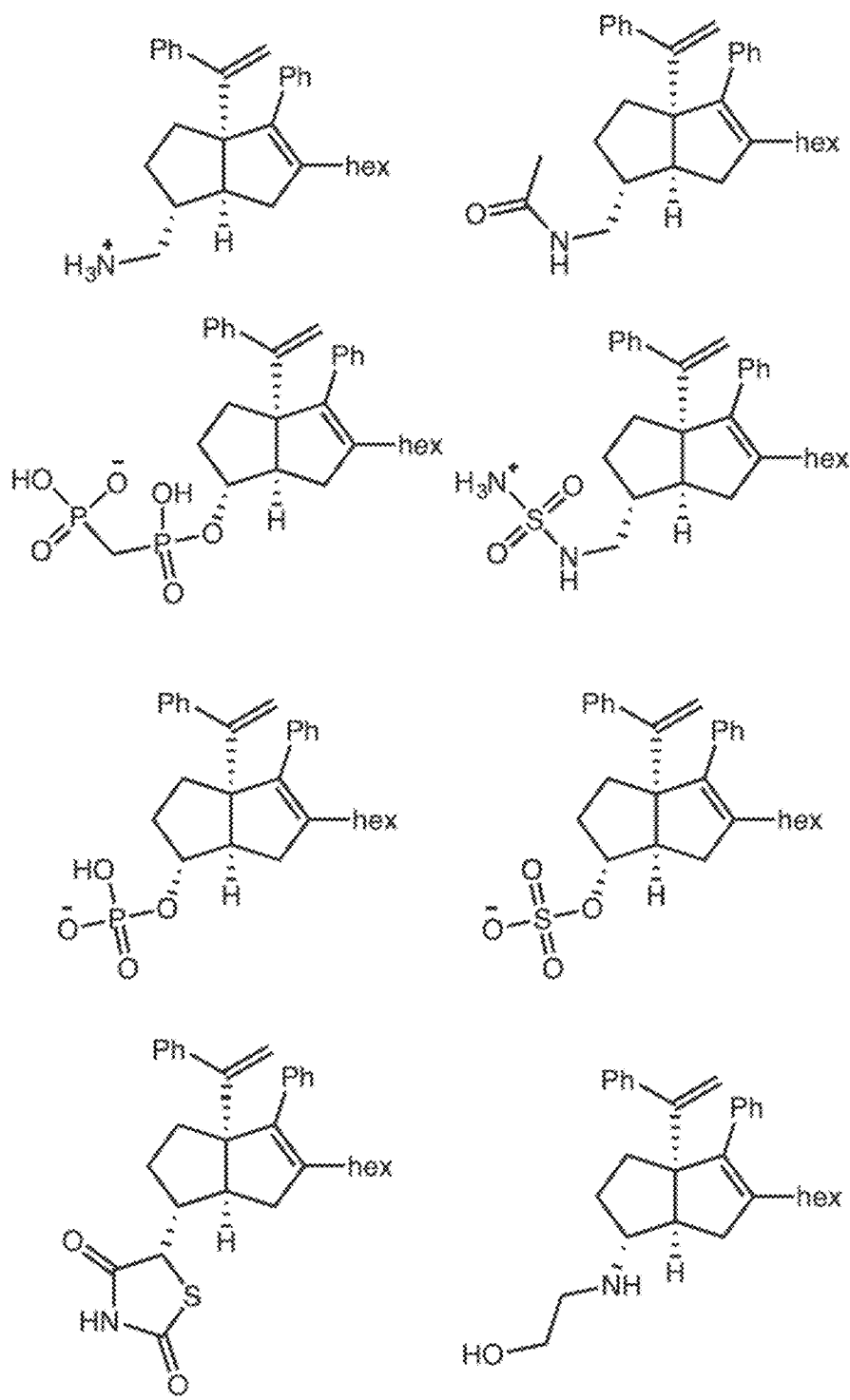
FIG. 2A illustrates additional embodiments of this disclosure.
Figure 2B:
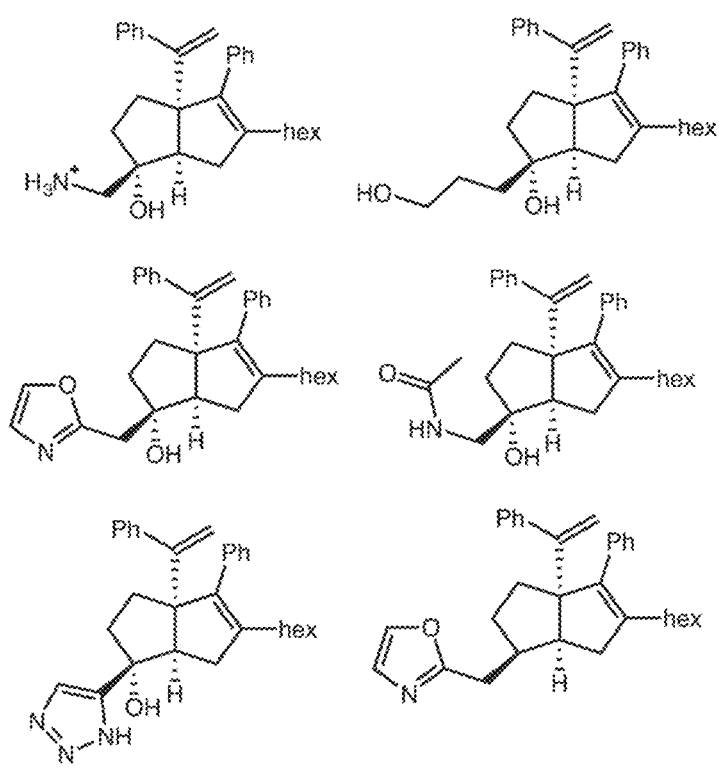
FIG. 2B illustrates additional embodiments of this disclosure.

The synthetic procedure for preparing compounds 15f-18f, 15g-18g is provided for in FIG. 1D.

General Sonogashira Coupling Procedure (15a-18b)

To an oven-dried round bottom flask was added bis(triphenylphosphine)palladium dichloride (0.03 equiv.) and copper iodide (0.06 equiv.). Triethylamine was added to make a 1.0 M solution before the addition of required aryl halide (1.0 equiv.) The resulting yellow mixture was sparged by bubbling the solution with nitrogen for a period of 30 minutes, at which point 4-pentyl-1-ol (1.2 equiv.) was added portionwise and the sparging needle was replaced with a nitrogen inlet. The solution rapidly darkened and formed a slurry, and was heated at 60° C. for 2 hours, at which point the reaction was complete by TLC. The resulting black solution was cooled and ether was added to precipitate a black solid. The resulting slurry was filtered over a plug of celite and eluted with ether. The filtrate was concentrated in vacuo to afford a reddish-brown oil, which was then purified on silica in 30% EtOAc/hex to afford a yellow oil.

5-(3-bromophenyl)pent-4-yn-1-ol (15a)

The general Sonogashira coupling procedure was followed using 1-bromo-3-iodobenzene as the aryl halide. The compound was purified in 10-30% EtOAc/Hex (3.1 g 92%).

5-(5-bromo-2-fluorophenyl)pent-4-yn-1-ol (16a)

The general Sonogashira coupling procedure was followed using 4-bromo-1-fluoro-2-iodobenzene as the aryl halide. The compound was purified in 10-30% EtOAc/Hex (3.9 g, 75%).

5-(5-bromo-2-methylphenyl)pent-4-yn-1-ol (17a)

The general Sonogashira coupling procedure was followed using 4-methyl-2-iodo-1-methylbenzene as the aryl halide. The compound was purified in 10-30% EtOAc/Hex as the eluent, (3.6 g, 81%).

5-(3-bromo-5-fluorophenyl)pent-4-yn-1-ol (18a)

The general Sonogashira coupling procedure was followed using 1-bromo-3-fluoro iodobenzene as the aryl halide. The compound was purified in 20% EtOAc/Hex (3.5 g 90%).

General Swern Oxidation Procedure (15b-18b)

To an oven-dried three-neck roundbottom flask charged with a stir bar was added oxalyl chloride (1.1 equiv.) in DCM (0.1M). The solution was cooled to −78° C. before the dropwise addition of dimethylsulfoxide (1.3 equiv.) in DCM. After effervescence ceased, the required alcohol (1.0 equiv.) was added dropwise in DCM. The reaction mixture was stirred at −78° C. for 1.5 h before quenching with triethylamine (2.5 equiv.) and allowing to warm to room temperature before additional quenching with saturated ammonium chloride. The reaction mixture was then poured over water and extracted with DCM, dried with $MgSO_4$, concentrated, and purified by silica gel chromatography to afford a (typically pale yellow) oil.

5-(3-bromophenyl)pent-4-ynal (15b)

The general procedure for Swern oxidation was followed, using 5-(3-bromophenyl)pent-4-yn-1-ol as the alcohol. The crude oil was purified on silica gel with 10-50% EtOAc/Hex (3.4 g, 81%).

5-(5-bromo-2-fluorophenyl)pent-4-ynal (16b)

The general procedure for Swern oxidation was followed, using 5-(5-bromo-2-fluorophenyl)pent-4-yn-1-ol as the alcohol. The crude oil was purified on silica gel with 10-20% EtOAc/Hex (2.4 g, 62%).

5-(5-bromo-2-methylphenyl)pent-4-ynal (17b)

The general procedure for Swern oxidation was followed using 5-(5-bromo-2-methylphenyl)pent-4-yn-1-ol as the alcohol. The crude oil was purified on silica gel with 10% EtOAc/Hex (0.6 g, 17%).

5-(3-bromo-5-fluorophenyl)pent-4-ynal (18b)

The general procedure for Swern oxidation was followed, using 5-(3-bromo fluorophenyl)pent-4-yn-1-ol as the alcohol. The crude oil was purified on silica gel with 10-20% EtOAc/Hex, (3.5 g, 90

General Procedure for Grignard Addition (15c-18c)

To an oven-dried 3-neck flask equipped with a stir bar was added the required aldehyde (1.0 equiv.) in THF. The solution was cooled to −78° C. before the addition of vinylmagnesium bromide (1.5 equiv.). The reaction was stirred and allowed to warm to room temperature overnight before quenching with saturated ammonium chloride. The reaction mixture was poured over water and extracted with ethyl acetate, dried with MgSO4, and concentrated before being purified by silica gel chromatography.

7-(3-bromophenyl)hept-1-en-6-yn-3-ol (15c)

The general procedure for Grignard addition was followed, using 5-(3-bromophenyl)pent-4-ynal as the aldehyde. The crude oil was then purified on silica gel with 5-10% EtOAc/Hex, (1.12 g, 55%).

7-(5-bromo-2-fluorophenyl)hept-1-en-6-yn-3-ol (16c)

The general procedure for Grignard addition was followed, using 5-(5-bromo-2-fluorophenyl)pent-4-ynal as the aldehyde. The crude oil was then purified on silica gel with 20% EtOAc/Hex, (3.3 g, 90%)

7-(5-bromo-2-methylphenyl)hept-1-en-6-yn-3-ol (17c)

The general procedure for Grignard addition was followed, using 5-(5-bromo-2-methylphenyl)pent-4-ynal as the aldehyde. The crude oil was then purified on silica gel with 20% EtOAc/Hex, (1.4 g, 60%).

7-(3-bromo-5-fluorophenyl)hept-1-en-6-yn-3-ol (18c)

The general procedure for Grignard addition was followed, using 5-(3-bromo fluorophenyl)pent-4-yn-1-ol as the aldehyde. The crude oil was then purified on silica gel with 20% EtOAc/Hex, (3.0 g, 81%).

General Protection Procedures and Characterization Data for Protected Enynes (15d-18d, 19)

Tert-butyldimethyl((7-phenylhept-1-en-6-yn-3-yl)oxy)silane (19): In an oven-dried three-neck flask equipped with stir bar and flushed with nitrogen was added imidazole (4.0 equiv.) and 4-dimethylaminopyridine (2.0 equiv.). After further evacuation and backfilling with nitrogen, the solids were dissolved in dry THF and cooled to −78° C. Following addition of a solution of the alcohol (1.0 equiv.) in THF, tert-butyldimethylsilyl triflate (2.0 equiv.) was added dropwise, and allowed to stir for 6 hours. The reaction was then quenched by saturated aqueous NH4Cl, and extracted with ether (3×); the combined organic layers were washed with brine, dried over MgSO4, filtered and concentrated in vacuo. The residue was purified by silica gel chromatography in 5-10% EtOAc/Hex to afford a clear yellow oil (8.0 g, 99% yield). The spectral data reported are consistent with literature.

General procedure for alcohol protection with methoxymethyl (MOM) ether (15d-18d) The required unprotected enyne (15c-18c) (1.0 equiv.) was dissolved in DCM, followed by diisopropylethyl amine (1.25 equiv.) Chloromethyl methyl ether (1.5 equiv.) was added and the reaction mixture was stirred at 30° C. until completion (typically 1-4 hours). The reaction mixture was cooled to room temperature before being poured onto water, washed with dilute HCl (1 M), and extracted with DCM. The organic layers were dried with MgSO4, filtered, and concentrated before being subjected to silica gel chromatography.

1-bromo-3-(5-(methoxymethoxy)hept-6-en-1-yn-1-yl)benzene (15d)

The general procedure for MOM ether protection was followed, using 7-(3-bromophenyl)hept-1-en-6-yn-3-ol as the enyne. The crude oil was purified in 5% EtOAc/Hex (2.1 g, 92%).

4-bromo-1-fluoro-2-(5-(methoxymethoxy)hept-6-en-1-yn-1-yl)benzene (16d)

The general procedure for MOM ether protection was followed, using 7-(5-bromo-2-fluorophenyl)hept-1-en-6-yn-3-ol as the enyne. The crude oil was purified in 2-10% EtOAc/Hex (1.1 g, 88%).

4-bromo-2-(5-(methoxymethoxy)hept-6-en-1-yn-1-yl)-1-methylbenzene (17d)

The general procedure for MOM ether protection was followed, using 7-(5-bromo methylphenyl)hept-1-en-6-yn-3-ol as the enyne. The crude oil was purified in 2-10% EtOAc/Hex (0.2 g, 78%).

1-bromo-3-fluoro-5-(5-(methoxymethoxy)hept-6-en-1-yn-1-yl)benzene (18d)

The general procedure for MOM ether protection was followed, using 7-(3-bromo-5-fluorophenyl)hept-1-en-6-yn-3-ol as the enyne. The crude oil was purified in 2-10% EtOAc/Hex (1.0 g, 77%).

General Procedure for Zirconocene Mediated Cyclization and MOM Deprotection (15e-18e)

Bis(cyclopentadienyl)zirconium(IV) dichloride (zirconecene dichloride) (1.2 equiv.) was dried by azeotroping away latent water with benzene four times before being placed under nitrogen, dissolved in tetrahydrofuran (THF) and cooled to −78° C. in a dry ice/acetone bath. The resulting solution of zirconecene dichloride was treated with nBuLi (2.4 equiv.) to form a clear, light yellow solution and allowed to stir. After approximately 30 minutes, azeotroped required enyne (1.0 equiv.) in dry THF was added portionwise to afford a red-orange solution, and the reaction mixture was held at −78° C. for 30 minutes before allowing to warm to room temperature and stir over 2.5 hours. The reaction mixture was then re-cooled to −78° C. and 1,1-dibromoheptane (1.1 equiv.) were added in dry THF. Freshly prepared lithium diisopropylamine (LDA, 1.0 M, 1.1 equiv.) was added at −78° C. and stirred for 15 minutes. Lithium phenylacetylide (3.6 equiv.) was then prepared and added to the reaction mixture dropwise in dry THF¬. The resulting dark reddish brown solution was stirred at −78° C. for one hour. The reaction was then quenched with methanol and saturated aqueous sodium bicarbonate and allowed to warm to room temperature to form a light yellow slurry. The resulting slurry was poured over water and extracted with ethyl acetate four times. The combined organic layers were washed with brine, dried with MgSO4, and concentrated in vacuo. The resulting colored oil (typically yellow, orange, or brown), was roughly purified on a plug of silica and eluted with 20% EtOAc/Hex to afford a yellow oil which is a mixture of phenylacetylene, desired protected [3.3.0] bicyclic compounds, and (in some cases) protected protonolysis byproduct. This oil was carried on without further purification. This procedure affords exo and endo diastereomers in a 7:1 ratio as determined by characteristic 1H NMR signals.

The crude mixture (1.0 equiv.) was dissolved in acetonitrile and a few drops of concentrated HCl (excess) was added. The resulting dark blue-purple solution was stirred open to air for approximately 30 minutes (monitored via LCMS), concentrated, and subjected directly to silica gel chromatography in 5-20% EtOAc/Hexanes to afford the desired compound as a pale yellow oil.

(exo)-4-(3-bromophenyl)-5-hexyl-3a-(1-phenylvinyl)-1,2,3,3a,6,6a-hexahydropentalen-1-ol (15e)

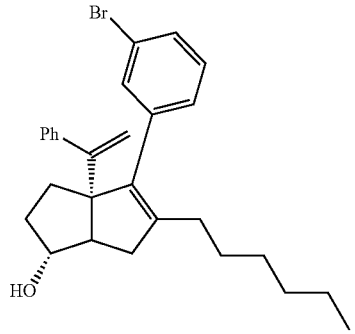 [SMILES: C=C(c1ccccc1)[C@@]12CC[C@@H](O)C1CC(CCCCCC)=C2c1cccc(Br)c1]

The general procedure for zirconecene mediated cyclization and MOM deprotection was followed, using 1-bromo-3-(5-(methoxymethoxy)hept-6-en-1-yn-1-yl)benzene as the enyne. The crude oil was purified by silica gel chromatography in 5-20% EtOAc/Hex (exo)-4-(5-amino-2-fluorophenyl)-5-hexyl-3a-(1-phenylvinyl)-1,2,3,3a,6,6a-hexahydropentalen-1-ol (16e)

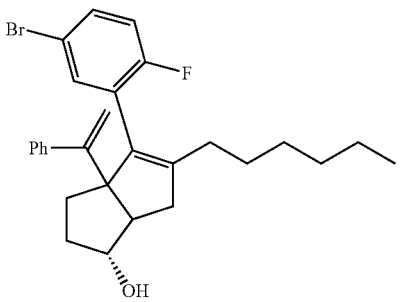 [SMILES: C=C(c1ccccc1)C12CC[C@@H](O)C1CC(CCCCCC)=C2c1cc(Br)ccc1F]

The general procedure for zirconecene mediated cyclization and MOM deprotection was followed, using 4-bromo-1-fluoro-2-(5-(methoxymethoxy)hept-6-en-1-yn-1-yl)benzene as the enyne. The crude oil was purified by silica gel chromatography in 5-20% EtOAc/Hex, affording both the desired compound and lithium-halogen exchange byproduct in an appreciable amount. This mixture was carried on without further purification.

(exo)-4-(5-bromo-2-methylphenyl)-5-hexyl-3a-(1-phenylvinyl)-1,2,3,3a,6,6a-hexahydropentalen-1-ol (17e)

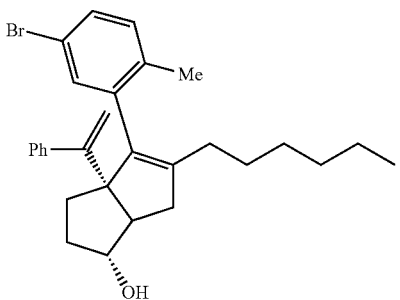 [SMILES: C=C(c1ccccc1)[C@@]12CC[C@@H](O)C1CC(CCCCCC)=C2c1cc(Br)ccc1C]

The general procedure for zirconecene mediated cyclization and MOM deprotection was followed, using 4-bromo-2-(5-(methoxymethoxy)hept-6-en-1-yn-1-yl)-1-methylbenzene as the enyne. The crude oil was purified by silica gel chromatography in 5-20% EtOAc/Hex.

(exo)-4-(3-bromo-5-fluorophenyl)-5-hexyl-3a-(1-phenylvinyl)-1,2,3,3a,6,6a-hexahydropentalen-1-ol (18e)

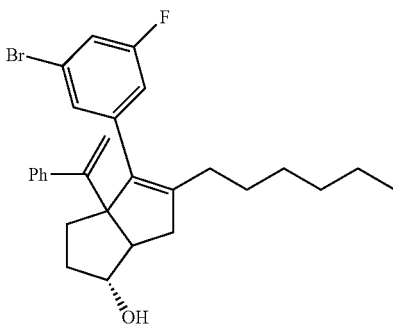 [SMILES: C=C(c1ccccc1)C12CC[C@@H](O)C1CC(CCCCCC)=C2c1cc(F)cc(Br)c1]

The general procedure for zirconecene mediated cyclization and MOM deprotection was followed, using 1-bromo-3-fluoro-5-(5-(methoxymethoxy)hept-6-en-1-yn-1-yl)benzene as the enyne. The crude oil was purified by silica gel chromatography in 5-10% EtOAc/Hex, affording both the desired compound and lithium-halogen exchange byproduct in an appreciable amount. This mixture was carried on without further purification.

General Procedure for Hydroxyl Coupling (15f-18f)

Potassium Hydroxide (3.0 equiv.), tris(dibenzylideneacetone)dipalladium(0) (0.01 equiv.), and tBuXPhos (0.04 equiv.) were placed in a reaction tube, which was evacuated and backfilled with nitrogen three times. The solids were then suspended in degassed 1,4-dioxane under nitrogen. The required brominated [3.3.0] bicycle was added in 1,4-dioxane. Water (~10 equiv.) was added. The reaction mixture was heated to 80° C. and stirred for 16 hours. After stirring, the mixture was poured over water and EtOAc, and the organics were washed with water and brine to remove 1,4-dioxane. The combined organic layers were dried with MgSO4, concentrated, and purified on silica in 20% EtOAc/Hex.

(exo)-5-hexyl-4-(3-hydroxyphenyl)-3a-(1-phenylvinyl)-1,2,3,3a,6,6a-hexahydropentalen-1-ol (15f)

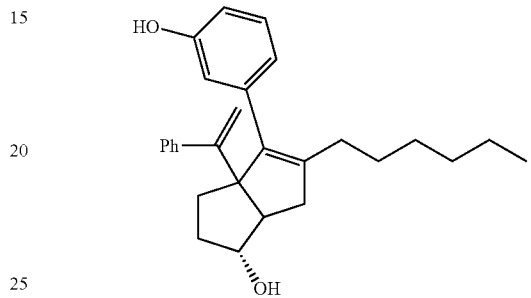

The general procedure for hydroxyl coupling was followed, using (exo)-6 (3-bromophenyl)-5-hexyl-3-(methoxymethoxy)-6a-(1-phenylvinyl)-1,2,3,3a,4,6a-hexahydropentalen-1-ol as the brominated [3.3.0] bicycle. The crude oil was purified by silica gel chromatography in 20% EtOAc/Hex.

$^1$H NMR (500 MHz, CDCl3) δ 7.30 (d, J=41.7 Hz, 5H), 7.17 (t, J=7.8 Hz, 1H), 6.75 (t, J=9.3 Hz, 2H), 6.69 (s, 1H), 5.07 (s, 1H), 5.02 (s, 1H), 4.88 (s, 1H), 3.94 (s, 1H), 2.35 (dd, J=17.3, 8.0 Hz, 1H), 2.27 (d, J=9.4 Hz, 1H), 2.05 (dt, J=21.8, 6.9 Hz, 4H), 1.77-1.48 (m, 5H), 1.35-1.16 (m, 8H), 0.86 (t, J=7.0 Hz, 3H). $^{13}$C NMR (126 MHz, CDCl3) δ 154.91, 154.57, 144.10, 141.44, 139.08, 138.57, 128.78, 127.72, 126.68, 122.42, 116.44, 115.08, 113.58, 82.06, 69.30, 55.82, 40.24, 34.00, 32.06, 31.66, 29.74, 29.39, 27.92, 27.78, 22.59, 14.08. LRMS (ESI, APCI) m/z: calc'd for C28H37O2 [M+H]+ 404.3, found 403.8 FTIR (neat): 3368, 3080, 2955, 2928, 2858, 1690, 1598, 1580, 1448, 1200, 1070, 755, 690 cm-1.

(exo)-4-(2-fluoro-5-hydroxyphenyl)-5-hexyl-3a-(1-phenylvinyl)-1,2,3,3a,6,6a-hexahydropentalen-1-ol (16f)

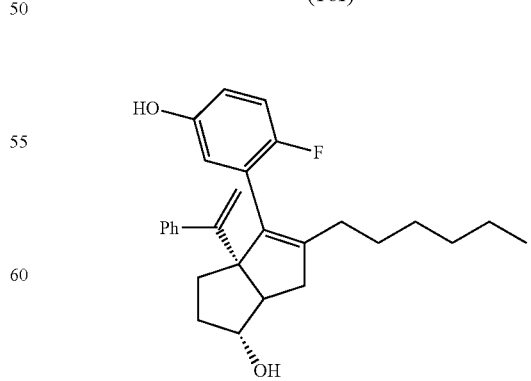

The general procedure for hydroxyl coupling was followed, using (exo)-4-(5-amino-2-fluorophenyl)-5-hexyl-3a-

(1-phenylvinyl)-1,2,3,3a,6,6a-hexahydropentalen-1-ol as the brominated [3.3.0] bicycle. The crude oil was purified by silica gel chromatography in 20% EtOAc/Hex.

¹H NMR (500 MHz, CDCl3δ 7.39-7.35 (m, 2H), 7.31-7.27 (m, 3H), 6.93 (t, J=8.8 Hz, 1H), 6.70 (dt, J=8.6, 3.5 Hz, 1H), 6.65 (dd, J=5.6, 3.2 Hz, 1H), 5.10 (d, J=1.2 Hz, 1H), 4.93 (d, J=1.3 Hz, 1H), 4.61 (s, 1H), 3.97 (s, 1H), 2.52 (dd, J=17.3, 9.7 Hz, 1H), 2.30 (d, J=9.7 Hz, 1H), 2.12-2.03 (m, 2H), 1.95 (t, J=7.8 Hz, 2H), 1.87-1.78 (m, 1H), 1.73 (dd, J=12.3, 6.3 Hz, 1H), 1.68 (dd, J=13.1, 5.9 Hz, 1H), 1.45-1.27 (m, 2H), 1.29-1.16 (m, 6H), 0.86 (t, J=7.1 Hz, 3H). ¹³C NMR (126 MHz, CDCl3) δ 156.08, 154.54, 154.20, 150.56, 144.43, 143.62, 127.89, 127.41, 126.77, 117.66, 117.63, 115.85, 115.65, 115.51, 114.92, 114.85, 81.94, 69.60, 55.39, 40.57, 33.57, 33.09, 31.63, 30.00, 29.39, 27.23, 22.59, 14.09. ¹⁹F NMR (282 MHz, cdcl3) δ −124.47. LRMS (ESI, APCI) m/z: calc'd for C28H36FO2 [M+H]+ 422.3, found 421.9 FTIR (neat): 3358, 3081, 2955, 2929, 2856, 1737, 1491, 1443, 1204, 772, 703 cm-1.

(exo)-5-hexyl-4-(5-hydroxy-2-methylphenyl)-3a-(1-phenylvinyl)-1,2,3,3a,6,6a-hexahydropentalen-1-ol
(17f)

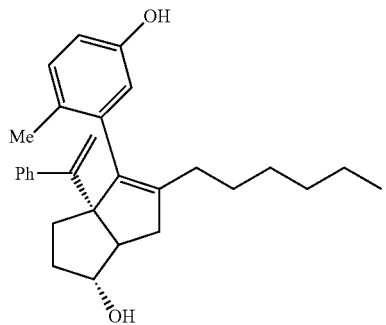 [SMILES: C=C(c1ccccc1)[C@@]12CC[C@@H](O)C1CC(CCCCCC)=C2c1cc(O)ccc1C]

The general procedure for hydroxyl coupling was followed, using (exo)-4-(5-bromo-2-methylphenyl)-5-hexyl-3a-(1-phenylvinyl)-1,2,3,3a,6,6a-hexahydropentalen-1-ol as the brominated [3.3.0] bicycle. The crude oil was purified by silica gel chromatography in 20% EtOAc/Hex.

¹H NMR (500 MHz, Chloroform-d) δ 7.46-7.39 (m, 2H), 7.31-7.27 (m, 3H), 7.09 (d, J=8.3 Hz, 1H), 6.67 (dd, J=8.3, 2.8 Hz, 1H), 6.56 (d, J=2.8 Hz, 1H), 5.20 (d, J=1.1 Hz, 1H), 4.88 (d, J=1.2 Hz, 1H), 4.52 (s, 1H), 3.99 (s, 1H), 3.49 (s, 3H), 2.64 (dd, J=17.3, 10.2 Hz, 1H), 2.33 (d, J=9.5 Hz, 1H), 2.10-1.99 (m, 3H), 1.94-1.77 (m, 3H), 1.71 (ddd, J=19.1, 13.3, 6.6 Hz, 2H), 1.42-1.12 (m, 7H), 0.85 (t, J=7.1 Hz, 3H).

(exo)-4-(3-fluoro-5-hydroxyphenyl)-5-hexyl-3a-(1-phenylvinyl)-1,2,3,3a,6,6a-hexahydropentalen-1-ol
(18f)

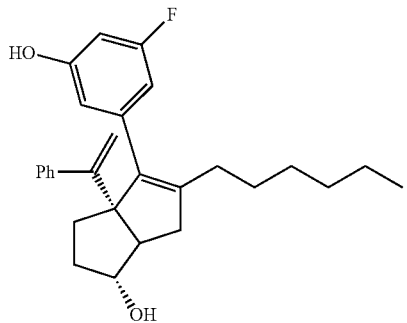 [SMILES: C=C(c1ccccc1)[C@@]12CC[C@@H](O)C1CC(CCCCCC)=C2c1cc(O)cc(F)c1]

The general procedure for hydroxyl coupling was followed, using (exo)-4-(3-bromo-5-fluorophenyl)-5-hexyl-3a-(1-phenylvinyl)-1,2,3,3a,6,6a-hexahydropentalen-1-ol as the brominated [3.3.0] bicycle. The crude oil was purified by silica gel chromatography in 20% EtOAc/Hex.

¹H NMR (500 MHz, CDCl3) δ 7.35-7.28 (m, 2H), 7.26 (d, J=6.2 Hz, 3H), 6.55-6.45 (m, 3H), 5.09 (s, 1H), 5.04 (s, 1H), 4.94 (s, 1H), 3.93 (s, 1H), 2.35 (dd, J=17.0, 9.3 Hz, 1H), 2.28 (d, J=9.5 Hz, 1H), 2.15-1.99 (m, 4H), 1.73-1.64 (m, 3H), 1.38-1.18 (m, 6H), 0.90-0.83 (m, 3H). ¹³C NMR (126 MHz, CDCl3) δ 162.01, 156.16, 154.36, 143.86, 142.29, 137.75, 127.79, 127.67, 126.79, 115.30, 112.38, 109.15, 108.98, 101.67, 101.48, 81.99, 69.26, 55.79, 40.23, 34.00, 32.02, 31.64, 29.71, 29.39, 27.71, 22.59, 14.08. ¹⁹F NMR (282 MHz, cdcl3) δ −112.75. LRMS (ESI, APCI) m/z: calc'd for C28H36FO2 [M+H]+ 423.3, found 422.9 FTIR (neat): 3340, 3075, 2960, 2931, 1738, 1618, 1583, 1448, 1352, 1217, 1002, 668 cm-1.

General Procedure for Amination (15g-18g)

A reaction tube (A) equipped with a magnetic stir bar was charged with tBuBrettPhos (0.04 equiv.) and sodium tert butoxide (3.0 equiv.) before being evacuated and backfilled with nitrogen. The required brominated [3.3.0] bicycle was added in dioxane before ammonia in dioxane (10 equiv.) was added and allowed to stir for ~15 minutes. During this period in a separate reaction tube (B), tBuBrettPhos precatalyst (0.04 equiv.) was added, and the tube was evacuated and backfilled with nitrogen. The tBuBrettPhos precatalyst was then dissolved in dry, degassed dioxane. The solution of tBuBrettPhos precatalyst in reaction tube B was transferred to the stirring reaction mixture in reaction tube A. The nitrogen inlet was removed and the reaction mixture was heated to 80° C. for 16 hours behind a blast shield. After stirring, the mixture was cooled to room temperature, diluted with water and extracted with EtOAc. The organics were washed with water and brine to remove dioxane, dried over MgSO4, and concentrated in vacuo. The crude oil was purified by silica gel chromatography in (typically 20-30%) EtOAc/Hex.

(exo)-4-(3-aminophenyl)-5-hexyl-3a-(1-phenylvinyl)-1,2,3,3a,6,6a-hexahydropentalen-1-ol (15g)

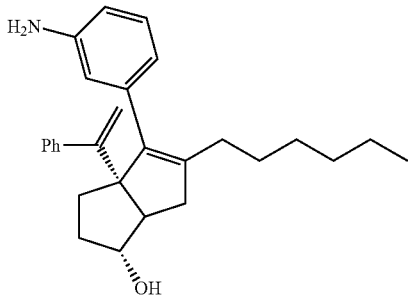 [SMILES: C=C(c1ccccc1)[C@@]12CC[C@@H](O)C1CC(CCCCCC)=C2c1cccc(N)c1]

The general procedure for amine coupling was followed, using (exo)-6-(3 bromophenyl)-5-hexyl-3-(methoxymethoxy)-6a-(1-phenylvinyl)-1,2,3,3a,4,6a-hexahydropentalen-1-ol as the brominated [3.3.0] bicycle. The crude oil was purified by silica gel chromatography in 20% EtOAc/Hex. $^1$H NMR (500 MHz, CDCl3) δ 7.49-7.20 (m, 5H), 7.09 (dd, J=9.6, 5.6 Hz, 1H), 6.61 (d, J=7.4 Hz, 2H), 6.55 (s, 1H), 5.06 (d, J=3.9 Hz, 1H), 5.02 (d, J=4.2 Hz, 1H), 3.93 (s, 1H), 3.52 (s, 2H), 2.32 (dt, J=13.6, 6.7 Hz, 1H), 2.25 (d, J=8.8 Hz, 1H), 2.04 (ddd, J=21.8, 11.9, 4.7 Hz, 5H), 1.77-1.62 (m, 3H), 1.38-1.06 (m, 8H), 0.86 (t, J=7.1 Hz, 3H). $^{13}$C NMR (126 MHz, CDCl3) δ 154.73, 145.58, 144.21, 140.96, 139.04, 138.54, 128.45, 127.79, 127.68, 126.61, 120.51, 116.40, 114.90, 113.57, 109.99, 82.13, 55.91, 40.20, 34.07, 32.02, 31.69, 29.78, 29.41, 27.82, 22.60, 14.08. LRMS (ESI, APCI) m/z: calc'd for C28H38NO [M+H]+ 403.3, found 402.9

(exo)-4-(5-amino-2-fluorophenyl)-5-hexyl-3a-(1-phenylvinyl)-1,2,3,3a,6,6a-hexahydropentalen-1-ol (16g)

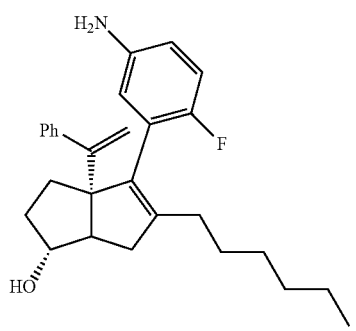 [SMILES: C=C(c1ccccc1)[C@@]12CC[C@@H](O)C1CC(CCCCCC)=C2c1cc(N)ccc1F]

The general procedure for amine coupling was followed, using (exo)-4-(5-amino-2-fluorophenyl)-5-hexyl-3a-(1-phenylvinyl)-1,2,3,3a,6,6a-hexahydropentalen-1-ol as the brominated [3.3.0] bicycle. The crude oil was purified by silica gel chromatography in 30-50% EtOAc/Hex.

$^1$H NMR (500 MHz, CDCl3) δ 7.38 (dd, J=6.7, 2.9 Hz, 2H), 7.32-7.25 (m, 2H), 6.99-6.79 (m, 2H), 6.56 (dt, J=8.6, 3.5 Hz, 1H), 6.50 (dd, J=6.0, 2.9 Hz, 1H), 5.09 (d, J=1.3 Hz, 1H), 4.93 (d, J=1.3 Hz, 1H), 3.96 (d, J=3.6 Hz, 1H), 3.79 (s, 1H), 3.53 (s, 1H), 3.46 (s, 2H), 2.56-2.44 (m, 1H), 2.28 (d, J=9.7 Hz, 1H), 2.10-2.02 (m, 2H), 1.96 (t, J=7.8 Hz, 2H), 1.88-1.78 (m, 1H), 1.75 (dd, J=12.0, 6.4 Hz, 1H), 1.67 (dd, J=12.9, 5.8 Hz, 1H), 1.35 (q, J=6.9 Hz, 1H), 1.32-1.15 (m, 6H), 0.86 (t, J=7.0 Hz, 3H). $^{13}$C NMR (126 MHz, CDCl3) δ 154.69, 144.58, 135.54, 129.55, 127.85, 127.61, 127.48, 126.70, 120.10, 119.69, 117.73, 115.55, 115.31, 114.90, 82.02, 69.59, 55.42, 40.54, 33.61, 33.04, 31.66, 31.14, 30.02, 29.41, 28.20, 27.26, 26.84, 25.35, 23.94, 23.51, 22.61, 14.09. 19F NMR (282 MHz, CDCl3) δ −126.95 LRMS (ESI, APCI) m/z: calc'd for C28H37FNO [M+H]+ 421.3, found 420.9 FTIR (neat): 3361, 3085, 2956, 2930, 2856, 1494, 1258, 1213, 775, 703, 668 cm-1.

(exo)-4-(5-amino-2-methylphenyl)-5-hexyl-3a-(1-phenylvinyl)-1,2,3,3a,6,6a-hexahydropentalen-1-ol (17g)

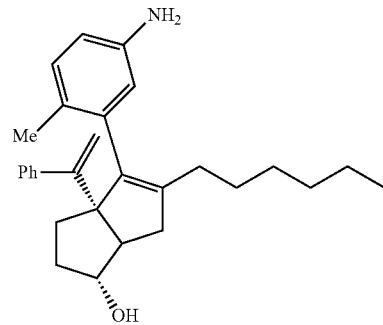 [SMILES: C=C(c1ccccc1)[C@@]12CC[C@@H](O)C1CC(CCCCCC)=C2c1cc(N)ccc1C]

The general procedure for amine coupling was followed, using (exo)-4-(5-bromo-2-methylphenyl)-5-hexyl-3a-(1-phenylvinyl)-1,2,3,3a,6,6a-hexahydropentalen-1-ol as the brominated [3.3.0] bicycle. The crude oil was purified by silica gel chromatography in 20-30% EtOAc/Hex.

$^1$H NMR (500 MHz, Chloroform-d) δ 7.44-7.38 (m, 2H), 7.33-7.27 (m, 2H), 7.02 (d, J=8.0 Hz, 1H), 6.85 (dd, J=8.9, 5.0 Hz, 1H), 6.54 (dd, J=8.0, 2.5 Hz, 1H), 6.47 (d, J=2.5 Hz, 1H), 5.18 (d, J=1.1 Hz, 1H), 4.89 (d, J=1.2 Hz, 1H), 3.98 (s, 1H), 3.79 (s, 2H), 3.53 (s, 3H), 2.61 (dd, J=17.2, 10.0 Hz, 1H), 2.30 (d, J=9.7 Hz, 1H), 2.06-1.99 (m, 2H), 1.97-1.79 (m, 2H), 1.77-1.68 (m, 2H), 1.38-1.07 (m, 11H), 0.86 (t, J=7.1 Hz, 3H).

(exo)-4-(3-amino-5-fluorophenyl)-5-hexyl-3a-(1-phenylvinyl)-1,2,3,3a,6,6a-hexahydropentalen-1-ol (18g)

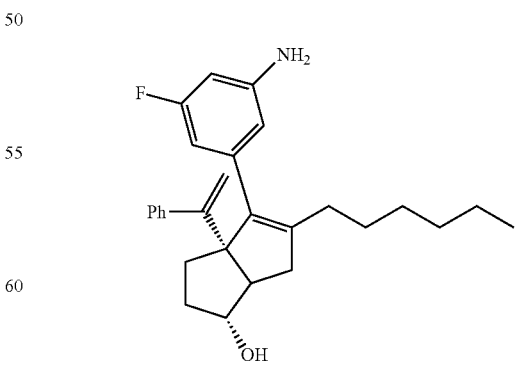

The general procedure for amine coupling was followed, using (exo)-4-(3-bromo-5-fluorophenyl)-5-hexyl-3a-(1-phenylvinyl)-1,2,3,3a,6,6a-hexahydropentalen-1-ol as the brominated [3.3.0] bicycle. The crude oil was purified by silica gel chromatography in 20-30% EtOAc/Hex.

¹H NMR (500 MHz, CDCl3) δ 7.36-7.30 (m, 2H), 7.31-7.20 (m, 3H), 6.41-6.21 (m, 3H), 5.08 (d, J=1.6 Hz, 1H), 5.05 (d, J=1.6 Hz, 1H), 3.92 (s, 1H), 3.79 (d, J=1.7 Hz, 1H), 3.70 (s, 2H), 3.53 (d, J=1.6 Hz, 1H), 2.32 (dd, J=16.7, 9.3 Hz, 1H), 2.25 (d, J=9.4 Hz, 1H), 2.13-1.97 (m, 4H), 1.79-1.63 (m, 3H), 1.42-1.12 (m, 6H), 0.87 (t, J=7.1, 6.5 Hz, 3H). ¹³C NMR (126 MHz, CDCl3) δ 164.21, 162.28, 154.51, 147.23, 147.14, 144.01, 141.78, 140.22, 140.14, 138.20, 127.73, 126.70, 119.67, 115.11, 112.05, 106.87, 106.70, 100.65, 100.46, 82.00, 69.24, 55.89, 40.20, 34.09, 31.98, 31.66, 31.14, 29.74, 29.40, 28.23, 27.74, 25.35, 23.91, 23.52, 22.60, 14.08. ¹⁹F NMR (282 MHz, CDCl3) δ -114.23. LRMS (ESI, APCI) m/z: calc'd for C28H37FNO [M+H]+ 422.3, found 421.8 FTIR (neat): 3360, 3210, 3085, 2956, 2929, 2858, 1692, 1610, 1585, 1459, 1425, 1258, 756, 703 cm-1.

Synthetic Scheme for Modifications to External Styrene

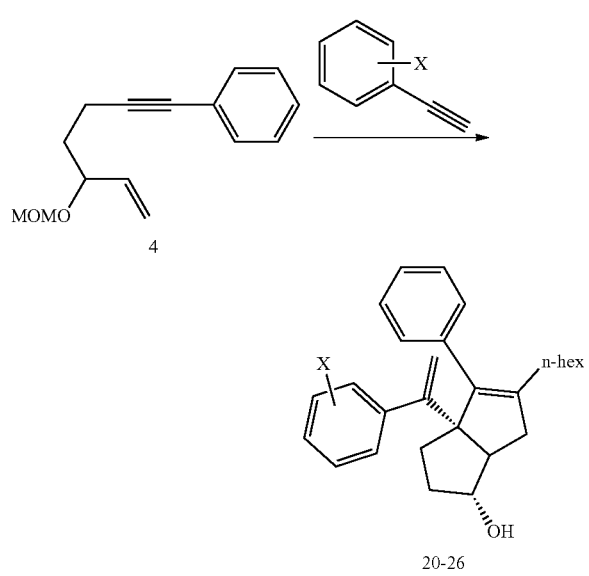

General Procedure for Zirconecene Mediated Cyclization and MOM Deprotection:

Bis(cyclopentadienyl)zirconium(IV) dichloride (zirconecene dichloride) (1.2 equiv.) was dried by azeotroping away latent water with benzene four times before being placed under nitrogen, dissolved in dry, degassed tetrahydrofuran (THF) and cooled to -78° C. in a dry ice/acetone bath. The resulting solution of zirconecene dichloride was treated with nBuLi (2.4 equiv.) to form a clear, light yellow solution and allowed to stir. After approximately 30 minutes, azeotroped (5-(methoxymethoxy)hept-6-en-1-yn-1-yl)benzene (1.0 equiv.) in dry, degassed THF was added portionwise to afford a pink-orange solution, and the reaction mixture was held at -78° C. for 30 minutes before allowing to warm to room temperature and stirred over 2.5 hours. The reaction mixture was then re-cooled to -78° C. and the required azeotroped dibromoheptane (1.1 equiv.) were added in dry, degassed THF. Freshly prepared lithium diisopropylamine (LDA, 1.0 M, 1.1 equiv.) was added at -78° C. and stirred for 15 minutes. The required, freshly prepared, lithium acetylide (3.6 equiv.) was added to the reaction mixture dropwise in dry, degassed THF. The resulting dark reddish brown solution was stirred at -78° C. for 1.5 hours. The reaction was then quenched with methanol and saturated aqueous sodium bicarbonate and allowed to warm to room temperature to form a light yellow slurry. The slurry was poured over water and extracted with ethyl acetate four times. The combined organic layers were washed with brine, dried with MgSO4, and concentrated in vacuo. The resulting colored oil (typically yellow, orange, or green), was roughly purified on a plug of silica and eluted with 20% EtOAc/Hexanes to afford an oil which is a mixture of quenched acetylide and desired bis-protected [3,3,0] bicyclic compounds (and in some cases protonolysis byproduct), which was carried on without further purification.

The crude mixture (1.0 equiv.) was dissolved in acetonitrile, and concentrated HCl (excess) was added and the resulting dark purple-blue reaction mixture was stirred for about 30 minutes (monitored by LCMS), concentrated, and subjected directly to silica gel chromatography in 5-20% EtOAc/Hex to afford the desired exo compound.

(exo)-3a-(1-(2-fluorophenyl)vinyl)-5-hexyl-4-phenyl-1,2,3,3a,6,6a-hexahydropentalen-1-ol (20)

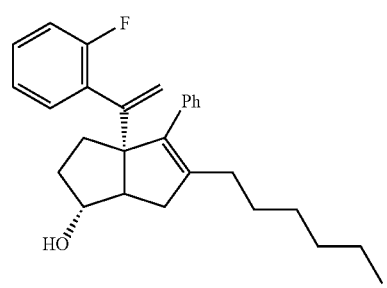 [SMILES: C=C(c1ccccc1F)[C@@]12CC[C@@H](O)C1CC(CCCCCC)=C2c1ccccc1]

The general procedure for zirconecene mediated cyclization and MOM deprotection was followed, using 1-ethynyl-2-fluorobenzene to form the required lithium acetylide. The resulting crude oil was purified in 5-20% EtOAc/Hex.

¹H NMR (500 MHz, CDCl3) δ 7.38-7.17 (m, 7H), 7.03 (dtt, J=13.0, 7.5, 1.1 Hz, 2H), 5.27 (s, 1H), 5.11 (s, 1H), 3.92 (d, J=4.3 Hz, 1H), 2.31 (d, J=14.3 Hz, 2H), 2.15-1.95 (m, 4H), 1.76-1.57 (m, 4H), 1.40-1.15 (m, 7H), 0.86 (td, J=7.1, 0.9 Hz, 3H). ¹³C NMR (126 MHz, CDCl3) δ 160.57, 158.63, 147.86, 141.76, 138.28, 137.40, 130.40, 129.67, 128.40, 128.34, 127.69, 126.59, 123.18, 116.72, 115.43, 115.24, 81.97, 69.38, 56.83, 39.67, 34.72, 31.65, 31.22, 29.77, 29.35, 27.91, 22.58, 14.08. ¹⁹F NMR (282 MHz, CDCl3) δ -113.74. LRMS (ESI, APCI) m/z: calc'd for C28H36FO [M+H]+ 407.3, found 406.9 FTIR (neat): 3354, 3090, 3075, 2954, 2927, 2855, 1489, 1446, 1217, 755, 701 cm-1.

(exo)-5-hexyl-4-phenyl-3a-(1-(o-tolyl)vinyl)-1,2,3,3a,6,6a-hexahydropentalen-1-ol (21)

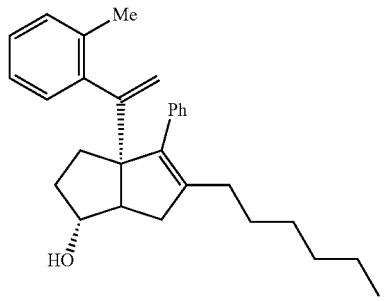 [SMILES: C=C(c1ccccc1C)[C@@]12CC[C@@H](O)C1CC(CCCCCC)=C2c1ccccc1]

The general procedure for zirconecene mediated cyclization and MOM deprotection was followed, using 1-ethynyl-2-methylbenzene to form the required lithium acetylide. The resulting crude oil was purified in 10% EtOAc/Hex.

$^1$H NMR (600 MHz, CDCl3) δ 7.36-7.30 (m, 2H), 7.30-7.26 (m, 1H), 7.24 (d, J=7.5 Hz, 2H), 7.18 (d, J=7.5 Hz, 1H), 7.14 (t, J=7.4 Hz, 1H), 7.04 (t, J=7.4 Hz, 1H), 5.08 (s, 1H), 4.95 (s, 1H), 3.91 (s, 1H), 2.26 (s, 3H), 2.25-2.12 (m, 2H), 2.06-1.88 (m, 4H), 1.76-1.66 (m, 2H), 1.61 (dd, J=11.9, 6.3 Hz, 1H), 1.42-1.28 (m, 3H), 1.28-1.22 (m, 1H), 1.22-1.15 (m, 4H), 0.85 (t, J=7.2 Hz, 3H). $^{13}$C NMR (126 MHz, CDCl3) δ 152.27, 142.91, 141.73, 138.48, 137.68, 135.64, 130.07, 129.97, 127.62, 126.62, 126.50, 124.76, 115.47, 82.05, 74.70, 69.98, 55.74, 39.82, 34.59, 31.83, 31.67, 29.65, 29.31, 27.91, 22.63, 20.74, 14.12. LRMS (ESI, APCI) m/z: calc'd for C29H39O [M+H]+ 403.3, found 403.0 FTIR (neat): 3340, 3095, 3080, 2954, 2926, 2855, 1489, 1456, 1440, 904, 765, 730, 710 cm-1.

(exo)-5-hexyl-3a-(1-(2-methoxyphenyl)vinyl)-4-phenyl-1,2,3,3a,6,6a-hexahydropentalen-1-ol (22)

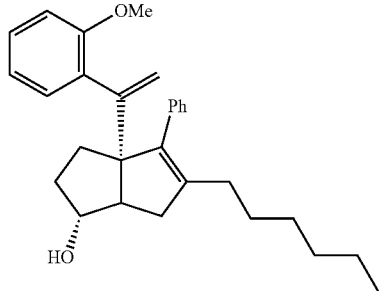

The general procedure for zirconecene mediated cyclization and MOM deprotection was followed, using 1-ethynyl-2-methoxybenzene to form the required lithium acetylide. The resulting crude oil was purified in 10-20% EtOAc/Hex.

$^1$H NMR (600 MHz, CDCl3) δ 7.36-7.18 (m, 6H), 6.95 (d, J=7.1 Hz, 1H), 6.88-6.81 (m, 2H), 5.18 (d, J=1.8 Hz, 1H), 5.01 (d, J=1.8 Hz, 1H), 3.86 (s, 1H), 3.75 (s, 3H), 2.50 (dd, J=16.6, 9.1 Hz, 1H), 2.45 (d, J=8.6 Hz, 1H), 2.08 (d, J=16.6 Hz, 1H), 2.01 (t, J=7.7 Hz, 2H), 1.81-1.72 (m, 2H), 1.65-1.58 (m, 2H), 1.58-1.53 (m, 1H), 1.36-1.29 (m, 2H), 1.27-1.20 (m, 2H), 1.21-1.14 (m, 2H), 0.84 (t, J=7.2 Hz, 3H). $^{13}$C NMR (151 MHz, CDCl3) δ 172.46, 169.63, 156.37, 151.45, 140.47, 137.69, 132.61, 130.06, 129.77, 127.97, 127.49, 126.39, 120.35, 115.58, 110.75, 81.67, 69.32, 57.60, 55.56, 51.31, 39.63, 34.60, 31.63, 31.08, 29.60, 29.21, 28.00, 22.58, 14.06. LRMS (ESI, APCI) m/z: calc'd for C29H39O2 [M+H]+ 417.3, found 417.9 FTIR (neat): 3355, 3085, 3075, 2950, 2928, 2855, 1738, 1490, 1462, 1240, 1030, 751, 701 cm-1.

(exo)-3a-(1-(4-bromophenyl)vinyl)-5-hexyl-4-phenyl-1,2,3,3a,6,6a-hexahydropentalen-1-ol (23a)

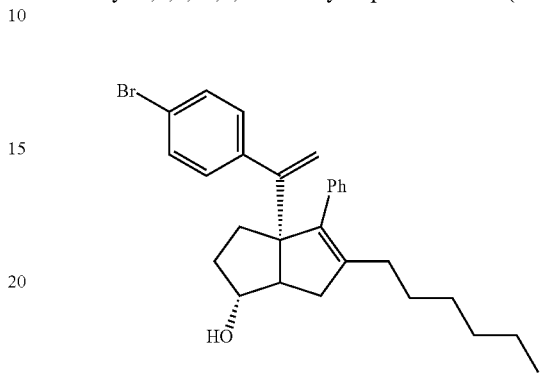

The general procedure for zirconecene mediated cyclization and MOM deprotection was followed, using 1-bromo-4-ethynylbenzene to form the required lithium acetylide. The resulting crude oil was purified in 10% EtOAc/Hex.

(exo)-5-hexyl-3a-(1-(4-hydroxyphenyl)vinyl)-4-phenyl-1,2,3,3a,6,6a-hexahydropentalen-1-ol (23b)

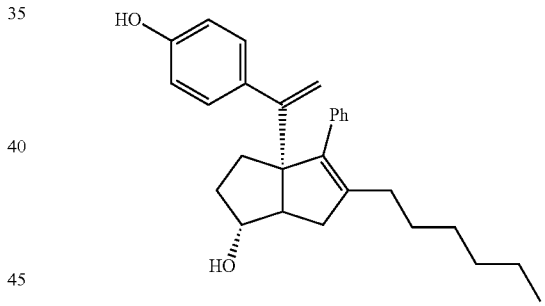

Potassium Hydroxide (3.0 equiv.), tris(dibenzylideneacetone) dipalladium(0) (0.01 equiv.), and tBuXPhos (0.04 equiv.) were suspended in 1,4-dioxane in a reaction tube under nitrogen. (exo)-3a-(1-(4-bromophenyl) vinyl)-5-hexyl-4-phenyl-1, 2, 3, 3a, 6, 6a-hexa hydropentalen-1-ol was added in dioxane. Water (~10 equiv.) was added. The reaction mixture was heated to 80° C. for 16 hours. After stirring, the mixture was poured over water and ethyl acetate, and the organic layer was washed with water and brine to remove 1,4-dioxane. The organic layer was dried with MgSO4, concentrated, and purified on silica in 20-50% EtOAc/Hex.

$^1$H NMR (500 MHz, CDCl3) δ 7.38-7.27 (m, 4H), 7.24-7.14 (m, 3H), 6.78-6.70 (m, 2H), 5.03 (d, J=1.4 Hz, 1H), 4.96 (d, J=1.5 Hz, 1H), 4.74 (s, 1H), 3.95 (s, 1H), 2.38 (dd, J=16.9, 9.4 Hz, 1H), 2.28 (d, J=9.3 Hz, 1H), 2.12-1.93 (m, 4H), 1.78-1.62 (m, 3H), 1.33 (dd, J=14.0, 6.7 Hz, 3H), 1.31-1.17 (m, 5H), 0.86 (t, J=7.1 Hz, 3H). $^{13}$C NMR (126 MHz, CDCl3) δ 154.56, 153.99, 141.13, 139.08, 137.37, 136.62, 129.67, 128.96, 127.61, 126.58, 114.52, 82.22, 69.46, 55.65, 40.27, 34.03, 32.03, 31.65, 29.70, 29.38, 27.83, 22.60, 14.09. LRMS (ESI, APCI) m/z: calc'd for C28H37O2 [M+H]+ 404.3, found 403.9 FTIR (neat): 3323, 3095, 3070, 3040, 2954, 2915, 2855, 1609, 1510, 1457, 1440, 1263, 1231, 837, 701 cm-1.

(exo)-5-hexyl-4-phenyl-3a-(3-phenylprop-1-en-2-yl)-1,2,3,3a,6,6a-hexahydropentalen-1-ol (24)

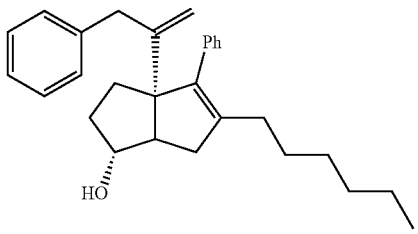 [SMILES: C=C(Cc1ccccc1)[C@@]12CC[C@@H](O)C1CC(CCCCCC)=C2c1ccccc1]

The general procedure for zirconecene mediated cyclization and MOM deprotection was followed, using prop-2-yn-1-yl benzene to form the required lithium acetylide. The resulting crude oil was purified in 5-20% EtOAc/Hex. $^1$H NMR (500 MHz, CDCl3) δ 7.34-7.27 (m, 4H), 7.25-7.17 (m, 4H), 7.11-7.07 (m, 2H), 4.93 (d, J=1.1 Hz, 1H), 4.50 (d, J=1.4 Hz, 1H), 3.99 (s, 1H), 3.50 (d, J=16.4 Hz, 1H), 3.39 (d, J=16.4 Hz, 1H), 2.89 (dd, J=17.2, 9.3 Hz, 1H), 2.39 (d, 1H), 2.25 (dd, J=17.3, 2.0 Hz, 1H), 2.17-2.03 (m, 3H), 1.80-1.70 (m, 1H), 1.56-1.51 (m, 1H), 1.42-1.35 (m, 2H), 1.28-1.12 (m, 7H), 0.84 (t, J=7.1 Hz, 3H). $^{13}$C NMR (126 MHz, CDCl3) δ 153.23, 140.85, 140.11, 139.13, 137.34, 129.65, 129.34, 128.28, 127.66, 126.53, 125.96, 95.51, 82.47, 70.23, 55.58, 40.66, 39.43, 34.18, 31.60, 30.21, 29.50, 29.18, 28.09, 22.61, 14.06. LRMS (ESI, APCI) m/z: calc'd for C29H39O [M+H]+ 403.3, found 403.0 FTIR (neat): 3362, 3070, 3035, 2960, 2926, 2856, 1701, 1599, 1495, 1453, 1032, 908, 753, 732, 705 cm-1.

(exo)-5-hexyl-1-hydroxy-4-phenyl-2,3,6,6a-tetrahydropentalen-3a(1H)-yl)(phenyl)methanone (25)

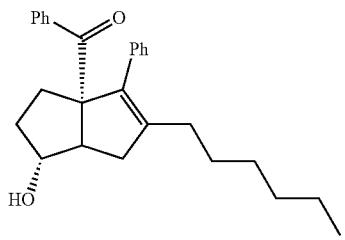 [SMILES: CCCCCCC1=C(c2ccccc2)[C@]2(C(=O)c3ccccc3)CC[C@@H](O)C2C1]

RJW100 (1.0 equiv.) was dissolved in DCM and cooled to −78° C. Ozone (excess) was bubbled through the solution until the reaction mixture was blue. At this point, the stream of ozone was stopped and the reaction was stirred until the blue color dissipated. Dimethylsulfide (DMS) was added, and the reaction was briefly stirred. The reaction solution was then concentrated in vacuo and the crude reaction mixture was purified on silica in 0-20% EtOAc/Hex to afford a clear, colorless oil (14 mg, 63%).

$^1$H NMR (600 MHz, CDCl3) δ 7.86 (d, J=7.7 Hz, 2H), 7.46 (t, J=7.4 Hz, 1H), 7.35 (dd, J=8.7, 6.7 Hz, 2H), 7.18 (d, J=6.6 Hz, 3H), 6.87 (dd, J=7.2, 2.3 Hz, 2H), 4.06 (s, 1H), 3.02 (dd, J=17.5, 10.2 Hz, 1H), 2.90 (d, J=11.2 Hz, 1H), 2.76-2.64 (m, 1H), 2.33 (dd, J=17.7, 3.5 Hz, 1H), 2.09 (t, J=7.8 Hz, 2H), 2.00 (d, J=12.2 Hz, 1H), 1.85-1.66 (m, 2H), 1.49-1.36 (m, 2H), 1.29-1.15 (m, 6H), 0.85 (dd, J=14.0, 7.2 Hz, 3H). $^{13}$C NMR (101 MHz, CDCl3) δ 203.40, 141.99, 139.95, 138.62, 136.24, 131.77, 129.03, 128.56, 128.13, 128.08, 126.99, 80.80, 76.25, 54.62, 40.48, 32.65, 31.62, 30.50, 29.42, 29.28, 27.80, 22.58, 21.59, 14.07. LRMS (ESI, APCI) m/z: calc'd for C27H35O2 [M+H]+ 389.6, found 389.2 FTIR (neat): 3405, 3080, 2955, 2927, 2857, 1698, 1680, 1597, 1446, 1254, 1180, 766, 699 cm-1.

(exo)-3a-benzyl-5-hexyl-4-phenyl-1,2,3,3a,6,6a-hexahydropentalen-1-ol (26)

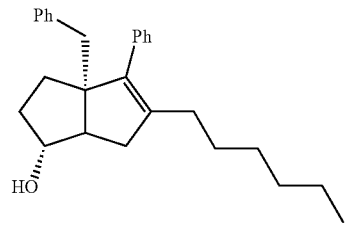 [SMILES: CCCCCCC1=C(c2ccccc2)[C@]2(Cc3ccccc3)CC[C@@H](O)C2C1]

A solution of 25 in ethylene glycol was prepared at room temperature. Hydrazine hydrate (9.5 equiv.) was added to the reaction mixture before heating to 100° C. for 1 h. Potassium hydroxide (10.0 equiv.) was subsequently added and the reaction mixture was stirred at 150° C. for ~48 h. After stirring, the solution was cooled to room temperature, partitioned between water and EtOAc, and extracted with EtOAc 3×. The combined organic layers were dried with MgSO4, filtered, and concentrated in vacuo. The crude reaction mixture was purified on silica in 10-20% EtOAc/Hex (2.6 mg, 22%).

$^1$H NMR (600 MHz, CDCl3) δ 7.37-7.33 (m, 3H), 7.30-7.27 (m, 1H), 7.24-7.22 (m, 1H), 7.21-7.17 (m, 3H), 7.16-7.11 (m, 2H), 3.83 (s, 1H), 2.93 (d, J=13.6 Hz, 1H), 2.73 (d, J=13.6 Hz, 1H), 2.38 (dd, J=15.6, 8.4 Hz, 1H), 2.34 (d, J=10.6 Hz, 1H), 2.05-1.99 (m, 1H), 1.89-1.83 (m, 2H), 1.74-1.67 (m, 3H), 1.49-1.44 (m, 1H), 1.29-1.18 (m, 5H), 1.12 (dt, J=6.0, 4.2 Hz, 3H), 0.82 (td, J=7.2, 0.6 Hz, 3H). $^{13}$C NMR (101 MHz, CDCl3) δ 140.91, 139.79, 139.35, 138.03, 130.45, 129.88, 127.91, 126.51, 126.03, 81.83, 64.26, 52.58, 43.98, 38.94, 33.84, 32.06, 31.59, 29.22, 29.02, 27.81, 22.56, 14.06. LRMS (ESI, APCI) m/z: calc'd for C26H35 [M−H2O]+358.3, found 358.3 FTIR (neat): 3440, 3070, 3020, 2965, 2930, 2855, 1498, 1456, 1263, 1185, 1029, 759, 703 cm-1.

Synthetic Scheme for Modifications to the Secondary Alcohol

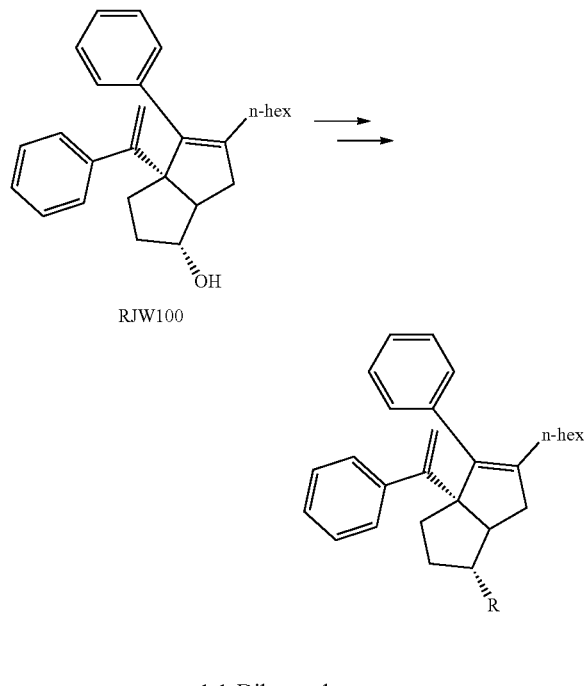

RJW100

1,1-Dibromoheptane

Triphenylphosphite (1.1 equiv) was suspended in DCM and cooled to −78° C. Bromine (1.1 equiv) was added dropwise and stirred briefly. Heptanal (1.0 equiv.) was then added in DCM and the reaction was allowed to come to room temperature over 3 hours. The reaction mixture was then filtered through silica and concentrated in vacuo. The crude oil was purified by silica gel chromatography in 100% hexanes to afford a clear, colorless oil (67%).

RJW100 Synthesis

General Procedure for Zirconecene Mediated Cyclization and TBS Deprotection

Bis(cyclopentadienyl)zirconium(IV) dichloride (zirconecene dichloride) (1.2 equiv.) was dried by azeotroping away latent water with benzene four times before being placed under nitrogen, dissolved in tetrahydrofuran (THF) and cooled to −78° C. in a dry ice/acetone bath. The resulting solution of zirconecene dichloride was treated with nBuLi (2.4 equiv.) to form a clear, light yellow solution and allowed to stir. After approximately 30 minutes, azeotroped tert-butyldimethyl((7-phenylhept-1-en-6-yn-3-yl)oxy)silane (19) (1.0 equiv.) in dry THF was added portionwise to afford a pink-orange solution, and the reaction mixture was held at −78° C. for 30 minutes before allowing to warm and stir at room temperature for 2.5 hours. The reaction mixture was then re-cooled to −78° C. and the required azeotroped dibromoheptane (1.1 equiv.) was added in dry THF. Freshly prepared lithium diisopropylamide (LDA, 1.0 M, 1.1 equiv.) was added at −78° C. and stirred for 15 minutes. Lithium phenylacetylide (3.6 equiv.) was then prepared and added to the reaction mixture dropwise in dry THF. The resulting dark reddish brown solution was stirred at −78° C. for 1.5 hours. The reaction was then quenched with methanol and saturated aqueous sodium bicarbonate and allowed to warm to room temperature to form a light yellow slurry. The resulting slurry was poured over water and extracted with ethyl acetate four times. The combined organic layers were washed with brine, dried with MgSO4, and concentrated in vacuo. The resulting yellow oil was roughly purified on a plug of silica and eluted with 20% EtOAc/Hexanes to afford a yellow oil which is a mixture of phenylacetylene and desired bis-protected [3.3.0] bicyclic compounds, which was carried on without further purification. This procedure affords exo and endo diastereomers in a 1.6:1 ratio as determined by characteristic 1H NMR signals.

The crude mixture (1.0 equiv.) was dissolved in THF, and tetrabutylammonium fluoride (1.5 equiv.) was added and the resulting dark brown solution was stirred open to air for 18 hours, concentrated, and subjected directly to silica gel chromatography in 5-10% EtOAc/Hexanes to separate both endo and exo diastereomers (with endo eluting before exo) of the desired compounds as clear, colorless oils.

5-hexyl-4-phenyl-3a-(1-phenylvinyl)-3,3a,6,6a-tetrahydropentalen-1(2H)-one (27)

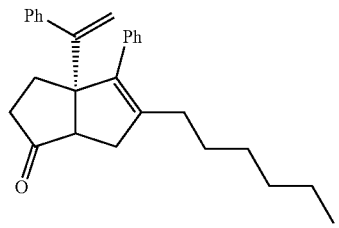 [SMILES: C=C(c1ccccc1)[C@@]12CCC(=O)C1CC(CCCCCC)=C2c1ccccc1]

A solution of alcohol (isomer irrelevant, 1.0 equiv.) in acetonitrile was treated with N-methylmorpholine oxide (1.5 equiv.) and allowed to stir to homogeneity before the addition of tetrapropylammonium perruthenate (0.1 equiv.) The solution was stirred at room temperature until completion as determined by TLC (~10 min). The solution was concentrated in vacuo and subjected directly to silica gel chromatography in 10% EtOAc/Hex to afford the title compound as a clear, colorless oil (88% yield).

$^1$H NMR (400 MHz, CDCl3) δ 7.38-7.25 (m, 6H), 7.24-7.19 (m, 4H), 5.20 (d, J=1.4 Hz, 1H), 5.09 (d, J=1.4 Hz, 1H), 2.44 (d, J=7.5 Hz, 1H), 2.34-2.23 (m, 2H), 2.15-1.95 (m, 5H), 1.89 (ddt, J=16.5, 7.8, 1.1 Hz, 1H), 1.29-1.09 (m, 8H), 0.82 (t, J=7.0 Hz, 3H). $^{13}$C NMR (101 MHz, CDCl3) δ 222.79, 153.19, 144.91, 142.47, 137.29, 136.63, 128.95, 128.24, 128.09, 127.59, 127.03, 126.96, 115.26, 109.99, 65.39, 55.50, 38.76, 37.50, 31.54, 29.97, 29.37, 28.33, 27.60, 22.52, 14.05. LRMS (ESI, APCI) m/z: calc'd for C28H35O [M+H]+ 385.3, found 385.3 FTIR (neat): 3080, 3053, 2955, 2926, 2855, 1743, 1598, 1574, 1491, 1458, 1441, 906, 765, 701 cm-1.

(endo or exo)-5-hexyl-4-phenyl-3a-(1-phenylvinyl)-1,2,3,3a,6,6a-hexahydropentalen-1-yl sulfamate (28 endo, 28 exo)

(endo or exo)-5-hexyl-4-phenyl-3a-(1-phenylvinyl)-1,2,3,3a,6,6a-hexahydropentalen-1-yl carbamate (29 endo, 29 exo)

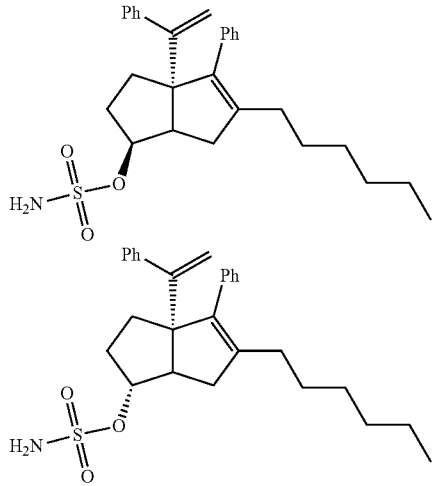

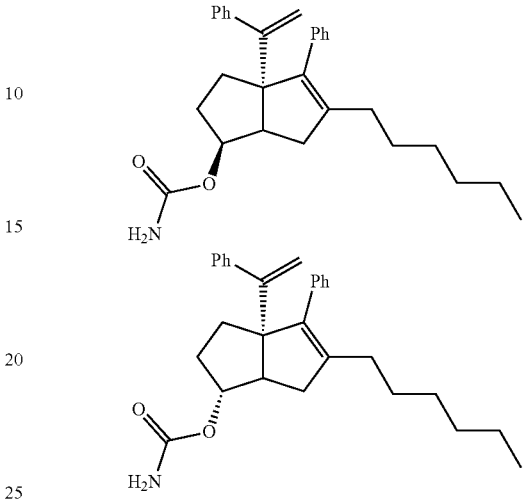

A 1M solution of sulfamoyl chloride (1.2 equiv.) in DMA was cooled to 0° C. A solution of the appropriate alcohol isomer (1.0 equiv.) in DMA was added slowly, followed by triethylamine (excess); the resulting solution was stirred for one hour. The solution was then diluted with water and extracted with EtOAc. The combined organic layers were then washed with water and brine to remove DMA, dried with Na2SO4, filtered, and concentrated in vacuo. The oil was purified by silica gel chromatography in 20% EtOAc/Hex with 0.5% triethylamine, to afford the title compound as a clear oil (endo, 78% yield).

Endo $^1$H NMR (500 MHz, CDCl3) δ 7.35-7.24 (m, 8H), 7.23-7.15 (m, 2H), 5.11 (s, 1H), 4.92 (s, 1H), 4.87 (td, J=9.1, 5.2 Hz, 1H), 4.64 (s, 2H), 2.71 (d, J=9.0 Hz, 1H), 2.60 (d, J=17.5 Hz, 1H), 2.17 (dd, J=17.7, 9.3 Hz, 1H), 2.10-2.01 (m, 3H), 1.92-1.83 (m, 1H), 1.83-1.76 (m, 1H), 1.68 (td, J=12.6, 5.6 Hz, 1H), 1.45-1.35 (m, 2H), 1.32-1.16 (m, 6H), 0.86 (t, J=7.1 Hz, 3H). Endo $^{13}$C NMR (126 MHz, CDCl3) δ 153.83, 143.49, 143.24, 138.53, 136.48, 129.82, 127.88, 127.68, 127.62, 126.96, 126.78, 115.69, 84.11, 68.22, 47.13, 34.89, 31.63, 31.15, 30.54, 29.76, 29.40, 27.73, 22.59, 14.07. Endo LRMS (ESI, APCI) m/z: calc'd for C28H36NO3S [M−H]− 465.3, found 465.4 Endo FTIR (neat): 3360, 3284, 3080, 3055, 3020, 2955, 2928, 2855, 1558, 1491, 1441, 1356, 1184, 1029, 1004, 913, 851, 775, 703, 668 cm-1.

Exo $^1$H NMR (500 MHz, CDCl3) δ 7.36-7.28 (m, 7H), 7.29-7.16 (m, 3H), 5.10 (d, J=1.3 Hz, 1H), 5.00 (d, J=1.3 Hz, 1H), 4.75 (d, J=4.4 Hz, 1H), 4.62 (s, 2H), 2.68 (d, J=9.1 Hz, 1H), 2.40 (dd, J=18.1, 9.4 Hz, 1H), 2.19-2.01 (m, 6H), 1.88-1.73 (m, 2H), 1.38-1.16 (m, 7H), 0.87 (t, J=7.1 Hz, 3H). Exo $^{13}$C NMR (126 MHz, cdcl3) δ 153.55, 143.65, 141.37, 138.84, 136.83, 129.56, 127.83, 127.77, 127.71, 126.89, 126.86, 115.59, 93.70, 69.27, 52.76, 40.13, 32.14, 32.00, 31.60, 29.65, 29.36, 27.77, 22.56, 14.06. Exo LRMS (ESI, APCI) m/z: calc'd for C28H36NO3S [M−H]− 465.3, found 465.2 Exo FTIR (neat): 3377, 3284, 3080, 3053, 3019, 2955, 2926, 2854, 1598, 1572, 1558, 1491, 1457, 1440, 1356, 1182, 1073, 1028, 924, 904, 813, 773, 764, 701, 667 cm-1.

The required alcohol isomer (1.0 equiv.) was suspended in MeCN and cooled to −15° C. Chlorosulfonyl isocyanate (2.0 equiv.) was added and the reaction was stirred for 2 hours. After completion via TLC, concentrated hydrochloric acid (0.5) was added slowly and stirred to room temperature over 4 hours. The solution was quenched with NaHCO3, diluted with water, and extracted with EtOAc. The organic layers were rinsed with brine, dried with Na2SO4, filtered, and concentrated in vacuo. The resulting oil was purified by silica gel chromatography in 5-30% EtOAc/Hex to afford the title compounds as yellow oils (79%).

Endo $^1$H NMR (400 MHz, CDCl3) δ 7.34-7.23 (m, 5H), 7.24-7.18 (m, 5H), 5.04 (d, J=1.4 Hz, 1H), 4.93 (d, J=1.4 Hz, 1H), 4.91-4.87 (m, OH), 4.54 (s, 2H), 2.66 (td, J=8.9, 1.8 Hz, 1H), 2.32 (dd, J=17.7, 1.9 Hz, 1H), 2.10-1.95 (m, 3H), 1.93-1.83 (m, 1H), 1.73-1.59 (m, 2H), 1.36 (p, J=7.3 Hz, 2H), 1.29-1.16 (m, 7H), 0.84 (t, J=7.0 Hz, 3H). Endo $^{13}$C NMR (101 MHz, CDCl3) δ 156.40, 154.31, 143.67, 143.27, 138.53, 136.90, 129.71, 127.77, 127.69, 127.63, 126.73, 126.59, 115.16, 68.54, 46.99, 34.45, 31.70, 31.07, 30.10, 29.79, 29.39, 27.81, 22.61, 14.10. Endo LRMS (ESI, APCI) m/z: calc'd for C29H39NO3 [M+H2O]− 449.3, 449.1 Endo FTIR (neat): 3490, 3343, 3085, 3050, 3015, 2955, 2926, 2855, 1716, 1598, 1491, 1440, 1392, 1335, 1041, 903, 765, 701 cm-1.

Exo $^1$H NMR (500 MHz, CDCl3) δ 7.41-7.19 (m, 10H), 5.08 (d, J=1.6 Hz, 1H), 5.02 (d, J=1.6 Hz, 1H), 4.77 (dt, J=4.2, 1.4 Hz, 1H), 4.56 (s, 2H), 2.42 (d, J=8.1 Hz, 1H), 2.36 (dd, J=16.3, 8.9 Hz, 1H), 2.19 (d, J=17.0 Hz, 1H), 2.14-1.88 (m, 4H), 1.85-1.63 (m, 3H), 1.41-1.29 (m, 2H), 1.31-1.16 (m, 5H), 0.88 (t, J=7.0 Hz, 3H). Exo $^{13}$C NMR (126 MHz, CDCl3) δ 156.59, 154.47, 143.89, 141.92, 138.53, 137.30, 129.61, 127.76, 127.71, 126.75, 126.67, 115.02, 85.61, 69.36, 53.01, 40.34, 32.36, 31.66, 31.54, 29.74, 29.40, 27.81, 22.60, 14.11. Exo LRMS (ESI, APCI) m/z: calc'd for C29H39NO3 [M+H2O]− 449.3, 449.3 Exo FTIR (neat): 3350, 3194, 3055, 2956, 2927, 2855, 1712, 1597, 1544, 1492, 1443, 1408, 1336, 1077, 819, 759, 702 cm-1.

(endo or exo) 5-hexyl-4-phenyl-3a-(1-phenylvinyl)-1,2,3,3a,6,6a-hexahydropentalen-1-yl methanesulfonate(30 endo, 30 exo)

(endo or exo)-5-hexyl-4-phenyl-3a-(1-phenylvinyl)-1,2,3,3a,6,6a-hexahydropentalen-1-azide (31 endo, 31 exo)

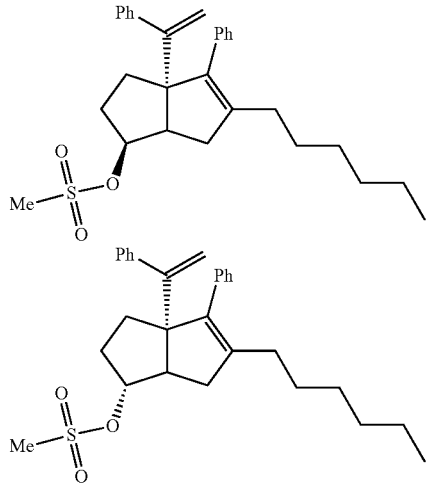

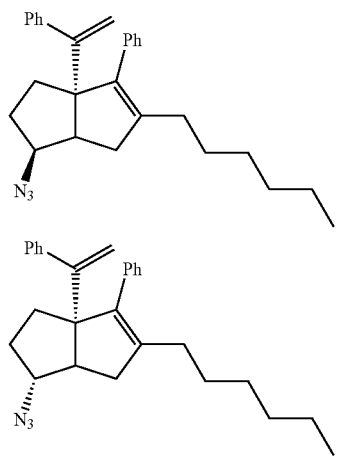

In a 20 dram vial equipped with a stir bar was dissolved the desired isomer of RJW100 (1.0 equiv.). Triethylamine (5.0 equiv.) was added, followed by methanesulfonyl chloride (5.0 equiv.) The reaction mixture was allowed to stir at room temperature for 1 h before concentrating in vacuo and purifying by silica gel chromatography in 30% EtOAc/hexanes. (Endo: 62.1 mg, 95%; Exo: 150.3 mg, 95%)

Endo $^1$H NMR (500 MHz, CDCl3) δ 7.36-7.26 (m, 8H), 7.24-7.17 (m, 2H), 5.13 (d, J=1.1 Hz, 1H), 5.04-4.92 (m, 1H), 4.95 (d, J=1.2 Hz, 1H), 3.00 (s, 3H), 2.70 (t, J=9.0, 1.8 Hz, 1H), 2.60 (d, J=17.4 Hz, 1H), 2.17 (dd, J=17.5, 9.1 Hz, 1H), 2.08 (ttd, J=13.5, 6.8, 4.9 Hz, 4H), 1.92-1.76 (m, 3H), 1.72 (td, J=12.5, 5.8 Hz, 1H), 1.40 (p, 2H), 1.33-1.18 (m, 4H), 0.88 (t, J=7.2 Hz, 3H). Endo $^{13}$C NMR (126 MHz, CDCl3) δ 153.71, 143.41, 143.19, 138.52, 136.45, 129.78, 127.89, 127.72, 127.64, 126.99, 126.81, 115.69, 82.85, 68.23, 47.40, 38.23, 34.86, 31.65, 31.11, 30.97, 29.76, 29.41, 27.76, 22.60, 14.09. Endo LRMS (ESI, APCI) m/z: calc'd for C29H38O3S [M] 466.3, found [M−CH3O3S] 368.9 Endo FTIR (neat): 3070, 3028, 2955, 2931, 2857, 1570, 1492, 1445, 1356, 1180, 938, 908, 857, 764, 702 cm-1.

Exo $^1$H NMR (500 MHz, CDCl3) δ 7.37-7.25 (m, 8H), 7.27-7.19 (m, 2H), 5.11 (d, J=1.3 Hz, 1H), 5.01 (d, J=1.3 Hz, 1H), 4.83 (d, J=4.0 Hz, 1H), 2.95 (s, 3H), 2.63 (d, J=9.2 Hz, 1H), 2.41 (dd, J=17.4, 9.5 Hz, 1H), 2.14 (dd, J=17.5, 2.0 Hz, 1H), 2.11-1.98 (m, 4H), 1.90-1.75 (m, 2H), 1.40-1.31 (m, 2H), 1.32-1.17 (m, 6H), 0.87 (t, J=7.1 Hz, 3H). Exo $^{13}$C NMR (151 MHz, CDCl3) δ 153.50, 143.57, 141.32, 138.78, 136.75, 132.75, 129.55, 127.83, 127.76, 127.64, 126.90, 126.86, 115.62, 92.12, 69.21, 53.04, 39.96, 38.73, 32.36, 32.11, 31.58, 29.62, 29.35, 27.75, 22.55, 14.05. Exo LRMS (ESI, APCI) m/z: calc'd for C29H38O3S [M] 466.3, found [M−CH3O3S] 368.9 Exo FTIR (neat): 3060, 3028, 2960, 2929, 2855, 1560, 1544, 1498, 1441, 1354, 1173, 930, 901, 702 cm-1.

In a reaction tube equipped with a stir bar was added the required mesylated isomer (30 endo or exo, 1.0 equiv.) in DMF. Sodium azide (10.0 equiv.) was added and the reaction mixture was allowed to stir for about 16 h at 80° C. After stirring, the solution was allowed to cool to room temperature and poured over water and EtOAc. The organic layer was washed with water and brine in order to remove DMF, dried over MgSO4, and concentrated in vacuo. The reaction mixture was purified on silica in 0-10% EtOAc/hex. (Endo: 117.2 mg, 88%; Exo: 45.6 mg, 90%) (Note: inversion of stereochemistry).

Endo $^1$H NMR (600 MHz, CDCl3) δ 7.36-7.26 (m, 8H), 7.23-7.18 (m, 2H), 5.10 (d, J=1.3 Hz, 1H), 4.94 (d, J=1.3 Hz, 1H), 3.87 (ddd, J=10.5, 8.8, 5.9 Hz, 1H), 2.62-2.51 (m, 2H), 2.16-2.01 (m, 4H), 1.97-1.88 (m, 1H), 1.79 (ddd, J=12.4, 5.9, 1.8 Hz, 1H), 1.71 (td, J=12.4, 5.2 Hz, 1H), 1.67-1.59 (m, 1H), 1.40 (p, J=7.5 Hz, 2H), 1.31-1.19 (m, 5H), 0.87 (t, J=7.2 Hz, 3H). Endo $^{13}$C NMR (126 MHz, CDCl3) δ 154.20, 143.75, 143.36, 138.51, 136.77, 129.82, 127.84, 127.65, 126.89, 126.70, 115.50, 69.05, 64.86, 47.89, 35.65, 32.51, 31.68, 30.15, 29.80, 29.45, 27.77, 22.62, 14.12. Endo LRMS [ESI] calc'd for C28H34N3 412.3 [M+H]+, found 411.8 Endo FTIR (neat): 3085, 3053, 2955, 2929, 2855, 2098 (s), 1491, 1441, 1340, 1259, 905, 775, 763, 701 cm-1.

Exo $^1$H NMR (500 MHz, CDCl3) δ 7.36-7.24 (m, 8H), 7.21 (dt, J=7.5, 1.4 Hz, 2H), 5.09 (s, 1H), 5.00 (s, 1H), 3.64 (s, 1H), 2.44-2.35 (m, 2H), 2.14-1.93 (m, 5H), 1.83-1.67 (m, 3H), 1.40-1.30 (m, 2H), 1.32-1.17 (m, 5H), 0.86 (d, J=7.1 Hz, 3H). Exo $^{13}$C NMR (126 MHz, CDCl3) δ 153.83, 143.76, 141.32, 139.07, 137.03, 129.64, 127.78, 127.77, 127.72, 126.80, 126.75, 115.29, 71.33, 69.34, 52.09, 41.13, 32.64, 31.63, 31.20, 29.69, 29.38, 27.80, 22.58, 14.07. Exo LRMS (ESI) m/z: calc'd for C28H34N3 [M+H]+ 412.3, found 412.3 Exo FTIR (neat): 3080, 3053, 3019, 2955, 2926, 2855, 2097 (s), 1491, 1441, 1341, 1247, 904, 774, 701 cm-1.

(endo or exo)-5-hexyl-4-phenyl-3a-(1-phenylvinyl)-1,2,3,3a,6,6a-hexahydropentalene-1-carbonitrile (32 endo, 32 exo)

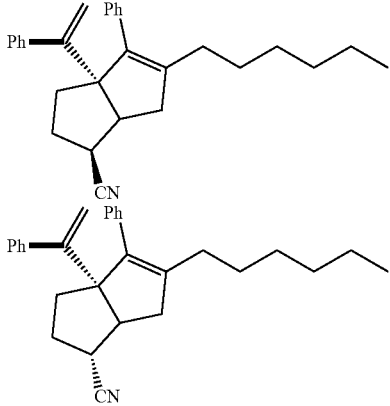

(endo or exo)-5-hexyl-4-phenyl-3a-(1-phenylvinyl)-1, 2, 3,3a, 6, 6a-hexahydropentalen-1-amine (33 endo, 33 exo)

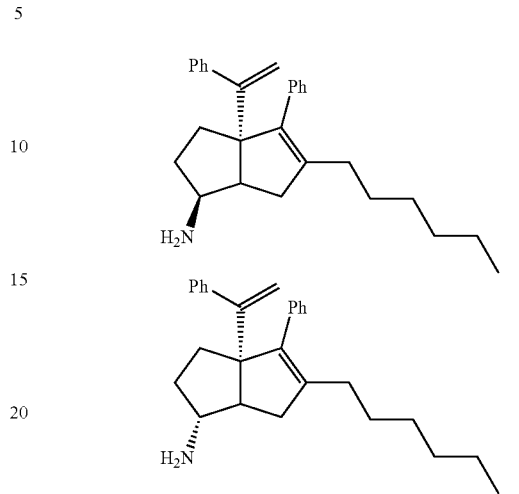

Sodium cyanide (10.0 equiv.) was suspended in DMF, followed by addition of the required mesylated isomer (30 endo or 30 exo) (1.0 equiv.) in DMF. The mixture was allowed to stir at 100° C. for about 40 hours. The reaction was diluted with water and extracted with EtOAc. The combined organic layers were washed with water and brine to remove DMF, dried with Na2SO4, filtered, and concentrated to dryness. The crude oil was purified by silica gel chromatography in 5% EtOAc/Hex to yield the title compound. (Endo: 21.9 mg, 26%; Exo: 19.9 mg, 47%) (Note: An appreciable amount of E2 elimination product is typically also observed, despite considerable optimization of reaction conditions. Also note the inversion of stereochemistry).

Endo $^1$H NMR (600 MHz, CDCl3) δ 7.34-7.23 (m, 8H), 7.22-7.19 (m, 2H), 5.08 (s, 1H), 4.98 (s, 1H), 2.91-2.84 (m, 1H), 2.60 (t, J=9.0 Hz, 1H), 2.53 (d, J=17.5 Hz, 1H), 2.30 (dd, J=17.6, 8.6 Hz, 1H), 2.15-1.97 (m, 3H), 1.83-1.75 (m, 2H), 1.74-1.66 (m, 1H), 1.39 (p, J=7.6 Hz, 2H), 1.31-1.17 (m, 6H), 0.84 (d, J=7.0 Hz, 3H). Endo $^{13}$C NMR (126 MHz, CDCl3) δ 153.37, 143.23, 143.22, 137.89, 136.55, 129.57, 127.88, 127.83, 127.73, 127.05, 126.90, 121.12, 115.80, 69.77, 46.49, 39.10, 34.87, 34.69, 31.59, 30.57, 29.75, 29.46, 27.68, 22.59, 14.07. Endo LRMS (ESI, APCI) m/z: calc'd for C29H35N [M+H]+ 396.6 found 396.4 Endo FTIR (neat): 3075, 3053, 3025, 2950, 2926, 2854, 2237, 1598, 1573, 1491, 1442, 1378, 1074, 1029, 907, 765, 702 cm-1.

Exo $^1$H NMR (600 MHz, CDCl3) δ 7.38-7.20 (m, 10H), 5.09 (s, 1H), 5.08 (s, 1H), 2.71 (dd, J=7.9, 4.9 Hz, 1H), 2.53 (q, J=11.0, 5.9 Hz, 1H), 2.29 (dd, J=17.9, 8.4 Hz, 1H), 2.12-1.98 (m, 4H), 1.92-1.86 (m, 2H), 1.72 (dt, J=13.1, 5.2 Hz, 1H), 1.36-1.15 (m, 8H), 0.84 (t, J=7.0 Hz, 3H). Exo $^{13}$C NMR (75 MHz, CDCl3) δ 153.05, 142.91, 141.48, 138.61, 136.60, 129.40, 128.01, 127.92, 127.82, 126.99, 126.95, 123.09, 115.43, 69.57, 51.76, 41.68, 37.48, 33.78, 31.60, 30.52, 29.74, 29.41, 27.79, 22.57, 14.08. Exo LRMS (ESI, APCI) m/z: calc'd for C29H36N [M+H]+ 398.3, found 398.3 Exo FTIR (neat): 3080, 3051, 3020, 2950, 2926, 2854, 2236, 1598, 1573, 1491, 1441, 1378, 1074, 1029, 905, 768, 700 cm-1.

The required azide isomer (31 endo or 31 exo) (1.0 equiv.) was dissolved in anhydrous Et2O under nitrogen then LiAlH4 (4.0M in Et2O, 10.0 equiv.) was added dropwise and stirred at room temperature for ~1 hr, until the reaction was complete by TLC. The reaction was quenched by cooling to 0° C. and diluting with Et2O before slow addition of 1 mL per gram of LiAlH4 water then 4 M NaOH. before pouring over EtOAc. The organic layer was washed with Rochelle's salt and brine to remove DMF and lithium salts, dried over MgSO4, and concentrated in vacuo. The resulting oil was then purified by silica gel chromatography in 50% EtOAc/Hex with 1% triethylamine to afford a colorless oil. (endo: 47.9 mg, 95%, exo: 40.0 mg, 92%).

Endo $^1$H NMR (600 MHz, CDCl3) δ 7.37-7.19 (m, 10H), 5.08 (d, J=1.4 Hz, 1H), 4.94 (d, J=1.5 Hz, 1H), 3.30 (ddd, J=11.0, 8.8, 5.7 Hz, 1H), 2.48 (d, J=17.4 Hz, 1H), 2.42 (t, J=9.0 Hz, 1H), 2.12-2.00 (m, 2H), 1.83-1.78 (m, 1H), 1.73-1.68 (m, 2H), 1.46-1.37 (m, 2H), 1.35-1.20 (m, 8H), 0.88 (t, J=7.1 Hz, 3H). Endo $^{13}$C NMR (151 MHz, CDCl3 δ 155.08, 144.23, 142.88, 139.44, 137.15, 129.78, 127.72, 127.66, 127.56, 126.61, 126.49, 115.01, 69.46, 55.31, 49.06, 34.55, 34.08, 33.25, 31.67, 29.87, 29.49, 27.97, 22.63, 14.11. Endo LRMS (ESI, APCI) m/z: calc'd for C28H36N [M+H]+ 386.28, found 385.9 Endo FTIR 3079, 3052, 3052, 3018, 2951, 2926, 2854, 1667, 1614, 1598, 1572, 1490, 1458, 1441, 1378, 1330, 1264, 1239, 1180, 1155, 1102, 1074, 1029, 1001, 945, 903, 845, 775, 761, 738, 700, 677 cm-1.

Exo $^1$H NMR (600 MHz, CDCl3) δ 7.33-7.28 (m, 4H), 7.28-7.21 (m, 6H), 5.04 (d, J=1.5 Hz, 1H), 5.03 (d, J=1.4 Hz, 1H), 3.01 (dt, J=5.4, 3.9 Hz, 1H), 2.32-2.26 (m, 1H), 2.08-2.02 (m, 4H), 1.79-1.72 (m, 1H), 1.65-1.60 (m, 1H), 1.42-1.17 (m, 10H), 0.85 (t, J=7.2 Hz, 3H). Exo $^{13}$C NMR (126 MHz, CDCl3) δ 153.82, 143.42, 141.30, 139.03, 137.13, 129.50, 128.11, 127.77, 127.63, 126.71, 126.67, 114.91, 69.20, 61.18, 40.53, 32.10, 31.62, 30.31, 29.69, 29.43, 27.82, 22.57, 14.06. Exo LRMS (ESI, APCI) m/z: calc'd for C28H36N [M+H]+ 386.28, found 385.9 Exo FTIR 3079, 3052, 3018, 2953, 2926, 2855, 1618, 1597, 1572, 1491, 1458, 1440, 1378, 1331, 1264, 1181, 1155, 1074, 1028, 962, 901, 844, 803, 764, 736, 700, 679 cm-1.

(endo or exo) 5-hexyl-4-phenyl-3a-(1-phenylvinyl)-1,2,3,3a,6,6a-hexahydropentalen-1-yl)-1H-1,2,3-triazole (34 endo, 34 exo)

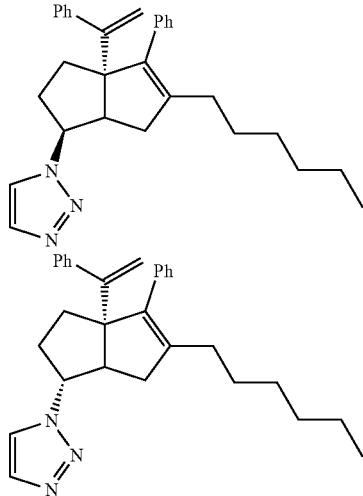

In a 20 dram vial, ascorbic acid (1.0 equiv.) and potassium carbonate (6.0 equiv.) were dissolved in water. Copper sulfate pentahydrate (1.0 equiv.) was then added and the reaction was stirred briefly. Trimethysilyl acetylene (6.0 equiv.) was added in MeOH and the crude mixture of required azide isomer (31 endo or 31 exo) (1.0 equiv.) was subsequently added. The reaction mixture was allowed to stir overnight before dilution with water and extraction with EtOAc. The combined organics were washed with brine and dried over MgSO4 before concentration in vacuo. The crude oil was purified by silica gel chromatography in 30% EtOAc/hexanes.

Endo $^1$H NMR (600 MHz, CDCl3) δ 7.70 (s, 1H), 7.49 (s, 1H), 7.36-7.25 (m, 8H), 7.24-7.21 (m, 2H), 5.14 (s, 1H), 5.00 (s, 1H), 4.96 (ddd, J=11.5, 9.5, 6.7 Hz, 1H), 2.94 (td, J=9.2, 1.9 Hz, 1H), 2.29-2.20 (m, 2H), 2.03-1.84 (m, 5H), 1.27-1.09 (m, 9H), 0.81 (t, J=7.0 Hz, 3H). Endo $^{13}$C NMR (126 MHz, CDCl3) δ 153.77, 143.46, 138.44, 133.33, 129.70, 127.91, 127.83, 127.69, 127.03, 126.93, 122.88, 115.86, 69.13, 63.41, 48.60, 35.66, 32.60, 31.54, 29.74, 29.39, 29.34, 27.65, 22.55, 14.06. Endo LRMS (ESI, APCI) m/z: calc'd for C30H38N3 [M+H]+ 440.3, found 440.4 Endo FTIR (neat): 3080, 3053, 2956, 2927, 2854, 1598, 1573, 1491, 1441, 1288, 1073, 1029, 905, 775, 702 cm-1.

Exo $^1$H NMR (600 MHz, CDCl3) δ 7.66 (s, 1H), 7.43 (s, 1H), 7.37-7.20 (m, 10H), 5.13 (dd, J=0.9 Hz, 1H), 5.09 (d, J=0.9 Hz, 1H), 4.79-4.72 (m, 1H), 2.79 (dd, J=8.6, 3.8 Hz, 1H), 2.41 (dd, J=17.2, 8.6 Hz, 1H), 2.28 (d, J=17.5 Hz, 1H), 2.18-1.98 (m, 4H), 1.85-1.77 (m, 1H), 1.40-1.33 (m, 2H), 1.29-1.16 (m, 7H), 0.85 (t, J=7.1 Hz, 3H). Exo $^{13}$C NMR (101 MHz, CDCl3) δ 153.39, 143.17, 141.25, 139.19, 136.72, 129.56, 127.96, 127.87, 127.77, 127.08, 126.92, 121.73, 115.68, 109.99, 69.99, 69.30, 53.10, 41.18, 32.97, 32.88, 31.61, 29.75, 29.41, 27.82, 22.58, 14.08. Exo LRMS (ESI, APCI) m/z: calc'd for C30H38N3 [M+H]+ 4.3, found 439.3 Exo FTIR (neat): 3088, 3055, 2955, 2925, 2855, 1599, 1491, 1446, 1265, 1074, 910, 773, 703 cm-1.

N-((endo or exo)-5-hexyl-4-phenyl-3a-(1-phenylvinyl)-1,2,3,3a,6,6a-hexahydropentalen-1-yl)acetamide (35 endo, 35 exo)

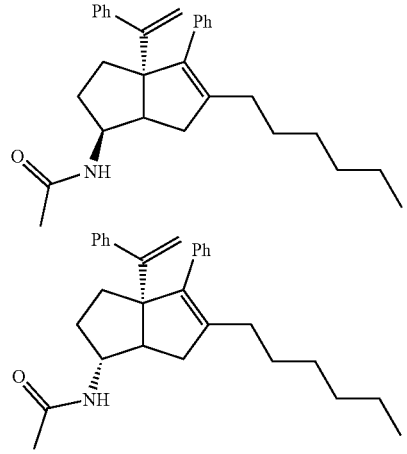

A DCM solution of acetyl chloride (1.5 equiv.) was cooled to 0° C., and slowly treated with a solution of the required amine isomer (33 endo or 33 exo) (1.0 equiv.) in DCM, followed by triethylamine (3.0 equiv.); the resulting solution was stirred for one hour. The solution was then diluted with water and extracted with DCM. The combined organic layers were then washed with water and brine, dried with Na2SO4, filtered, and concentrated in vacuo. The oil was then purified by silica gel chromatography in 35% EtOAc/Hex to afford the title compound as a yellow oil. (71%)

Endo $^1$H NMR (500 MHz, CDCl3) δ 7.35-7.27 (m, 5H), 7.25-7.22 (m, 5H), 5.35 (d, J=8.1 Hz, 1H), 5.06 (d, J=1.5 Hz, 1H), 5.02 (d, J=1.5 Hz, 1H), 4.25 (dtd, J=10.5, 8.6, 6.2 Hz, 1H), 2.66 (ddd, J=16.9, 8.4, 1.6 Hz, 1H), 2.14-2.00 (m, 4H), 1.99 (s, 3H), 1.87 (dtd, J=11.7, 6.0, 2.3 Hz, 1H), 1.76 (td, J=12.2, 11.7, 5.8 Hz, 1H), 1.66 (ddd, J=12.7, 5.9, 2.3 Hz, 1H), 1.43-1.26 (m, 1H), 1.30-1.18 (m, 8H), 0.87 (t, J=7.0 Hz, 3H). Endo $^{13}$C NMR (126 MHz, CDCl3) δ 169.34, 154.62, 143.56, 141.66, 138.87, 137.23, 129.62, 127.87, 127.78, 127.74, 126.87, 126.64, 114.82, 68.95, 59.48, 54.41, 40.86, 32.98, 32.10, 31.64, 29.80, 29.42, 27.82, 25.99, 23.56, 22.59, 14.08. Endo LRMS (ESI, APCI) m/z: calc'd for C30H39NO [M+H]+ 430.3, found 430.3 Endo FT-IR (neat): 3284, 3079, 3055, 2954, 2924, 2853, 1646, 1551, 1491, 1441, 1375, 1301, 1249, 902, 774, 701, 668 cm-1.

Exo $^1$H NMR (500 MHz, CDCl3) δ 7.35-7.25 (m, 8H), 7.27-7.19 (m, 2H), 5.35 (d, J=7.4 Hz, 1H), 5.07 (s, 2H), 3.96 (dd, J=8.2, 4.0 Hz, 1H), 2.34 (dd, J=17.2, 8.6 Hz, 1H), 2.25 (d, J=7.1 Hz, 1H), 2.22-2.16 (m, 1H), 2.08-2.02 (m, 2H), 1.93 (s, 3H), 1.90-1.82 (m, 2H), 1.75-1.66 (m, 1H), 1.40-1.14 (m, 9H), 0.86 (t, J=7.1 Hz, 3H). Exo $^{13}$C NMR (126 MHz, CDCl3) δ 169.45, 154.32, 143.48, 143.00, 141.25, 139.28, 136.88, 129.47, 127.99, 127.79, 127.65, 126.72, 114.96, 69.04, 53.14, 47.38, 35.24, 32.05, 31.68, 29.90, 29.55, 28.13, 23.34, 22.62, 14.09. Exo LRMS (ESI, APCI) m/z: calc'd for C30H39NO [M+H]+ 430.3, found 430.3 Exo FTIR (neat): 3280, 3079, 3055, 2955, 2854, 1646, 1598, 1550, 1491, 1441, 1375, 1304, 1178, 1074, 1029, 903, 766, 701, 668 cm-1.

1-((endo or exo)-5-hexyl-4-phenyl-3a-(1-phenylvi-
nyl)-1, 2, 3, 3a, 6, 6a-hexahydropentalen-1-yl)urea
(36 endo, 36 exo)

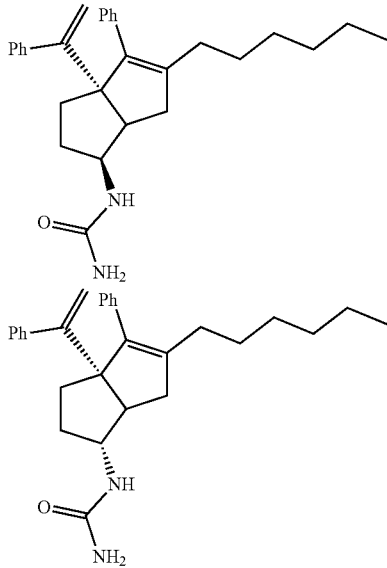

To a reaction flask charged with the required amine isomer (33 endo or 33 exo) (1.0 equiv.) and sodium cyanate (10.0 equiv.) was added water and 1M aqueous hydrochloric acid (2.0 equiv.). The reaction mixture was heated to 90° C. and stirred for approximately 72 hours at this temperature before being diluted with 3M aqueous NaOH and extracted with Et2O. The combined organic layers were then washed with water and brine, dried with Na2SO4, filtered, and concentrated in vacuo. The oil was then purified by silica gel chromatography in EtOAc to afford the title compound as a white solid. (Endo: 6.9 mg, 41%; Exo: 4.5 mg, 37%).

Endo $^1$H NMR (600 MHz, CDCl3) δ 7.34-7.19 (m, 10H), 5.06 (d, J=1.4 Hz, 1H), 4.99 (d, J=1.4 Hz, 1H), 4.48 (d, J=7.7 Hz, 1H), 4.32 (s, 2H), 3.97 (s, 1H), 2.60 (t, J=8.7 Hz, 1H), 2.22 (d, J=17.3 Hz, 1H), 2.09-2.03 (m, 2H), 1.93-1.85 (m, 1H), 1.73 (td, J=12.5, 5.7 Hz, 1H), 1.67 (ddd, J=12.9, 6.1, 1.9 Hz, 1H), 1.39-1.31 (m, 2H), 1.29-1.17 (m, 8H), 0.86 (t, J=7.1 Hz, 3H). Endo $^{13}$C NMR (126 MHz, CDCl3) δ 157.89, 154.39, 143.57, 143.15, 139.01, 136.83, 129.54, 127.88, 127.72, 127.68, 126.76, 126.69, 115.11, 69.16, 47.58, 35.05, 32.13, 31.87, 31.63, 29.89, 29.51, 27.97, 22.60, 14.07. Endo LRMS (ESI, APCI) m/z: calc'd for C29H37N2O [M+H]+ 429.7, found 428.9 Endo FT-IR (neat): 3348, 3080, 3053, 3018, 2952, 2923, 2853, 1740, 1655, 1599, 1552, 1491, 1458, 1377, 1341, 1287, 1234, 1212, 1156, 1104, 1075, 1029, 966, 902, 860, 773, 763, 725, 701, 669 cm-1.

Exo $^1$H NMR (600 MHz, CDCl3) δ 7.34-7.19 (m, 10H), 5.06 (d, J=1.3 Hz, 1H), 5.03 (d, J=1.4 Hz, 1H), 4.42 (d, J=7.4 Hz, 1H), 4.25 (s, 2H), 3.70 (s, 1H), 2.36 (dd, J=17.2, 8.9 Hz, 1H), 2.22-2.17 (m, 2H), 2.05 (q, J=7.0 Hz, 2H), 1.94-1.80 (m, 2H), 1.72-1.66 (m, 1H), 1.59-1.52 (m, 1H), 1.33 (q, J=7.4 Hz, 2H), 1.28-1.17 (m, 6H), 0.85 (t, J=7.2 Hz, 3H). Exo $^{13}$C NMR (126 MHz, CDCl3) δ 157.74, 154.49, 143.59, 141.50, 138.97, 137.17, 129.61, 127.83, 127.77, 127.71, 126.84, 126.65, 114.89, 68.96, 60.87, 54.41, 41.05, 32.81, 32.37, 31.62, 29.76, 29.69, 29.40, 27.81, 22.57, 14.06. Exo LRMS (ESI, APCI) m/z: calc'd for C29H37N2O [M+H]+ 429.7, found 428.9 Exo FTIR (neat): 3317, 3079, 3053, 3018, 2954, 2923, 2854, 1641, 1591, 1545, 1491, 1459, 1440, 1378, 1339, 1261, 1195, 1182, 1157, 1075, 1028, 903, 844, 803, 775, 764, 720, 700, 669 cm-1.

(endo or exo)-5-hexyl-4-phenyl-3a-(1-phenylvinyl)-
1,2,3,3a,6,6a-hexahydropentalen-1-yl sulfamide (37
endo or 37 exo)

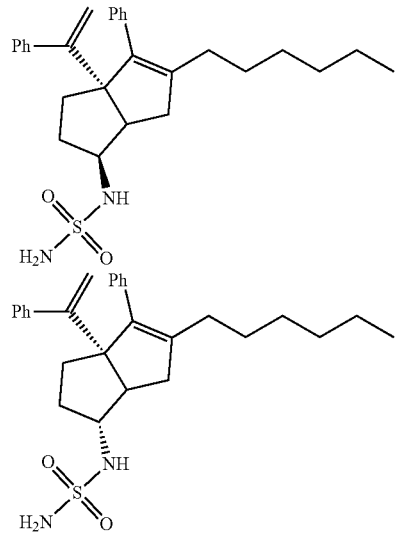

To a solution of the required amine isomer (33 endo or 33 exo) (1.1 equiv.) and triethylamine (2.0 equiv.) in DCM under nitrogen was added a 0.5M solution of 2-oxo-1,3-oxazolidine-3-sulfonyl chloride in DCM (1.0 equiv.) (prepared according to the procedure of Borghese et al.). The resulting solution was stirred at room temperature for three hours then concentrated in vacuo to a solid. To the resulting crude solid was added ammonia (0.5M in dioxane, 1.5 equiv.) and triethylamine (3.0 equiv.). The solution was then heated in a sealed tube to 85° C. overnight. After cooling to room temperature, the reaction was diluted with 3:3:94 MeOH:Et3N:EtOAc then passed through a pad of silica. The eluent was concentrated in vacuo and purified by silica gel chromatography in 20-30% EtOAc/hexanes to afford the title compound as a colorless oil. (Endo: 21.6 mg, 60%; Exo: 5.4 mg, 36%)

Endo $^1$H NMR (600 MHz, CDCl3) δ 7.33-7.23 (m, 8H), 7.20-7.17 (m, 2H), 5.09 (d, J=1.3 Hz, 1H), 4.96 (d, J=1.3 Hz, 1H), 4.44 (s, 2H), 4.36 (d, J=8.0 Hz, 1H), 3.84-3.77 (m, 1H), 2.62 (td, J=8.9, 2.0 Hz, 1H), 2.38 (dd, J=17.5, 2.0 Hz, 1H), 2.20-2.13 (m, 1H), 2.08-2.04 (m, 2H), 2.00-1.95 (m, 1H), 1.74-1.70 (m, 2H), 1.50-1.43 (m, 1H), 1.42-1.16 (m, 8H), 0.86 (t, J=7.1 Hz, 3H). Endo $^{13}$C NMR (126 MHz, CDCl3) δ 154.13, 143.56, 142.84, 139.30, 136.58, 129.64, 127.80, 127.74, 126.87, 126.78, 115.49, 68.80, 57.16, 47.44, 35.42, 32.32, 31.97, 31.60, 29.83, 29.48, 27.92, 22.59, 14.07. Endo LRMS (ESI, APCI) m/z: calc'd for C28H37N2O2S [M+H]+ 465.7, found 464.8 Endo FT-IR (neat): 3278, 3080, 3053, 3019, 2954, 2926, 2854, 1718, 1618, 1598, 1571, 1491, 1440, 1323, 1160, 1118, 1095, 1075, 1029, 1014, 906, 774, 763, 720, 700 cm-1.

Exo $^1$H NMR (600 MHz, CDCl3) δ 7.34-7.24 (m, 8H), 7.23-7.18 (m, 2H), 5.08 (d, J=1.2 Hz, 1H), 5.01 (d, J=1.2 Hz, 1H), 4.38 (s, 2H), 4.21 (d, J=7.2 Hz, 1H), 3.58-3.52 (m, 1H), 2.40 (dd, J=16.9, 8.9 Hz, 1H), 2.36-2.31 (m, 1H), 2.18 (d, J=16.9 Hz, 1H), 2.05 (td, J=7.5, 2.6 Hz, 2H), 1.99-1.85 (m, 2H), 1.76-1.69 (m, 2H), 1.38-1.30 (m, 1H), 1.30-1.15 (m, 7H), 0.86 (t, J=7.2 Hz, 3H). Exo $^{13}$C NMR (126 MHz, CDCl3) δ 154.08, 143.53, 141.15, 139.27, 136.94, 129.62, 127.86, 127.74, 126.93, 126.75, 115.21, 68.77, 63.78, 54.03, 40.83, 32.84, 32.30, 31.62, 29.71, 29.69, 29.37, 27.81, 22.57, 14.05. Exo LRMS (ESI, APCI) m/z: calc'd for C29H37N2O [M+H]+ 465.7, found 464.8 Exo FTIR (neat): 3277, 3080, 3053, 3018, 2923, 2854, 1720, 1621, 1598, 1572, 1491, 1455, 1441, 1376, 1321, 1158, 1075, 1029, 969, 903, 765, 723, 701, 668 cm-1.

endo or exo 5-hexyl-4-phenyl-3a-(1-phenylvinyl)-1, 2,3,3a,6,6a-hexahydropentalene-1-carboxamide (38 endo, 38 exo)

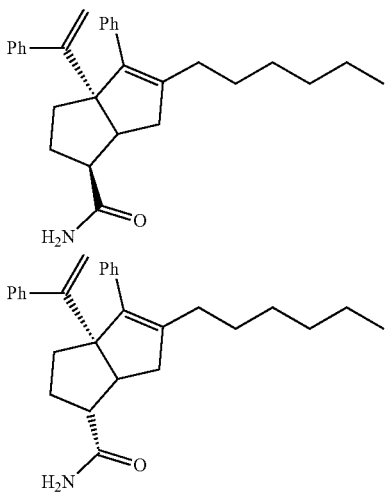

To a flame dried round bottom flask was added potassium hydroxide (10.0 eq) which was suspended in THF (0.1 M). The required nitrile isomer (32 endo or 32 exo) (1.0 eq) was then added in THF dropwise and the resulting solution was heated to 65° C. for 48 hours. The solution was then washed with water (3×) and EtOAc (3×). The combined organic layers were then washed with water and brine. The resulting solution was dried with Na2SO4 and evaporated to dryness. The oil was then purified via column chromatography in 5-10% EtOAc/hexanes.

Endo $^1$H NMR (400 MHz, Chloroform-d) δ 7.35-7.18 (m, 10H), 5.12 (m, 1H), 5.02 (m, 1H), 3.60 (dt, J=18.3, 6.6 Hz, 1H), 2.77-2.66 (m, 1H), 2.40-2.16 (m, 1H), 2.11-1.99 (m, 2H), 1.93-1.75 (m, 1H), 1.66-1.56 (m, 2H), 1.47-1.23 (m, 4H), 0.97-0.76 (m, 3H). LCMS (90% MeCN/H2O): 2.15 min, m/z 414.2.

Exo $^1$H NMR (400 MHz, Chloroform-d) δ 7.35-7.18 (m, 10H), 5.12 (m, 1H), 5.02 (m, 1H), 3.43 (bs, 1H), 2.40-2.16 (m, 1H), 2.11-1.99 (m, 4H), 1.93-1.75 (m, 6H), 1.47-1.23 (m, 10H), 0.84 (td, J=7.2, 1.1 Hz, 3H). LCMS (90% MeCN/H2O): 2.34 min, m/z 414.7.

(endo or exo)-5-hexyl-4-phenyl-3a-(1-phenylethyl)-1,2,3,3a,6,6a-hexahydropentalen-1-ol (39 endo, 39 exo)

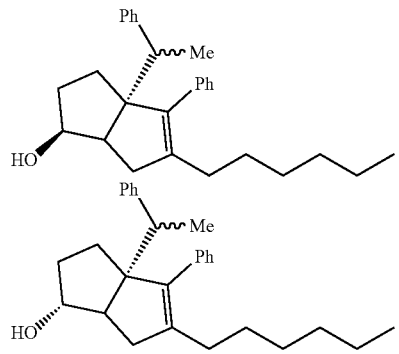

A flame dried round bottom flask charged with Pd/C (10 wt %) and was placed under argon. The solid was suspended in EtOAc (0.1 M) and the appropriate diastereomer of RJW100 (1.0 eq) was added dropwise in EtOAc (0.1 M). The resulting solution was backfilled with hydrogen and stirred for 18 hours. The mixture was then filtered through a plug of silica and evaporated to dryness. The resulting oil was purified via column chromatography in 5-10% EtOAc/hexanes.

Endo $^1$H NMR (600 MHz, Chloroform-d) δ 7.18-6.99 (p, J=2.2 Hz, 6H), 6.98-6.93 (m, 2H), 6.58-6.54 (m, 2H), 4.49 (dt, J=11.6, 6.6 Hz, 1H), 2.68 (d, J=6.2 Hz, 1H), 2.60-2.55 (m, 1H), 2.53-2.46 (m, 1H), 2.18-2.08 (m, 2H), 2.04 (dt, J=11.8, 7.5 Hz, 1H), 1.68-1.57 (m, 2H), 1.37 (dd, J=14.0, 9.6 Hz, 2H), 1.18 (d, J=6.3 Hz, 3H), 1.15-0.96 (m, 6H), 0.77 (t, J=7.3 Hz, 3H). Endo $^{13}$C NMR (600 MHz, Chloroform-d) δ 145.77, 141.05, 128.35, 127.33, 127.28, 125.50, 125.36, 77.22, 75.72, 64.65, 60.06, 53.58, 44.25, 44.01, 33.86, 32.73, 32.07, 31.76, 30.37, 29.71, 29.44, 28.50, 22.52, 20.11, 14.03.

Exo $^1$H NMR (600 MHz, Chloroform-d) δ 7.08-7.00 (m, 3H), 6.95-6.88 (m, 3H), 6.68 (d, J=7.3 Hz, 2H), 6.58 (d, J=7.3 Hz, 2H), 4.20 (dt, J=5.0, 2.2 Hz, 1H), 2.77 (d, J=6.5 Hz, 1H), 2.53 (d, J=10.5 Hz, 1H), 2.24-1.98 (m, 5H), 1.80 (qd, J=8.0, 7.5, 3.4 Hz, 1H), 1.64 (ddd, J=13.6, 9.1, 4.5 Hz, 2H), 1.48 (dd, J=13.7, 7.1 Hz, 5H), 1.32 (d, J=6.7 Hz, 3H), 1.16-0.94 (m, 9H), 0.85 (t, J=7.1 Hz, 3H). Exo $^{13}$C NMR (400 MHz, Chloroform-d) δ 146.99, 140.97, 130.62, 128.24, 127.14, 127.03, 125.20, 124.75, 83.37, 77.19, 64.16, 62.14, 57.43, 45.46, 42.60, 38.19, 36.77, 36.36, 31.72, 31.29, 29.93, 29.69, 29.39, 28.42, 22.49, 21.08, 14.01.

((((endo or exo)-5-hexyl-4-phenyl-3a-(1-phenylvinyl)-1, 2, 3, 3a, 6,6a-hexahydropentalen-1-yl)oxy)carbonyl)sulfamic acid (40 endo, 40 exo)

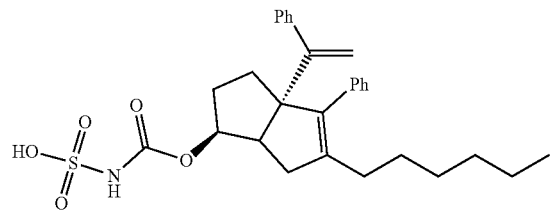

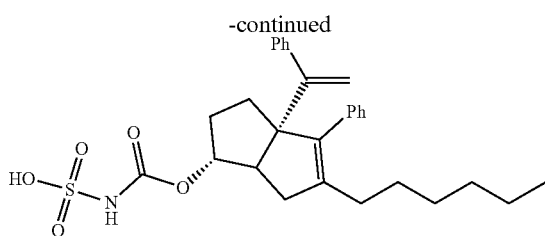

In a flame dried round bottom flask was added the appropriate isomer (29 endo, or 29 exo) in ACN (0.1 M). Chlorosulfonyl isocyanate (2.0 eq) was added after cooling the solution to −15° C. After stirring around 10 minutes, water (0.04 M) was added and heated at 60° C. for around 18 hours. After cooling to room temperature, the resulting solution was quenched with water and adjusted to pH 5. The resulting solution was extracted with EtOAc (3×). The combined organic layers were then dried with Na2SO4 and evaporated to dryness. The resulting oil was purified via column chromatography in 50% EtOAc/hex.

Endo $^1$H NMR (400 MHz, Chloroform-d) δ 7.32-7.17 (m, 11H), 5.05 (d, J=1.4 Hz, 1H), 4.96-4.87 (m, 2H), 4.62 (s, 1H), 2.66 (td, J=8.9, 1.9 Hz, 1H), 2.33 (dd, J=16.5, 1.4 Hz, 1H), 2.10-1.96 (m, 5H), 1.93-1.86 (m, 1H), 1.70-1.60 (m, 3H), 1.31-1.18 (m, 9H), 0.89-0.84 (m, 3H).

Exo $^1$H NMR (400 MHz, Chloroform-d) δ 7.32-7.18 (m, 10H), 5.04 (d, J=1.5 Hz, 1H), 4.98 (d, J=1.5 Hz, 1H), 4.75-4.70 (m, 1H), 2.37 (td, J=8.9, 1.1 Hz, 1H), 2.34-2.27 (m, 1H), 2.18-2.15 (m, 1H), 2.04-1.91 (m, 6H), 1.78-1.65 (m, 3H), 1.36-1.15 (m, 9H), 0.84 (t, J=7.0 Hz, 3H).

(endo or exo)-5-hexyl-4-phenyl-3a-(1-phenylvinyl)-1,2,3,3a,6,6a-hexahydropentalen-1-yl sulfamoylcarbamate (41 endo, 41 exo)

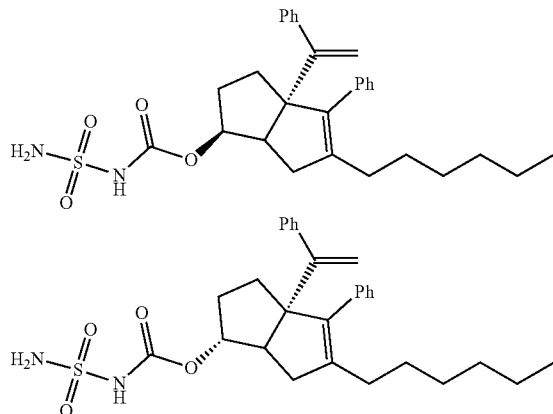

In a flame dried round bottom flask was added 6 in ACN (0.1 M) and chlorosulfonyl isocyanate (2.0 eq) was subsequently added after cooling the solution to −15° C. After stirring around 10 minutes, ammonium hydroxide (0.04 M) was added and heated at 60° C. for around 18 hours. After cooling to room temperature, the resulting solution was quenched with a saturated solution of bicarbonate to pH 9. The resulting solution was extracted with EtOAc (3×). The combined organic layers were then dried with Na2SO4 and evaporated to dryness. The resulting oil was purified via column chromatography in 50% EtOAc/hex with 1% triethylamine.

Exo $^1$H NMR (500 MHz, Chloroform-d) δ 7.36-7.28 (m, 8H), 7.22-7.18 (m, 2H), 5.16 (s, 2H), 5.12 (d, J=1.3 Hz, 1H), 5.00 (d, J=1.3 Hz, 1H), 4.91 (d, J=3.6 Hz, 1H), 2.48-2.41 (m, 2H), 2.21-2.13 (m, 1H), 2.04 (ddd, J=8.6, 3.9, 2.0 Hz, 2H), 1.98-1.75 (m, 5H), 1.39-1.18 (m, 9H), 0.87 (t, J=7.1 Hz, 3H).

Endo $^1$H NMR (500 MHz, Chloroform-d) δ 7.35-7.19 (m, 10H), 5.22 (s, 2H), 5.12-5.04 (m, 2H), 4.97 (d, J=1.3 Hz, 1H), 2.71 (dd, J=8.8, 1.9 Hz, 1H), 2.30 (dd, J=17.3, 1.9 Hz, 1H), 2.12-2.04 (m, 2H), 1.97 (q, J=6.3 Hz, 1H), 1.81-1.69 (m, 3H), 1.40-1.20 (m, 9H), 0.94-0.83 (t, 3H).

5-hexyl-4-phenyl-3a-(1-phenylvinyl)-3,3a,6,6a-tetrahydropentalen-1(2H)-one oxime (42)

A flame dried round bottom flask was charged with hydroxylamine hydrochloride (1.2 eq) and sodium acetate (1.3 eq) before being backfilled with argon. The solids were dissolved in an EtOH/water mixture (4:1, 0.1 M). 27 (1.0 eq) in EtOH was added dropwise and heated at 80° C. for 6 hours. The solution was then washed with water (3×) and EtOAc (3×). The combined organic layers were then washed with water and brine. The resulting solution was dried with Na2SO4 and evaporated to dryness. The oil was then purified via column chromatography in 5% EtOAc/hexanes.

1-ethynyl-5-hexyl-4-phenyl-3a-(1-phenylvinyl)-1,2,3,3a,6,6a-hexahydropentalen-1-ol (43)

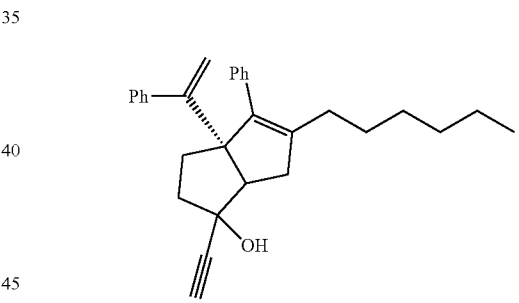

A solution of 27 (1.0 eq) in dry THF was cooled to −78° C. in a flame dried round bottom flask under nitrogen. Ethynyl magnesium bromide (0.5 M, 1.5 eq) was then added dropwise. The resulting solution was stirred for 20 hours to room temperature. Ammonium chloride was added to the solution and extracted with EtOAc (3×). The combined organic layers were dried with Na2SO4 and evaporated to dryness. The resulting oil was purified in 0-10% EtOAc/hex.

Endo $^1$H NMR (400 MHz, Chloroform-d) δ 7.34-7.14 (m, 10H), 5.06 (s, 1H), 5.00 (d, J=1.4 Hz, 1H), 4.11 (qd, J=7.1, 1.1 Hz, 1H), 2.73-2.58 (m, 2H), 2.44 (d, J=0.8 Hz, 1H), 2.12-1.81 (m, 5H), 1.74 (dt, J=12.2, 5.4 Hz, 1H), 1.36 (q, J=7.4 Hz, 2H), 1.32-1.12 (m, 9H), 0.84 (t, J=6.8 Hz, 3H). $^{13}$C NMR (101 MHz, Chloroform-d) δ 154.45, 143.66, 142.53, 139.19, 136.87, 129.76, 127.90, 127.69, 127.67, 126.73, 126.65, 114.90, 88.50, 75.17, 71.45, 68.71, 57.12, 39.84, 34.46, 32.40, 31.63, 29.78, 29.42, 27.86, 22.58, 21.06, 14.19, 14.08.

(endo or exo) (5-hexyl-4-phenyl-3a-(1-phenylvi-nyl)-1,2,3,3a,6,6a-hexahydropentalen-1-10 yl)methanamine (48)

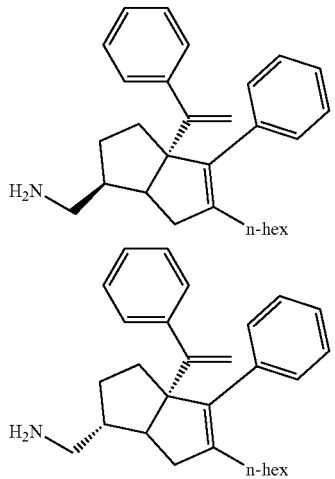

To an oven-dried reaction tube under nitrogen was added lithium aluminum hydride. After being suspended in ether, the appropriate diastereomer of 32 (1.0 equiv.) in ether was added dropwise. The reaction mixture was allowed to stir for 18 h before being quenched with water and 1M NaOH before being filtered through celite and evaporated in vacuo. The resulting crude oil was purified on basified silica in 10% MeOH/DCM

(endo or exo) 5-hexyl-4-phenyl-3a-(1-phenylvinyl)-1,2,3,3a,6,6a-hexahydropentalen-1-yl dihydrogen phosphate (49)

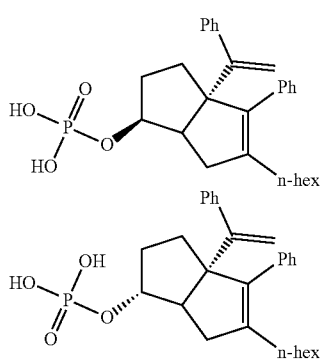

In a reaction vial under nitrogen, RJW100 (1.0 equiv.) was dissolved in acetonitrile. To the reaction vial was added trimethylamine (4.0 equiv.) and phosphoryl chloride (2.0 equiv.) The reaction was stirred at room temperature under nitrogen for 4 h before being quenched with water (excess) and concentrated. The resulting crude residue was purified on basified silica in 10% MeOH/DCM.

(endo or exo)-5-hexyl-4-phenyl-3a-(1-phenylvinyl)-1,2,3,3a,6,6a-hexahydropentalen-1-yl carbamoylsulfamate (50)

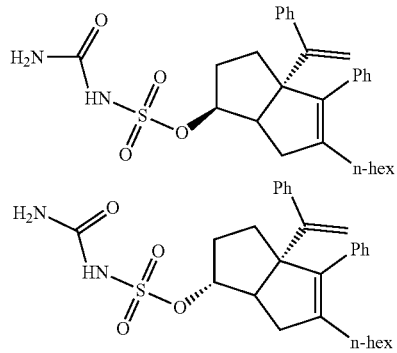

In a reaction tube under nitrogen was added NaH (1.5 equiv.) in THF. The solution was cooled to 0 C before the addition of a solution of the required sulfamate (28 endo, 28 exo) (1.0 equiv.) in THF. A solution of carbonyldiimidazole (2.0 equiv.) in THF was added and the reaction mixture was allowed to warm to room temperature. After stirring for 1 h, ammonia (7N in MeOH) was added dropwise and stirred for ~3 h. After allowing to stir, the reaction was diluted with EtOAc and washed with brine (ensuring the aqueous layer was basic). The organic layer was dried with MgSO4, filtered, and concentrated in vacuo. The crude oil was purified on silica in 50% EtOAc to 10% MeOH/DCM.

Endo: $^1$H NMR (400 MHz, Chloroform-d) δ 7.35 (s, 2H), 7.32-7.25 (m, 4H), 7.24-7.21 (m, 2H), 7.16 (ddd, J=7.2, 3.6, 1.8 Hz, 2H), 5.08 (d, J=1.2 Hz, 1H), 5.06-4.97 (m, 1H), 4.93-4.89 (m, 1H), 4.89-4.80 (m, 1H), 3.74 (s, 2H), 2.67 (td, J=8.8, 2.3 Hz, 1H), 2.62-2.48 (m, 1H), 2.12 (ddd, J=17.8, 9.1, 3.9 Hz, 1H), 2.06-2.00 (m, 1H), 1.76 (ddd, J=8.5, 6.4, 3.4 Hz, 1H), 1.67 (td, J=12.6, 5.7 Hz, 1H), 1.35 (d, J=6.4 Hz, 4H), 1.28-1. 16(m, 7H), 0.83 (t, J=7.0 Hz, 3H). LRMS [ESI–APCI] calc'd for C28H33 [M–CH3N2O4S]+ 369.3, found 369.2

Exo: $^1$H NMR (400 MHz, Chloroform-d) δ 7.28-7.25 (m, 2H), 7.24-7.22 (m, 1H), 7.20-7.12 (m, 5H), 5.39 (d, J=48.0 Hz, 1H), 4.98 (s, 1H), 4.93 (s, 1H), 4.69 (s, 1H), 3.54 (s, 3H), 2.64-2.55 (m, 1H), 2.33-2.18 (m, 1H), 1.74-1.57 (m, 2H), 1.31-1.10 (m, 14H), 0.81 (t, J=7.1 Hz, 3H). Exo LRMS [ESI–APCI] calc'd for C28H33 [M-CH$_3$N$_2$O4S]+ 369.3, found 369.2

5'-hexyl-4'-phenyl-3a'-(1-phenylvinyl)-3',3a',6',6a'-tetrahydro-2'H-spiro[oxirane-5 2,1'-pentalene]

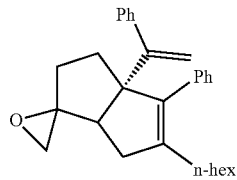

Trimethylsilyliodide (3.0 equiv.) was dissolved in a reaction vial open to air. Potassium Hydroxide (12.0 equiv.) was added and stirred until dissolved, then water (~20 equiv.)

was added. 27 in acetonitrile was added to the reaction mixture before the reaction was heated to 60° C. for 16 h. The reaction mixture was then cooled to room temperature and filtered through celite. The filtrate was then poured onto water and extracted three times with EtOAc. The organic layers were concentrated in vacuo and the crude oil was purified on silica in 5-10% EtOAc/Hex.

3-(aminomethyl)-5-hexyl-6-phenyl-6a-(1-phenylvinyl)-1,2,3,3a,4,6a-hexahydropentalen-2-ol

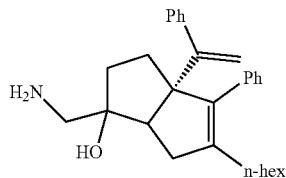

In a reaction tube under nitrogen, the prepared expoxide 5'-hexyl-4'-phenyl-3a'-(1-phenylvinyl)-3',3a',6',6a'-tetrahydro-2'H-spiro[oxirane-5 2,1'-pentalene] (1.0 equiv.) was dissolved in acetonitrile. Ammonia in methanol (7N, excess) was added. The reaction tube was capped and heated to 60 C for 18 h. The reaction mixture was then cooled to room temperature and concentrated in vacuo. The resulting crude oil was purified on silica in 10% MeOH/DCM. ((5-hexyl-4-phenyl-3a-(1-phenylvinyl)-3,3a,6,6a-tetrahydropentalen-1-yl)oxy)triethyl silane Under nitrogen, freshly prepared lithium diisopropylamide (1.1 equiv.) was added to THF and the solution was cooled to −78 C and 27 (1.0 equiv.) in THF was added. The reaction mixture was stirred at −78 C for 20 minutes before the addition of triethylsilyl chloride (2.1 equiv.). The reaction mixture was stirred for 1.5 h and allowed to warm to room temperature before being quenched with ammonium chloride. The crude mixture was then extracted with ethyl acetate. The organic layers were washed with brine, dried with magnesium sulfate, and concentrated in vacuo. The resulting crude oil was purified on silica in 5% EtOAc/Hex.

(exo or endo) 5-hexyl-2-hydroxy-4-phenyl-3a-(1-phenylvinyl)-3,3a,6,6a-tetrahydropentalen-1(2H)-one

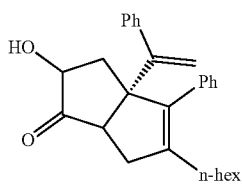

Sodium bicarbonate (5.0 equiv.) and meta-chloroperoxybenzoic acid (1.2 equiv.) were added in a reaction tube and backfilled with nitrogen. Hexanes was added and the resulting suspension was cooled to −15° C. ((5-hexyl-4-phenyl-3a-(1-phenylvinyl)-3,3a,6,6a-tetrahydropentalen-1-yl)oxy) triethylsilane (1.0 equiv.) in hexane was added to the reaction tube and the resulting mixture was allowed to stir for 1 h before being poured onto water and extracted with ethyl acetate. The organic layers were washed with brine, dried with magnesium sulfate and concentrated in vacuo. The resulting crude oil was purified in 10% EtOAc/Hex.

5-hexyl-4-phenyl-3a-(1-phenylvinyl)-1,2,3,3a,6,6a-hexahydropentalene-1,2-diol (52)

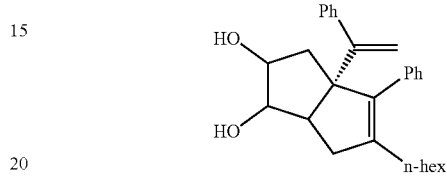

(exo or endo) 5-hexyl-2-hydroxy-4-phenyl-3a-(1-phenylvinyl)-3,3a,6,6a-tetrahydropentalen-1(2H)-one (1.0 equiv.) was dissolved in methanol and sodium borohydride (excess) was added. The reaction mixture was stirred until effervescence ceased. The crude reaction mixture was poured onto water and extracted with EtOAc, dried with magnesium sulfate and concentrated in vacuo. The resulting crude oil was purified on silica in 50% EtOAc/Hex.

Synthesis of Additional Derivatives

The synthetic procedure for preparing compounds 44, 45a, 45b, 46a, 46b, and 45c is provided for in FIG. 8.

10-(6-oxo-3-phenyl-3a-(1-phenylvinyl)-1,3a,4,5,6,6a-hexahydropentalen-2-yl)decanoic acid (44)

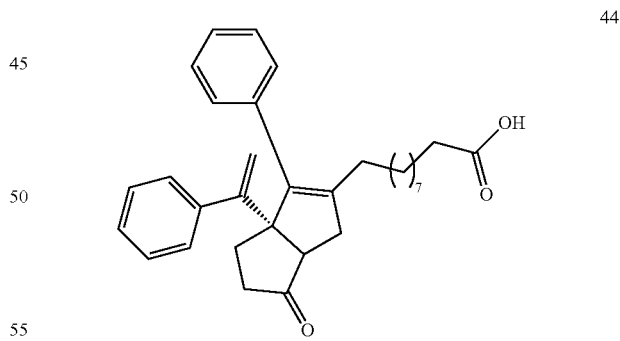

A solution of 11f (1.0 equiv.) in acetonitrile was treated with N-methylmorpholine oxide (1.5 equiv.) and allowed to stir to homogeneity before the addition of tetrapropylammonium perruthenate (0.1 equiv.) The solution was stirred at room temperature until completion as determined by TLC (~10 min). The solution was concentrated in vacuo and subjected directly to silica gel chromatography in 10% EtOAc/Hex to afford the title compound as a clear, colorless oil.

10-(endo)-6-hydroxy-3-phenyl-3a-(1-phenylvinyl)-1,3a,4,5,6,6a-hexahydropentalen-2-yl)decanoic acid (45a)

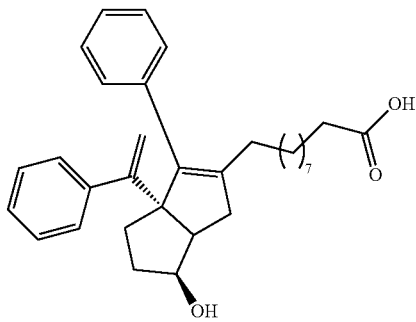

In a scintillation vial, 44 was dissolved in MeOH. Sodium borohydride (1.1 equiv.) was added, and the reaction was allowed to stir to completion (30 min). The mixture was then concentrated and passed through a short plug of silica (eluted with EtOAc). The reaction is selective for the endo diastereomer shown in 45a.

10-(endo)-3-phenyl-3a-(1-phenylvinyl)-6-(sulfamoyloxy)-1,3a,4,5,6,6a-hexahydropentalen-2-yl)decanoic acid (45b)

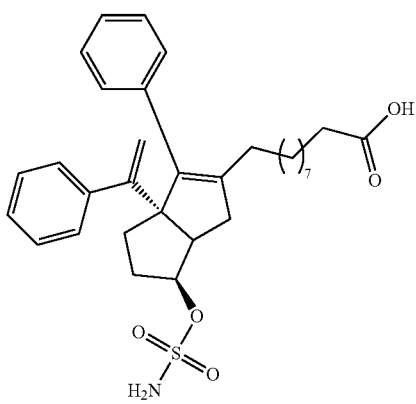

In a scintillation vial, 45a was dissolved in DMA. Sulfamoyl chloride (1.1 equiv.) was added and allowed to stir for 1 hour before the addition of triethylamine (1.1 equiv.). The reaction mixture was then allowed to stir for an additional 10 minutes. The resulting solution was concentrated and purified on silica in 20-100% EtOAc/Hex (1% acetic acid).

10-(exo)-3-phenyl-3a-(1-phenylvinyl)-6-(sulfamoyloxy)-1,3a,4,5,6,6a-hexahydropentalen-2-yl)decanoic acid (45c)

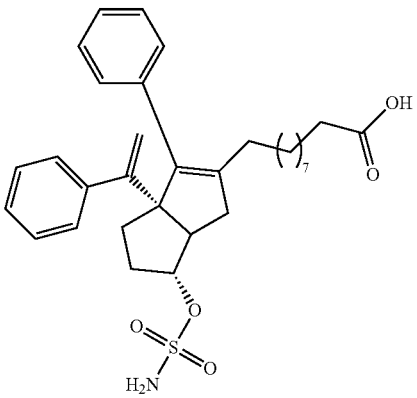

In a scintillation vial, 11f was dissolved in DMA. Sulfamoyl chloride (1.1 equiv.) was added and allowed to stir for 1 hour before the addition of triethylamine (1.1 equiv.) The reaction mixture was then allowed to stir for an additional 10 minutes. The resulting solution was concentrated and purified on silica in 20-100% EtOAc/Hex (1% acetic acid).

$^1$H NMR (500 MHz, Chloroform-d) δ 7.38-7.13 (m, 10H), 5.08 (d, J=1.5 Hz, 1H), 4.99 (d, J=1.5 Hz, 1H), 4.83 (s, 2H), 4.72 (d, J=4.2 Hz, 1H), 2.66 (d, J=9.3 Hz, 1H), 2.35 (t, J=7.4 Hz, 3H), 2.12 (d, J=17.6 Hz, 1H), 2.09-1.93 (m, 7H), 1.87-1.71 (m, 2H), 1.70-1.58 (m, 3H), 1.39-1.10 (m, 10H). $^{13}$C NMR (126 MHz, cdcl3) δ 176.48, 153.48, 143.61, 141.35, 138.91, 136.81, 129.53, 127.81, 127.78, 127.72, 126.88, 115.57, 93.70, 69.29, 52.81, 40.13, 33.32, 32.08, 32.06, 29.43, 29.24, 28.87, 28.83, 28.79, 28.75, 27.51, 24.53. FT-IR (neat): 3475, 3275, 3080, 3053, 3019, 2924, 2853, 1707, 1598, 1572, 1491, 1457, 1440, 1357, 1260, 1181, 1092, 1075, 1027, 927, 904, 800, 763, 701 cm-1.

10-(endo)-6-amino-3-phenyl-3a-(1-phenylvinyl)-1,3a,4,5,6,6a-hexahydropentalen-2-yl)decanoic acid (46a)

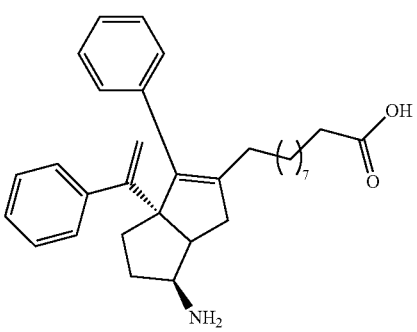

In a reaction vial equipped with stir bar, 44 was dissolved in methanol. Titanium tetraisopropoxide (TiO(iPr)4), (2.0 equiv.) was added portion wise. Ammonia in Methanol (7N) was then added to the reaction mixture and allowed to stir at room temperature for 6 h. Sodium borohydride (2.0 equiv.) was added slowly, and the reaction mixture was stirred until effervescence ceased. The resulting mixture was concentrated and purified on a plug of silica in 65/35/5 DCM/MeOH/NH4OH.

10-(endo)-3-phenyl-3a-(1-phenylvinyl)-6-(sulfamoylamino)-1,3a,4,5,6,6a-hexahydropentalen-2-yl)decanoic acid (46b)

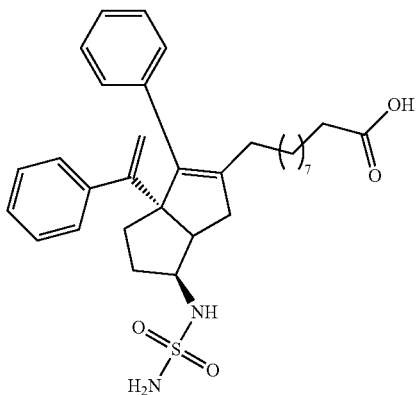

To a solution of the required amine (44) (1.0 equiv.) and triethylamine (2.0 equiv.) in DCM under nitrogen was added a 0.5M solution of 2-oxo-1,3-oxazolidine-3-sulfonyl chloride in DCM (1.0 equiv.) (prepared according to the procedure of Borghese et al.). The resulting solution was stirred at room temperature for three hours then concentrated in vacuo. To the resulting crude solid was added ammonia (0.5M in dioxane, 1.5 equiv.) and triethylamine (3.0 equiv.). The solution was then heated in a sealed tube to 85° C. for 4 h. After cooling to room temperature, the reaction was diluted with 3:3:94 MeOH:Et3N:EtOAc then passed through a pad of silica. The eluent was concentrated in vacuo and purified by silica gel chromatography in 50-100% EtOAc/hexanes (1% Acetic Acid) to afford the title compound as a colorless oil.

(exo or endo)8-(6-hydroxy-3-phenyl-3a-(1-phenylvinyl)-1,3a,4,5,6,6a-hexahydropentalen-2-yl)octyl acetate (47)

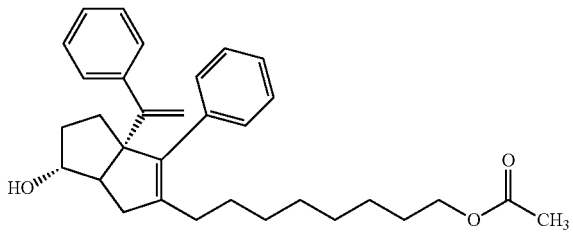 [SMILES: C=C(c1ccccc1)[C@@]12CC[C@@H](O)C1CC(CCCCCCCCOC(C)=O)=C2c1ccccc1]

In an oven-dried vial under nitrogen, the required diol (1.0 equiv.) was dissolved in DCM and cooled to 0° C. Triethylamine (2.0 equiv.) was added to the reaction mixture before acetyl chloride (1.0 equiv.). The mixture was allowed to warm to room temperature and stir for 30 min before being concentrated in vacuo. The crude oil was purified on a glass-backed preparative alumina plate in 30% EtOAc/Hex.

(endo or exo) diethyl (8-(6-hydroxy-3-phenyl-3a-(1-phenylvinyl)-1,3a,4,5,6,6a-hexahydropentalen-2-yl) octyl) phosphate (53)

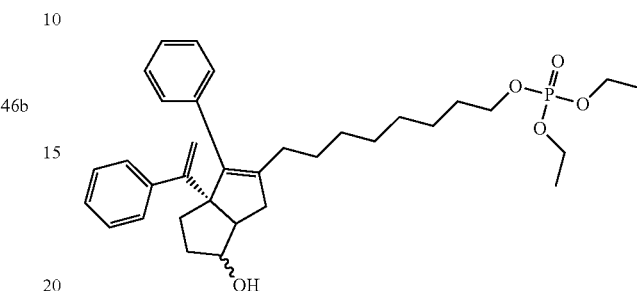

In an oven-dried vial, the required alcohol isomer (1.0 equiv.) was dissolved in DCM. Triethylamine (2.0 equiv.) was added and cooled to 0° C. before diethyl chlorophosphate (1.0 equiv.) was added. The reaction mixture was stirred at room temperature for 18 h before being concentrated in vacuo and purified on a glass-backed preparative alumina plate in 30% EtOAc/Hex.

Biological Evaluation of Novel LRH-1 Agonists and Antagonists.

Protein expression and purification—LRH-1 LBD (residues 299-541) in the pMSC7 vector was expressed in BL21(DE3) pLysS $E.$ $coli$ by induction with IPTG (1 mM) for 4 hr at 30° C. Protein was purified by nickel affinity chromatography. Protein used for Thermofluor experiments was incubated with DLPC (five-fold molar excess) for four hours at room temperature, and then repurified by size-exclusion into an assay buffer of 20 mM Tris-HCl, pH 7.5, 150 mM NaCl, and 5% glycerol. Protein used for crystallization was incubated with TEV protease to cleave the His tag. The cleaved protein was then separated from the His tag and TEV by a second round of nickel affinity chromatography. To make protein-ligand complexes, protein was incubated with ligands overnight (10-fold molar excess) and repurified by size-exclusion, using a final buffer of 100 mM ammonium acetate, pH 7.4, 150 mM sodium chloride, 1 mM DTT, 1 mM EDTA, and 2 mM CHAPS.

Thermofluor assays—Purified LRH-1 LBD-His protein (0.2 mg/ml) was incubated overnight with 50 µM of each compound at 4° C. The final DMSO concentration in the reactions was 1%. SYPRO orange dye (Invitrogen) was then added at a 1:1000 dilution. Reactions were heated at a rate of 0.5° C. per minute, using a StepOne Plus Real Time PCR System (ThermoFisher). Fluorescence was recorded at every degree using the ROX filter (602 nm). Data were analyzed by first subtracting baseline fluorescence (ligands+SYPRO with no protein) and then fitting the curves using the Bolzman equation (GraphPad Prism, v6) to determine the Tm.

Luciferase reporter assays—HeLa cells were seeded at a density of 10,000 cells per well in white-walled, clear-bottomed 96-well culture plates. The next day, cells were transfected with LRH-1 and reporters, using Fugene HD (Roche) at a ratio of 5:2 Fugene (µl):DNA (µg). The transfected plasmids included full-length LRH-1 in a pCI vector (5 ng/well), and a SHP-luc reporter, encoding the LRH-1 response element and surrounding sequence from the SHP promoter cloned upstream of firefly luciferase in the pGL3 basic vector (50 ng/well). Cells were also co-transfected with a constitutive *Renilla* luciferase reporter (utilizing the CMV promoter), which was used for normalization of firefly signal (1 ng/well). Control cells received pCI empty vector at 5 ng/well in place of LRH-1-pCI. Following an overnight transfection, cells were treated with agonists for 24 hours at the concentrations indicated in the figure legends. Agonists were dissolved in DMSO and then diluted into media, with a final concentration of 0.3% DMSO in all wells. Luciferase signal was quantified using the DualGlo kit (Promega). Experiments were conducted at least two times in triplicate.

Compounds were synthesized and evaluated in biological assays. Modifications to the scaffold were introduced at the RJW100 hydroxyl site, at the styrene ring, the other phenyl ring, and at other sites on the core of the molecule. Notably, the substitution of the hydroxyl with a sulfamino moiety (50-endo/exo) greatly stabilized the LRH-1-ligand complex with comparable or slightly higher LRH-1 activation. The crystal structure of LRH-1 bound to 50-endo was determined, which demonstrates that the ligand displaces the water molecule normally coordinated by LRH-1 residue T352 to directly interact with this threonine. The compound 40-endo also greatly stabilized the protein-ligand complex in Thermofluor assays and demonstrated increased activation of LRH-1 compared to RJW100. Compound 48-endo showed dose-dependent inhibition of LRH-1 activity.

A second strategy for improvement of activity involved modifications to the tail of the molecule. The effects of tail length and addition of various polar groups to the end of the tail were explored. Tail lengths of 8-10 carbons in length conferred the strongest activation of LRH-1.

Methods

Protein expression and purification—LRH-1 LBD (residues 299-541) in the pMSC7 vector was expressed in BL21(DE3) pLysS *E. coli* by induction with IPTG (1 mM) for 4 hr at 30° C. Protein was purified by nickel affinity chromatography. Protein used for thermofluor experiments was incubated with DLPC (five-fold molar excess) for four hours at room temperature, and then repurified by size-exclusion into an assay buffer of 20 mM Tris-HCl, pH 7.5, 150 mM NaCl, and 5% glycerol. Protein used for crystallization was incubated with TEV protease to cleave the His tag. The cleaved protein was then separated from the His tag and TEV by a second round of nickel affinity chromatography. To make protein-ligand complexes, protein was incubated with ligands overnight (10-fold molar excess) and repurified by size-exclusion, using a final buffer of 100 mM ammonium acetate, pH 7.4, 150 mM sodium chloride, 1 mM DTT, 1 mM EDTA, and 2 mM CHAPS.

Thermofluor assays—Purified LRH-1 LBD-His protein (0.2 mg/ml) was incubated overnight with 50 µM of each compound at 4° C. The final DMSO concentration in the reactions was 1%. SYPRO orange dye (Invitrogen) was then added at a 1:1000 dilution. Reactions were heated at a rate of 0.5° C. per minute, using a StepOne Plus Real Time PCR System (ThermoFisher). Fluorescence was recorded at every degree using the ROX filter (602 nm). Data were analyzed by first subtracting baseline fluorescence (ligands+SYPRO with no protein) and then fitting the curves using the Bolzman equation (GraphPad Prism, v6) to determine the Tm.

Luciferase reporter assays—HeLa cells were seeded at a density of 10,000 cells per well in white-walled, clear-bottomed 96-well culture plates. The next day, cells were transfected with LRH-1 and reporters, using Fugene HD (Roche) at a ratio of 5:2 Fugene (µl):DNA (µg). The transfected plasmids included full-length LRH-1 in a pCI vector (5 ng/well), and a SHP-luc reporter, encoding the LRH-1 response element and surrounding sequence from the SHP promoter cloned upstream of firefly luciferase in the pGL3 basic vector (50 ng/well). Cells were also co-transfected with a constitutive *Renilla* luciferase reporter (utilizing the CMV promoter), which was used for normalization of firefly signal (1 ng/well). Control cells received pCI empty vector at 5 ng/well in place of LRH-1-pCI. Following an overnight transfection, cells were treated with agonists for 24 hours at concentrations of 0.03, 0.3, 1, 3, 10, and 30 µM of each compound. Agonists were dissolved in DMSO and then diluted into media, with a final concentration of 0.3% DMSO in all wells. Luciferase signal was quantified using the DualGlo kit (Promega).

Crystallization—Protein-ligand complexes were incubated with a peptide derived from human Tif2 NR Box 3 or SMRT at four-fold molar excess for two hours at room temperature and then concentrated to 6.5 mg/ml. Crystallization conditions were identified using our Phoenix robot to screen in a high throughput manner or were based on the conditions used to produce RJW100-LRH-1 crystals.

Summary of Biological Data from Compound Screens $EC_{50}$ and Relative Activity values were calculated from luciferase reporter assays. Relative activity refers to fold increase in activity over baseline (DMSO-treated cells) for each compound relative to the fold increase induced by RJW100. A value of "0" indicates no activity over baseline, values between 0 and 1 indicate less active compounds, and values over 1 indicate compounds that are more active than RJW100 in these assays. ΔTm values were determined in thermofluor assays and refer to the difference in melting temperature of the LRH-1 ligand complex relative to DLPC-bound LRH-1 (PC 12:0/12:0, a phospholipid LRH-1 agonist). The Tm of RJW100 relative to DLPC is ~3° C.

Diols, Phosphorylcholines, Carboxylic Acids

| Compound Number | $EC_{50}$ (µM) | Relative Efficacy | ΔTm (mean +/− SEM) (° C.) |
|---|---|---|---|
| 5e | 1.4 +/− 0.5 | 0.83 | 3.1 +/− 0.9 |
| 6e | cnc | 1.57 | 2.4 +/− 0.3 |
| 7e | 1.0 +/− 0.8 | 1.74 | 3.3 +/− 0.8 |
| 8e | 0.2 +/− 0.2 | 1.26 | 3.7 +/− 0.8 |
| 9e | 0.7 +/− 0.9 | 1.52 | 4.0 +/− 0.5 |
| 10e | 1 +/− 2 | 1.30 | 4.1 +/− 0.6 |
| 11e | 2 +/− 5 | 2.83 | ns |
| 12e | 2 +/− 2 | 0.87 | 4.7 +/− 0.9 |
| 5g | cnc | 0.33 | ns |
| 6g | cnc | 0.00 | ns |
| 7g | cnc | 0.00 | ns |
| 8g | cnc | 0.81 | 2.9 +/− 0.4 |
| 9g | >30 | 1.12 | 5.6 +/− 0.6 |
| 10g | 2 +/− 3 | 2.74 | ns |
| 11g | 5 +/− 2 | 2.48 | −2.4 +/− 0.5 |
| 12g | 5.1 +/− 0.5 | 0.93 | −1.7 +/− 0.9 |
| 5f | cnc | 1.43 | 2.3 +/− 0.2 |
| 6f | cnc | 0.60 | 1.3 +/− 0.4 |
| 7f | 9 +/− 3 | 2.22 | 5.5 +/− 0.3 |
| 8f | 4 +/− 3 | 1.17 | 3.7 +/− 0.2 |
| 9f | 4 +/− 2 | 2.48 | 4.4 +/− 0.5 |
| 10f | 1.8 +/− 0.7 | 3.39 | 3 +/− 1 |
| 11f | 0.4 +/− 0.4 | 2.39 | ns |
| 12f | 0.3 +/− 0.3 | 1.74 | 2.5 +/− 0.3 |

Other Tail Modifications and Hybrids

| Compound Number | EC$_{50}$ (μM) | Relative Efficacy | ΔTm (mean +/− SEM) (° C.) |
|---|---|---|---|
| 13b | 12 +/− 6 | 0.96 | nd |
| 45b | 0.07 +/− 0.3 | 0.66 | 8.4 +/− 0.2 |
| 45c | 0.2 +/− 0.1 | 1.85 | ns |
| 46b | >30 | 0.51 | 8.5 +/− 0.2 |
| 47-endo | nd | 1.48 | ns |
| 47-exo | 0.7 +/− 0.7 | 3.70 | 1.5 +/− 0.2 |
| 51 | cnc | 0.65 | nd |
| 52 | 0.01 +/− 0.03 | −0.25 | nd |
| 53-endo | nd | 1.04 | ns |
| 53-exo | nd | 0.37 | ns |
| 54 | 16 +/− 11 | 1.05 | nd |
| 14d | 17 +/− 7 | 3.35 | nd |

Modifications at RJW100 Internal Styrene

| Compound Number | EC$_{50}$ (μM) | Relative Efficacy | ΔTm (mean +/− SEM) (° C.) |
|---|---|---|---|
| 15f | cnc | 0.85 | 1.4 +/− 0.1 |
| 15g | cnc | 0.70 | ns |
| 16f | >30 | 0.9 | ns |
| 16g | 24 +/− 47 | 3.8 | ns |
| 17f | 3 +/− 4 | 0.6 | −1.9 +/− 0.5 |
| 17g | >30 | 2.7 | ns |
| 18f | >30 | 2.8 | ns |
| 18g | cnc | 0.99 | 1.5 +/− 0.2 |

Modifications at RJW100 External Styrene

| Compound Number | EC$_{50}$ (μM) | Relative Efficacy | ΔTm (mean +/− SEM) (° C.) |
|---|---|---|---|
| 20 | 4 +/− 4 | 0.85 | 1.4 +/− 0.7 |
| 21 | 0.9 +/− 0.5 | 0.87 | 1.3 +/− 0.2 |
| 22 | cnc | 0.42 | ns |
| 24 | cnc | −0.14 | −3.1 +/− 0.8 |
| 23a | cnc | 0.06 | nd |
| 23b | 5 +/− 9 | 0.86 | ns |
| 25-endo | cnc | 0.42 | ns |
| 25-exo | 0.8 +/− 0.7 | 0.31 | 1.0 +/− 0.4 |
| 26-endo | 0.4 +/− 1 | 0.11 | 1.9 +/− 0.1 |
| 26-exo | 9 +/− 4 | 1.41 | 1.4 +/− 0.1 |

Modifications at RJW100 Hydroxyl Site

| Compound Number | EC$_{50}$ (μM) | Relative Efficacy | ΔTm (mean +/− SEM) (° C.) |
|---|---|---|---|
| 27 | nd | −0.42 | ns |
| 28-endo | 0.9 +/− 0.6 | 0.96 | 8 +/− 2 |
| 28-exo | 0.8 +/− 0.6 | 0.62 | 5.1 +/− 0.2 |
| 29-endo | cnc | 0 | 2.8 +/− 0.3 |
| 29-exo | cnc | 0.14 | 1.54 +/− 0.04 |
| 30-endo | 0.5 +/− 0.2 | 0.72 | 3 +/− 1 |
| 30-exo | 1 +/− 1 | 0.14 | 1.1 +/− 0.4 |
| 31-endo | 5 +/− 5 | 0.70 | ns |
| 31-exo | 2 +/− 3 | 0.45 | ns |
| 32-endo | nd | 0 | ns |
| 32-exo | nd | 0 | ns |
| 33-endo | nd | 0.56 | ns |
| 33-exo | nd | 0.56 | −3.0 +/− 0.8 |
| 34-endo | 1 +/− 1 | 1.2 | 3.6 +/− 0.4 |
| 34-exo | cnc | cnc | 0.6 +/− 0.3 |
| 35-endo | 13 +/− 8 | 2.6 | 0.4 +/− 0.4 |
| 35-exo | 17 +/− 113 | −0.1 | −1.1 +/− 0.6 |
| 36-endo | 0.5 +/− 0.7 | 0.30 | 1.1 +/− 0.3 |
| 36-exo | 2 +/− 3 | 0.41 | −1.4 +/− 0.4 |
| 37-endo | 0.015 +/− 0.008 | 1.3 | 9.2 +/− 0.5 |

-continued

| Compound Number | EC$_{50}$ (μM) | Relative Efficacy | ΔTm (mean +/− SEM) (° C.) |
|---|---|---|---|
| 37-exo | 0.04 +/− 0.05 | 0.39 | 4.1 +/− 0.3 |
| 39-endo | nd | 0.13 | 0.4 +/− 0.9 |
| 39-exo | nd | 0.06 | 0.1 +/− 1 |
| 40-endo | >30 | −0.2 | 1.95 +/− 0.15 |
| 40-exo | >30 | 0 | nd |
| 48-endo | cnc | 0 | 0 |

Cnc = could not calculate EC50
Nd = not done
Ns = Tm changes were less than ° C.

What is claimed is:

1. A method of treating cardiovascular disease comprising administering to a subject in need thereof an effective amount of a compound having the following formula:

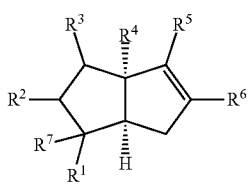

Formula I prodrugs or salts thereof wherein,

R$^1$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, benzoyl, benzyl, aryl, or heterocyclyl, wherein R$^1$ is optionally substituted with one or more, the same or different, R$^{10}$;

R$^2$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkylsulfonyl, aryl sulfonyl, carbocyclyl, benzoyl, benzyl, aryl, or heterocyclyl, wherein R$^2$ is optionally substituted with one or more, the same or different, R$^{10}$;

R$^3$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkylsulfonyl, aryl sulfonyl, carbocyclyl, benzoyl, benzyl, aryl, or heterocyclyl, wherein R$^3$ is optionally substituted with one or more, the same or different, R$^{10}$;

R$^4$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, benzoyl, benzyl, aryl, or heterocyclyl, wherein R$^4$ is optionally substituted with one or more, the same or different, R$^{10}$;

R$^5$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, benzoyl, benzyl, aryl, or heterocyclyl, wherein R$^5$ is optionally substituted with one or more, the same or different, R$^{10}$;

R⁶ is lipid or alkyl, wherein R⁶ is optionally terminally substituted with a hydroxy, carboxy, or phosphate, wherein the hydroxy, carboxy, or phosphate are optionally further substituted with R¹⁰;

R⁷ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)₂amino, alkanoyl, alkoxycarbonyl, alkyl sulfinyl, alkyl sulfonyl, aryl sulfonyl, carbocyclyl, benzoyl, benzyl, aryl, or heterocyclyl, wherein R⁷ is optionally substituted with one or more, the same or different, R¹⁰; or R¹ and R⁷ together are an oxo or oxime, wherein the oxime is optionally substituted with one or more, the same or different, R¹⁰;

R¹⁰ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)₂amino, alkanoyl, alkoxycarbonyl, alkylsulfinyl, alkyl sulfonyl, arylsulfonyl, aminosulfonyl, carbocyclyl, benzoyl, benzyl, aryl, or heterocyclyl, wherein R¹⁰ is optionally substituted with one or more, the same or different, R¹¹; and R¹¹ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydroxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethylsulfinyl, mesyl, ethyl sulfonyl, methoxycarbonyl, ethoxycarbonyl, isopropoxycarbonyl, tert-butoxycarbonyl, N-methyl sulfamoyl, N-ethyl sulfamoyl, N,N-dimethylsulfamoyl, N,N-diethylsulfamoyl, N-methyl-N-ethylsulfamoyl, benzoyl, benzyl, carbocyclyl, aryl, or heterocyclyl.

2. The method of claim 1, the compound has one of the following formula:

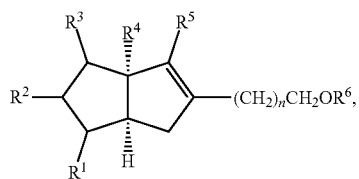

Formula IA

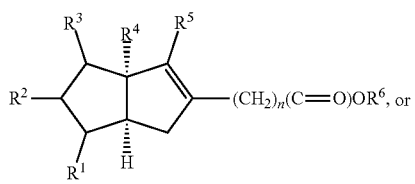

Formula IB

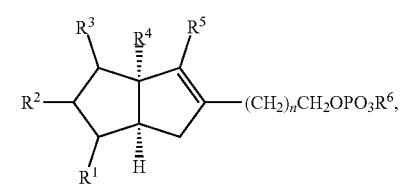

Formula IC wherein R⁶ is hydrogen, alkyl, or alkanoyl optionally substituted with R¹⁰.

3. The method of claim 1, the compound has one of the following formula:

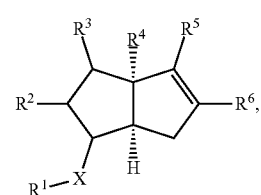

Formula ID

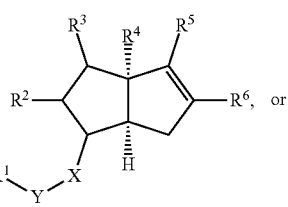

Formula IE

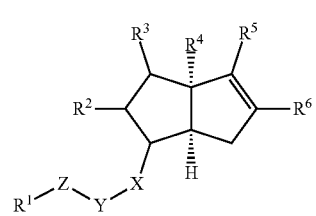

Formula IF wherein,

X is —CH₂—, —C(OH)(OH)—, —C(OH)H, —C(Hal)(Hal)-, —C(Hal)H—, —O—, —S—, —(S=O)—, —SO₂—, —NH—, —(C=O)—, —(C=NH)—, or —(C=S)—;

Y is —CH₂—, —C(OH)(OH)—, —C(OH)H, —C(Hal)(Hal)-, —C(Hal)H—, —O—, —S—, —(S=O)—, —SO₂—, —NH—, —(C=O)—, —(C=NH)—, or —(C=S)—;

Z is —CH₂—, —C(OH)(OH)—, —C(OH)H, —C(Hal)(Hal)-, —C(Hal)H—, —O—, —S—, —(S=O)—, —SO₂—, —NH—, —(C=O)—, —(C=NH)—, or —(C=S)—; and R¹ is hydrogen, hydroxy, alkyl, alkanoyl, amino, aminoalkyl, carbamoyl, sulfate, sulfonate, aminosulfonyl, phosphate, phosphonate, or heterocyclyl.

4. The method of claim 3, wherein
a) X is O, and R¹ is alkanoyl;
b) X is —NH—, and R¹ is alkanoyl;
c) X is O, and R¹ is aminosulfonyl;
d) X is —NH—, and R¹ is aminosulfonyl;
e) X is —(C=O)—, R¹ is amino;
f) X is O, Y is —(C=O)—, R¹ is amino;
g) X is O, Y is —(C=O)—, Z is —NH—, and R¹ is sulfonate; and
h) X is O, Y is —(C=O)—, Z is —NH—, and R¹ is aminosulfonyl.

5. The method of claim 1, wherein the compound is 5-hexyl-4-phenyl-3a-(1-phenylvinyl)-1,2,3,3a,6,6a-hexahydropentalen-1-yl sulfamide or salt thereof.

6. The method of claim 1, wherein the compound is 5-hexyl-4-phenyl-3a-(1-phenylvinyl)-1,2,3,3a,6,6a-hexahydropentalen-1-yl)acetamide or salt thereof.

7. The method of claim 1, wherein the cardiovascular disease is cardiovascular disease is selected from coronary artery disease (CAD), angina, myocardial infarction, stroke, hypertensive heart disease, rheumatic heart disease, cardiomyopathy, heart arrhythmia, congenital heart disease, valvular heart disease, carditis, aortic aneurysms, peripheral artery disease, and venous thrombosis.

8. A method of treating diabetes comprising administering to a subject in need thereof an effective amount of a compound having the following formula:

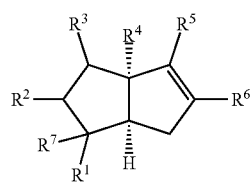

Formula I prodrugs or salts thereof wherein,
$R^1$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, benzoyl, benzyl, aryl, or heterocyclyl, wherein $R^1$ is optionally substituted with one or more, the same or different, $R^{10}$;
$R^2$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, aryl sulfonyl, carbocyclyl, benzoyl, benzyl, aryl, or heterocyclyl, wherein $R^2$ is optionally substituted with one or more, the same or different, $R^{10}$;
$R^3$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, aryl sulfonyl, carbocyclyl, benzoyl, benzyl, aryl, or heterocyclyl, wherein $R^3$ is optionally substituted with one or more, the same or different, $R^{10}$;
$R^4$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, benzoyl, benzyl, aryl, or heterocyclyl, wherein $R^4$ is optionally substituted with one or more, the same or different, $R^{10}$;
$R^5$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, benzoyl, benzyl, aryl, or heterocyclyl, wherein $R^5$ is optionally substituted with one or more, the same or different, $R^{10}$;
$R^6$ is lipid or alkyl, wherein $R^6$ is optionally terminally substituted with a hydroxy, carboxy, or phosphate, wherein the hydroxy, carboxy, or phosphate are optionally further substituted with $R^{10}$;
$R^7$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkylsulfonyl, aryl sulfonyl, carbocyclyl, benzoyl, benzyl, aryl, or heterocyclyl, wherein $R^7$ is optionally substituted with one or more, the same or different, $R^{10}$; or
$R^1$ and $R^7$ together are an oxo or oxime, wherein the oxime is optionally substituted with one or more, the same or different, $R^{10}$;
$R^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, arylsulfonyl, aminosulfonyl, carbocyclyl, benzoyl, benzyl, aryl, or heterocyclyl, wherein $R^{10}$ is optionally substituted with one or more, the same or different, $R^{11}$; and
$R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydroxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethyl carbamoyl, N,N-dimethylcarbamoyl, N,N-diethylcarbamoyl, N-methyl-N-ethylcarbamoyl, methylthio, ethylthio, methyl sulfinyl, ethylsulfinyl, mesyl, ethyl sulfonyl, methoxycarbonyl, ethoxycarbonyl, isopropoxycarbonyl, tert-butoxycarbonyl, N-methyl sulfamoyl, N-ethyl sulfamoyl, N,N-dimethylsulfamoyl, N,N-diethylsulfamoyl, N-methyl-N-ethylsulfamoyl, benzoyl, benzyl, carbocyclyl, aryl, or heterocyclyl.

9. The method of claim 8, the compound has one of the following formula:

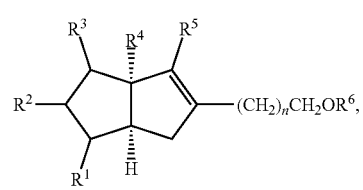

Formula IA

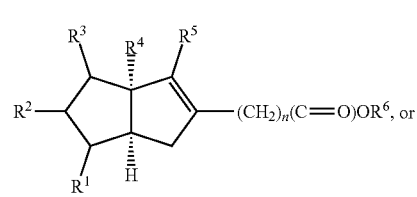

Formula IB

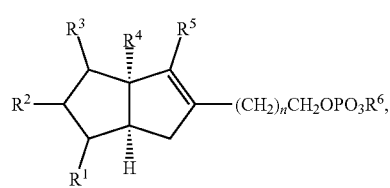

Formula IC wherein $R^6$ is hydrogen, alkyl, or alkanoyl optionally substituted with $R^{10}$.

10. The method of claim 8, the compound has one of the following formula:

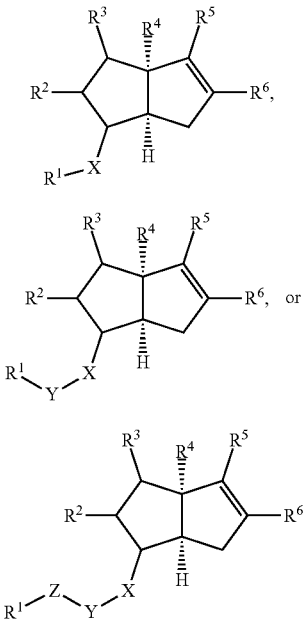

Formula ID

Formula IE

Formula IF wherein,

X is —CH$_2$—, —C(OH)(OH)—, —C(OH)H, —C(Hal)(Hal)-, —C(Hal)H—, —O—, —S—, —(S=O)—, —SO$_2$—, —NH—, —(C=O)—, —(C=NH)—, or —(C=S)—;

Y is —CH$_2$—, —C(OH)(OH)—, —C(OH)H, —C(Hal)(Hal)-, —C(Hal)H—, —O—, —S—, —(S=O)—, —SO$_2$—, —NH—, —(C=O)—, —(C=NH)—, or —(C=S)—;

Z is —CH$_2$—, —C(OH)(OH)—, —C(OH)H, —C(Hal)(Hal)-, —C(Hal)H—, —O—, —S—, —(S=O)—, —SO$_2$—, —NH—, —(C=O)—, —(C=NH)—, or —(C=S)—; and R$^1$ is hydrogen, hydroxy, alkyl, alkanoyl, amino, aminoalkyl, carbamoyl, sulfate, sulfonate, aminosulfonyl, phosphate, phosphonate, or heterocyclyl.

11. The method of claim 10, wherein
a) X is O, and R$^1$ is alkanoyl;
b) X is —NH—, and R$^1$ is alkanoyl;
c) X is O, and R$^1$ is aminosulfonyl;
d) X is —NH—, and R$^1$ is aminosulfonyl;
e) X is —(C=O)—, R$^1$ is amino;
f) X is O, Y is —(C=O)—, R$^1$ is amino;
g) X is O, Y is —(C=O)—, Z is —NH—, and R$^1$ is sulfonate; and
h) X is O, Y is —(C=O)—, Z is —NH—, and R$^1$ is aminosulfonyl.

12. The method of claim 8, wherein the compound is 5-hexyl-4-phenyl-3a-(1-phenylvinyl)-1,2,3,3a,6,6a-hexahydropentalen-1-yl sulfamide or salt thereof.

13. The method of claim 8, wherein the compound is 5-hexyl-4-phenyl-3a-(1-phenylvinyl)-1,2,3,3a,6,6a-hexahydropentalen-1-yl)acetamide or salt thereof.

14. The method of claim 8, wherein diabetes is selected from insulin-dependent diabetes mellitus, non insulin-dependent diabetes mellitus, and gestational diabetes.

* * * * *